United States Patent [19]

Camble et al.

[11] Patent Number: 5,320,840

[45] Date of Patent: Jun. 14, 1994

[54] CONTINUOUS RELEASE PHARMACEUTICAL COMPOSITIONS

[75] Inventors: Roger Camble; David Timms; Anthony J. Wilkinson, all of Macclesfield, England

[73] Assignee: Imperial Chemical Industries PLC, London, England

[21] Appl. No.: 734,225

[22] Filed: Jul. 22, 1991

[30] Foreign Application Priority Data

| Jul. 23, 1990 | [GB] | United Kingdom | 9016138 |
| Aug. 23, 1990 | [GB] | United Kingdom | 9018414 |
| Aug. 23, 1990 | [GB] | United Kingdom | 9018415 |
| Aug. 23, 1990 | [GB] | United Kingdom | 9018416 |
| Aug. 23, 1990 | [GB] | United Kingdom | 9018417 |
| Aug. 23, 1990 | [GB] | United Kingdom | 9018418 |

[51] Int. Cl.⁵ .......................... A61K 37/02
[52] U.S. Cl. .................. 424/85.1; 530/351; 530/410; 530/411; 530/406; 514/964; 514/965
[58] Field of Search .......... 530/351, 410, 411, 406, 530/307; 525/54.1; 424/85.1, 85.2, 85.4, 85.5, 85.6, 85.7; 514/2, 812, 13, 808, 964, 965

[56] References Cited

U.S. PATENT DOCUMENTS

| 4,179,337 | 12/1979 | Davis | 435/181 |
| 4,414,147 | 11/1983 | Klibanov | 530/351 |
| 4,766,106 | 8/1988 | Katre et al. | 530/351 |
| 4,767,628 | 8/1988 | Hutchinson | 514/12 |
| 4,810,643 | 3/1989 | Souza | 435/68 |
| 4,818,769 | 4/1989 | Nunberg et al. | 514/12 |
| 4,894,226 | 1/1990 | Aldwin | 424/85.2 |
| 4,904,584 | 2/1990 | Shaw | 530/351 |
| 4,917,888 | 4/1990 | Katre | 424/85.91 |
| 4,942,035 | 7/1990 | Churchill et al. | 514/772.3 |
| 5,055,555 | 10/1991 | Sassenfeld | 530/351 |
| 5,192,741 | 3/1993 | Orsolini et al. | 514/4 |
| 5,236,704 | 8/1993 | Fujioka et al. | 424/85.1 |

FOREIGN PATENT DOCUMENTS

| 0098110 | 1/1984 | European Pat. Off. |
| 0154316 | 9/1985 | European Pat. Off. |
| 0183503 | 6/1986 | European Pat. Off. |
| 0236987 | 9/1987 | European Pat. Off. |
| 0335423 | 10/1989 | European Pat. Off. |
| 0338916 | 10/1989 | European Pat. Off. |
| 0401384 | 12/1990 | European Pat. Off. |
| 0459630 | 12/1991 | European Pat. Off. |
| 8604145 | 7/1986 | PCT Int'l Appl. |
| 8700056 | 1/1987 | PCT Int'l Appl. |
| 8906546 | 7/1989 | PCT Int'l Appl. |
| 9004606 | 5/1990 | PCT Int'l Appl. |
| 1280497 | 7/1972 | United Kingdom |

OTHER PUBLICATIONS

Hora et al, Controlled Release of Interleukin-2 From Biodegradable Microspheres, Biotechnology, vol. 8, Aug. 1990, pp. 775–758.

Hora et al, Proceed, Intern. Symp. Control. Rel. Bioact. Mater. 16, (1989) No. 268, pp. 509–510.

Schulz et al, *Principles of Protein Structure*, Springer-Verlag, 1979, pp. 14–16.

Dayhoff, *Atlas of Protein Sequence and Structure 1972*, Nat. Biomed. Res. Found. vol. 5, p. 96.

Primary Examiner—Jeffrey E. Russel
Attorney, Agent, or Firm—Cushman, Darby & Cushman

[57] ABSTRACT

Pharmaceutical compositions for continuous release of a physiologically active substance in which the physiologically active substance comprises a polypeptide covalently conjugated to a water soluble polymer show particularly desirable release characteristics. Polypeptides for use in the pharmaceutical compositions include G-CSF and solution stable derivatives thereof, human calcitonin and interleukin-2. The material of the composition may be a polylactide or biodegradable hydrogel derived from an amphipathic block copolymer.

The compositions enable a therapeutically effective polypeptide to be continuously released over a prolonged period of time following a single administration of the pharmaceutical composition to a patient.

10 Claims, 17 Drawing Sheets

Fig. 1

```
EcoR1
AATTCTGGCA AATATTCTGA AATGAGCTGT TGACAATTAA TCATCGAACT      50
           GACCGT TTATAAGACT TTACTCGACA ACTGTTAATT AGTAGCTTGA  46

HpaI
AGTTAACTAG TACGCAAGTT CACGTAAAAA GGGTATCGAC                  90
TCAATTGATC ATGCGTTCAA GTGCATTTTT CCCATAGCTG                  86

KpnI    BamHI   XbaI   SalI  PstI  SphI
AATGGTACCC GGGGATCCTC TAGAGTCGAC CTGCAGGCAT GCAAGCTTAG       140
TTACCATGGG CCCCTAGGAG ATCTCAGCTG GACGTCCGTA CGTTCGAATC       136

ClaI
CCCGCCTAAT GAGCGGGCTT TTTTTAT                                168
GGGCGGATTA CTCGCCCGAA AAAAATAGC                              166
```

Fig. 2

```
EcoRI   ScaI
AATTCAGT ACT CCA CTG GGT CCA GCA AGC TCT CTG CCG CAG TCT CTT CTG AAG TGT  59
    GTCA TGA GGT GAC CCA GGT CGT TCG AGA CAG GGC GTC AGA AGA GAC TTC ACA
         Thr Pro Leu Gly Pro Ala Ser Ser Leu Pro Gln Ser Phe Leu Lys Cys
          1                       5                      10              15
                   SnabI                                              FspI CTC GAA CAG GTA CGT AAA ATT CAA GGC GAT GGT GCG GCT CTG CAG GAA AAG CTG TGC GCA  119
GAG CTT GTC CAT GCA TTT TAA GTT CCG CTA CCA CGC CGA GAC GTC CTT TTC GAC ACG CGT
Leu Glu Gln Val Arg Lys Ile Gln Gly Asp Gly Ala Ala Leu Gln Glu Lys Leu Cys Ala
             20                      25                      30                35
                             MstII                                         BamHI ACC TAC AAA CTG TGC CAC CCT GAG CTG GTG CTC GAC CTC CAC TCT CTG GGG ATG CCG  179
TGG ATG TTT GAC ACG GTG GGA CTC GAC CAC GAG CTG GAG GTG AGA GAC CCC TAG GGC
Thr Tyr Lys Leu Cys His Pro Glu Leu Val Leu Asp Leu His Ser Leu Gly His Ile Pro
             40                      45                      50                55
          SacI                             HindIII TGG GCT CCA CTG AGC TCT TGC CCA TCC CAA CTG GCA GGC TTG AGC CAG  219
ACC CGA GGT GAC TCG AGA ACG GGT AGG GTT GAC CGT CCG AAC TCG GTC
Trp Ala Pro Leu Ser Ser Cys Pro Ser Gln Leu Ala Gly Cys Leu Ser Gln
             60                      65                      70                75
                                                    XbaI
```

```
DcoRI ScaI

AATTCAGT ACT CCA CTG GGT CCA GCA AGC TCT CTG CCG CAG TCT CTG AAG TCT    59
    GTCA TGA GGT GAC CCA GGT CGT TCG AGA GGC GTC AGA GAC TTC AGA
         Thr Pro Leu Gly Pro Ala Ser Ser Leu Pro Gln Ser Phe Leu Lys Ser
          1                         5                        10          15
                 SnabI                                              FspI CTC GAA CAG GTA CGT AAA ATT CAA GGC AGC GGT GCG GCT CGA GAA AAG CTG TGC GCA    119
GAG CTT GTC CAT GCA TTT TAA GTT CCG TCG CCA CGC GCT CTT TTC GAC ACG CGT
Leu Glu Gln Val Arg Lys Ile Gln Gly Ser Gly Ala Ala Leu Glu Lys Leu Cys Ala
         20                        25                        30                  35
                     MstII                                                BamHI ACC TAC AAA CTG TGC CAC CCT GAG GAA CTG GTG CTC GGT CAC TCT CTG GGG ATC CCG    179
TGG ATG TTT GAC ACG GTG GGA CTC CTT GAC CAC GAG CCA GTG AGA GAC CCC TAG GGC
Thr Tyr Lys Leu Cys His Pro Glu Glu Leu Val Leu Gly His Ser Leu Gly Ile Pro
         40                        45                        50                  55
             SacI                            HindIII TGG GTC CCA CTG AGC TCT TGC CCG TCC CAA GCT TTA CAA GCT GCA GGC TGC TTG AGC CAG    219
ACC CGA GGT GAC TCG AGA ACG GGC AGG GTT CGA AAT GTT CGA CGT CCG ACG AAC TCG GTC
Trp Val Pro Leu Ser Ser Cys Pro Ser Gln Ala Leu Gln Ala Ala Gly Cys Leu Ser Gln
         60                        65                        70                  75
                                                        XbaI CTG CAC TCC GGT CTG TTC CTT CTG TAC CAG GGT CTG CAG GCT CTA GAA GGC ATC TCT CCT    299
GAC GTG AGG CCA GAC AAG GAA GAC ATG GTC CCA GAC GTC CGA GAT CTT CCG TAG AGA GGA
Leu His Ser Gly Leu Phe Leu Leu Tyr Gln Gly Leu Gln Ala Leu Glu Gly Ile Ser Pro
         80                        85                        90                  95
                                                                          NdeI
```

Fig. 3(cont.)

```
GAA TTG GGG CCC ACC CTG GAC ACA CTG CAG CTG GAC GTT GCC GAC TTC GCT ACT ACC ATA    359
CTT ACC CCC GGG TGG GAC CTG TGT GAC GTC GAC CTG CAA CGG CTG AAG CGA TGA TGG TAT
Glu Leu Gly Pro Thr Leu Asp Thr Leu Gln Leu Asp Val Ala Asp Phe Ala Thr Thr Ile
100                         105                         110                    115

TGG CAA CAG ATG GAG GAA CTG GGT ATG GCT CCG GCA CTG CAG CCG ACT CAG CCG GGT GCG ATG    419
ACC GTT GTC TAC CTC CTT GAC CCA CCA TAC CGA GGC CGT GAC GTC GGC TGA GTC CCA CGC TAC
Trp Gln Gln Met Glu Glu Leu Gly Met Ala Pro Ala Leu Gln Pro Thr Gln Pro Gly Ala Met
     120                         125                         130                    135
                                                  BssHII

CCA GCA TTC GCC TCT GCT TTC CAG CGG CGC GCA GGC GGT GTT CTG GTT GCC TCC CAT CTT    479
GGT CGT AAG CGG AGA CGA AAG GTC GCC GCG CGT CCG CCA CAA GAC CAA CGG AGG GTA GAA
Pro Ala Phe Ala Ser Ala Phe Gln Arg Arg Ala Gly Gly Val Leu Val Ala Ser His Leu
140                         145                         150                    155
        XhoI                                                                    SalI
CAG AGC TTC CTC GAG GTG TCT TAC CGC GTT CTG CGT CAG CTG GCC CAG CCG TAA G          534
GTC TCG AAG GAG CTC CAC AGA ATG GCG CAA GAC GCA GTC GAC CGG GTC GGC ATT CAGCT
Gln Ser Phe Leu Glu Val Ser Tyr Arg Val Leu Arg His Leu Ala Gln Pro
160                         165                         170    174
```

Fig. 4(a)

Sal I
5' TCGACATTATATTACTAATTAATTGGGACCCTAGAGGTCCCCTTTTTATTTTAA
3'        GTAATATAATGATTAATTAACCCCTGGGATCTCCAGGGGAAAAATAAAATT

SphI HindIII
       AAGCATGCA        3'
       TTTCGTACGTTCGA   5'

Fig. 4(b)

Sal I
5' TCGACATTATATTACTAATTAATTGGGACCCTAGAGGTCCCCTTTTTATTTTAA
3'        GTAATATAATGATTAATTAACCCCTGGGATCTCCAGGGGAAAAATAAAATT

AAAGCATGCGGATCCC       3'
TTTCGTACGCCTAGGGAAC    5'

Fig. 6

EcoR1
AATTCTGGCA AATATTCTGA AATGAGCTGT TGACAATTAA TCATCGAACT

HpaI
AGTTAACTAG TACGCCAGAGC TCAATCTAGA GGGTATTAAT AATGTTCCCA

TTGGAGGATG ATTAATG

CONTINUOUS RELEASE PHARMACEUTICAL COMPOSITIONS

The present invention relates to pharmaceutical compositions of physiologically active polypeptides which provide continuous release of the polypeptide over an extended period when the composition is placed in an aqueous physiological-type environment (as hereinafter defined).

BACKGROUND

It has long been appreciated that the continuous release of certain drugs over an extended period following a single administration could have significant practical advantages in clinical practice, and compositions have already been developed to provide extended release of a number of clinically useful drugs, after oral dosing (see, for example Remington's Pharmaceutical Sciences, published by Mack Publishing Company, Easton, Pennsylvania, USA, 15th Edition, 1975, pages 1618–1631), after parenteral administration (ibidem, pages 1631–1643),and after topical administration (see, for example, United Kingdom Patent Number 1,351,409). A suitable method of parenteral administration is the sub-dermal injection or implantation of a solid body, for example a pellet or a film, containing the drug, and a variety of such implantable devices has been described. In particular, it is known that, for many drugs, suitable implantable devices or injectable microparticle suspensions for providing extended drug release may be obtained by encapsulating the drug in a biodegradable polymer, or by dispersing the drug in a matrix of such a polymer, so that the drug is released as the degradation of the polymer matrix proceeds.

Suitable biodegradable polymers for use in sustained release formulations are well known, and include polyesters, which gradually become degraded by hydrolysis when placed in an aqueous, physiological-type environment. Particular polyesters which have been used are those derived from hydroxycarboxylic acids, and much prior art has been directed to polymers derived from alpha hydroxycarboxylic acids, especially lactic acid in both its racemic and optically active forms, and glycolic acid, and copolymers thereof-see, for example, U.S. Pat. Nos. 3,773,919 and 3,887,699; Jackanicz et al., Contraception, 1973, 8, 227–234; Anderson et al., ibidem, 1976, 11, 375–384; Wise et al., Life Sciences, 1976, 19, 867–874; Woodland et al., Journal of Medicinal Chemistry, 1973, 16, 897–901; Yolles et al., Bulletin of the Parenteral Drug Association, 1976, 30, 306–312; Wise et al., Journal of Pharmacy and Pharmacology, 1978, 30, 686–689 and 1979, 31, 201–204.

It is to be appreciated that "sustained" or "extended" release of a drug may be either continuous or discontinuous. For example, the release of a polypeptide from a polylactide polymer as described in UK Patent Specification No. 1,325,209 is often preceded by a significant induction period, during which no polypeptide is released, or is biphasic, and comprises an initial period during which some polypeptide is released, a second period during which little or no polypeptide is released, and a third period during which most of the remainder of the polypeptide is released. By contrast, it is an object of the present invention to provide compositions of polypeptides from which, apart possibly from a relatively short initial induction period, the polypeptide is released continuously, with no periods during which little or no polypeptide is released. The words "continuous release" are used in this specification solely to describe a release profile which is essentially monophasic, although it may have a point of inflection, but certainly has no "plateau" phase when cumulative release of drug is plotted as a function of time.

In our European Patent No. 58,481 we describe continuous release pharmaceutical compositions which enable essentially monophasic release of acid stable polypeptides to be obtained. These compositions, in general, comprise a polylactide, which is a polymer of lactic acid alone, a copolymer of lactic and glycolic acids, a mixture of such polymers, a mixture of such copolymers or a mixture of such polymers and copolymers, and an acid-stable (as hereinafter defined) polypeptide, which is not significantly hydrolysed under the conditions encountered within the composition during the period of use envisaged, which composition, when placed in an aqueous physiological-type environment (as hereinafter defined), releases the polypeptide into the aqueous physiological-type environment in continuous manner, giving a release profile which is essentially monophasic, although it may have a point of inflection, but certainly has no "plateau" phase, over a period of at least one week.

As stated above European Patent Publication No 58,481 relates to formulations of polypeptides which are stable under the conditions encountered within the claimed formulation. Certain polypeptides, however, such as native [Met$^{-1}$] human G-CSF are inherently unstable under such conditions, suffering from a range of instability problems including inter alia the tendency to aggregate. The present invention is based on the discovery that conjugation with a water soluble polymer may overcome or at least ameliorate problems of instability present in certain polypeptides that would not otherwise be stable under the conditions encountered within the depot and would therefore not release adequately. The present invention is also based on the discovery that the use of a physiologically active substance in which a physiologically active polypeptide is covalently conjugated to a water soluble polymer, improves release profile over the corresponding unconjugated polypeptide in continuous release pharmaceutical compositions.

Recently Hora M. S. et.al have published in Proceed. Intern Symp. Control. Rel. Bioact. Mater. 16, (1989) No 268 on pages 509–510 the development of a controlled release microsphere formulation of interleukin-2. Hora M. S. et al demonstrate that a triphasic release pattern is obtained when pegylated interleukin-2 (IL-)2 covalently conjugated with polyethylene glycol (PEG) and referred to hereinafter as PEG IL-2) in the presence of foetal calf serum is released from poly (DL-lactide-co-glycolide) microspheres and further that a 5- to 15- day long lag or induction period is encountered. Hora M. S. et al seek to overcome the identified problems by attempting to improve the wetting and resolubilisation of the PEG IL-2 by the use of human serum albumin (HSA). This attempt introduces a further problem, that is the presence of solubilising protein. The presence of such protein in a pharmaceutical formulation is disadvantageous, inter alia because it enhances the risk of adverse side reaction and impedes analytical accuracy.

Furthermore the Hora M. S. et al publication referred to above fails to define either the solubility characteristics of the poly (Dl-lactide-co-glycolide)polymer (specifically whether the polymer is soluble or insoluble in benzene) or the polydispersity (as hereinafter defined). In the absence of these facts and in the absence of the method of preparation the work could not be repeated and the publication is thus not enabling. It is further noted that the publication additionally fails to define the molecular weight of the polyethylene glycol (PEG) or the level of pegylation, both of which factors are necessary if the published work is to be repeated.

In view of the poor continuous release results obtained by Hora M. S. et al with pegylated IL-2 it is particularly surprising that in accordance with the present invention such a good release profile should be obtainable by the use of physiologically active polypeptides covalently conjugated to a water soluble polymer.

SUMMARY OF THE INVENTION

Thus according to one feature of the present invention there is provided a pharmaceutical composition for continuous release of an acid stable (as hereinafter defined) physiologically active substance from material of the composition into an aqueous physiological-type environment (as hereinafter defined), wherein the said substance is a polypeptide covalently conjugated to a water soluble polymer which substance is not significantly hydrolysed under the conditions encountered within the composition during the period of use envisaged, which composition, i) when placed in an aqueous physiological-type environment, releases the polypeptide into the aqueous physiological-type environment in continuous manner, giving a release profile which is essentially monophasic (as herein defined) over a period of at least one week;

ii) exhibits two successive phases of release of the polypeptide, the first phase being released by diffusion from the surface and the second phase being released consequent upon degradation of material of the composition, characterised in that the diffusion phase and the degradation-induced phase overlap in time, and release of polypeptide occurs over a period of at least one week; or iii) absorbs water in a continuous manner, giving a water absorption profile which is essentially monophasic, until the material of the composition has been degraded and essentially all of the polypeptide has been released into the aqueous physiological-type environment, over a period of at least one week.

According to a further feature of the present invention there is provided a method for providing haematopoietic therapy to a mammal which comprises administering a pharmaceutical composition of the present invention to said mammal whereby to deliver an effective amount of a polypeptide conjugated to water soluble polymer, said polypeptide having at least one of the biological properties of naturally occurring G-CSF.

According to a further feature of the present invention there is provided a method for arresting the proliferation of leukaemic cells in a mammal which comprises administering a pharmaceutical composition of the present invention to said mammal whereby to deliver an effective amount of a polypeptide conjugated to water soluble polymer, said polypeptide having at least one of the biological properties of naturally occurring G-CSF.

According to a further feature of the present invention there is provided a method for treating osteoporosis or Paget's diesease in a human suffering therefrom which method comprises administering a pharmaceutical composition of the present invention to said human whereby to deliver an effective amount of human calcitonin conjugated to a water soluble polymer.

According to a further feature of the present invention there is provided a method for treating neoplasms or immunodeficiency in a mammal suffering therefrom which method comprises administering a pharmaceutical composition of the present invention to said mammal whereby to deliver an effective amount of interleukin-2 conjugated to a water soluble polymer.

According to a further feature of the present invention there is provided a method for treating a neoplasm or virus in a mammal suffering therefrom which method comprises administering a pharmaceutical composition of the present invention to said mammal whereby to deliver an effective amount of an interferon, (preferably interferon $\alpha$, especially interferon $\alpha_2$) conjugated to a water soluble polymer.

According to a further feature of the present invention there is provided a method for stimulating growth in a human, which method comprises administering to said human a pharmaceutical composition of the present invention, whereby to deliver an effective amount of human growth hormone conjugated to a water soluble polymer.

According to a further feature of the present invention there is provided a process for the production of a pharmaceutical composition of the present invention which comprises dissolving the material of the composition and the physiologically active substance in an organic solvent therefor or uniformly dispersing the material of the composition and the physiologically active substance in an organic or aqueous medium; followed by drying and formulation into a composition suitable for implantation or injection into an animal body.

Such a composition may advantageously be prepared for example by formulation into a solid form suitable for implantation, conveniently a solid cylindrical depot, or may be prepared by formulation into a multiparticulate form suitable for injection for example by comminution or micronisation. The multiparticulate form may be formulated into a solution or emulsion suitable for injection. Formulation may be effected for example in an aqueous medium or in an oil such as arachis oil, or Cremophor (see also Martindale 'The Extra Pharmacopoeia' 28th edition page 694). Vehicles for injection include carboxymethylcellulose (see also Martindale 'The Extra Pharmacopoeia' 28th edition page 947).

Where a dispersion is to be formed, an aqueous medium is preferably employed.

The process may be employed to produce a drug delivery device in the form of a rod, sphere, film or pellet for implantation. The material of the composition may for example be a polylactide (as hereinafter defined) and may advantageously have at least 25%, preferably 40%, molar lactic acid units and up to 75% molar glycolic acid units conveniently in the form of blocks of an average of at least two identical monomer units. The polylactide is preferably either soluble in benzene and has an inherent viscosity (1 g/100 ml solution in benzene) of less than 0.3, or is insoluble in benzene and has an inherent viscosity (1 g/100 ml solution in chloroform or dioxan) of less than 4.

The process of the invention is preferably effected by use of a freeze-dryable common solvent such as for example acetic acid (preferably glacial acetic acid), followed by freezing and then freeze drying. It may be convenient to prepare a first solution of the material of the composition in an organic solvent therefor and a second solution of the physiologically active substance in an organic solvent therefor and then to mix the two solutions. The organic solvent employed is preferably common to the first and second solutions and is advantageously freeze dryable. This process is illustrated in European Patent No 58,481. If desired, however, processing may be via melt processing of an intimate solid mixture of the material of the composition and the physiologically active substance.

According to a further feature of the present invention there is provided a process for the production of a pharmaceutical composition of the present invention wherein the material of the composition comprises polylactide (as hereinafter defined), which may be in the form of a hydrogel, which process comprises incorporating the physiologically active substance into a matrix comprising a polylactide which has at least 25% molar, preferably 40% lactic acid units, and up to 75% molar glycolic acid units., the process further comprising the uniform mixing of the physiologically active substance and the material of the composition by melt processing of an intimate solid mixture of the substance and the material of the composition.

According to a further feature of the present invention there is provided the use of a physiologically active substance which comprises a polypeptide covalently conjugated to a water soluble polymer in the production of a pharmaceutical composition of the present invention.

GENERAL DESCRIPTION

A. Physiologically active substance

In general, the higher the molecular weight of the polypeptide, the larger the number of molecules of water soluble polymer that should be conjugated to the polypeptide in order to provide an optimum release profile. Preferably at least one molecule of water soluble polymer is conjugated to a polypetide of up to 8000 Da molecular weight and at least one molecule of water soluble polymer is employed for every 3000–8000 Da, especially 4000–6500 Da molecular weight of polypeptide. One molecule of polypeptide may carry as many molecules of water soluble polymer as is consistent with retention of the desired level of biological activity. Indeed, subject to this constraint, the polypeptide is advantageously conjugated to the maximum number of water soluble molecules. It will be appreciated that where multiple sites for conjugation of water soluble polymers exist on a given polypeptide, maximal conjugation may result in a heterogeneous mixture of products. Thus for example where a polypeptide has 4 sites for conjugation of water soluble molecules, the maximum ratio of polypeptide to water soluble polymer obtained may be no greater than for example 3.9.

A.1. Polypeptide

The physiologically active substance employed in the pharmaceutical compositions of the present invention may for example comprise human calcitonin, interleukin-2, human growth hormone, or an interferon such as interferon α, for example interferon $\alpha_2$ covalently conjugated to a water soluble polymer or preferably a polypeptide, having at least one of the biological properties of naturally occurring G-CSF and conveniently part or all of the amino acid sequence of naturally occurring G-CSF, covalently conjugated to a water soluble polymer. The peptide will preferably carry no free thiol grouping and thus in respect of polypeptides having at least one of the biological properties of naturally occurring G-CSF the cysteine at position 17 will preferably be absent, or replaced by another amino acid such as alanine or preferably serine, for example.

A.1.1 Polypeptides having at least one of the biological properties of G-CSF

Where it is desired to use a polypeptide having at least one of the biological properties of naturally occurring G-CSF any derivative having such a property may be employed, but advantageously the polypeptide employed is a G-CSF derivative of our European patent Application No. 91303868.3, which describes G-CSF derivatives having improved solution stability. Our European patent application No 91303868.3 describes derivatives of naturally occurring G-CSF having at least one of the biological properties of naturally occurring G-CSF and a solution stability (as herein defined) of at least 35% at 5 mg/ml, the said derivative having at least $Cys^{17}$ of the native sequence replaced by a $Set^{17}$ residue and p of the native sequence replaced by a $Ser^{27}$ residue.

Preferably the derivatives have at least one further modification selected from:

a) $Glu^{11}$ of the native sequence replaced by an $Arg^{11}$ residue;

b) $Leu^{15}$ of the native sequence replaced by a $Glu^{15}$ residue;

c) $Lys^{23}$ of the native sequence replaced by an $Arg^{23}$ residue;

d) $Gly^{26}$ of the native sequence replaced by an $Ala^{26}$ residue;

e) $Gly^{28}$ of the native sequence replaced by an $Ala^{28}$ residue;

f) $Ala^{30}$ of the native sequence replaced by an $Lys^{30}$ or $Arg^{30}$ residue;

g) $Lys^{34}$ of the native sequence replaced by an $Arg^{34}$ g residue;

h) $Lys^{40}$ of the native sequence replaced by an $Arg^{40}$ g residue;

i) $Pro^{44}$ of the native sequence replaced by an $Ala^{44}$ residue;

j) $Leu^{49}$ of the native sequence replaced by a $Lys^{49}$ residue;

k) $Gly^{51}$ of the native sequence replaced by an $Ala^{51}$ residue;

l) $Gly^{55}$ of the native sequence replaced by an $Ala^{55}$ residue;

m) $Trp^{58}$ of the native sequence replaced by a $Lys^{58}$ residue;

n) $Pro^{60}$ of the native sequence replaced by a $Ser^{60}$ residue;

o) $Pro^{65}$ of the native sequence replaced by a $Ser^{65}$ residue;

p) $Pro^{111}$ of the native sequence replaced by a $Glu^{111}$ residue;

q) $Thr^{115}$ of the native sequence replaced by a $Ser^{115}$ residue;

r) $Thr^{116}$ of the native sequence replaced by a $Ser^{116}$ residue; and s) $Tyr^{165}$ of the native sequence replaced by an $Arg^{165}$ residue.

The presence of at least one further modification selected from (b) to (s) is preferred, but the presence of at least one further modification selected from (b), (d), (e), (f), (n) and (o) is particularly preferred of which further modification (o) is especially preferred.

More preferably the further modification comprises at least one of the following:

i) $Gln^{11}$ $Pro^{60,65}$ of the native sequence replaced by $Arg^{11}$, $Ser^{60,65}$.
ii) $Ala^{111}$, $Thr^{115,116}$ of the native sequence replaced by $Glu^{111}$, $Ser^{115,116}$;
iii) $Gln^{11}$, $Trp^{58}$, $Tyr^{165}$ of the native sequence replaced by $Arg^{11,165}$, $Lys^{58}$;
iv) $Leu^{15}$, $Gly^{26,28}$, $Ala^{30}$ of the native sequence replaced by $Glu^{15}$, $Ala^{26,28}$, $Lys^{30}$.
v) $Pro^{44}$, $Leu^{49}$, $Gly^{51,55}$, $Trp^{58}$ of the native sequence replaced by $Lys^{49,58}$, $Ala^{44,51,55}$.

The further modification may also, preferably comprise at least one of the following:
vi) $Leu^{15}$, $Gly^{26,28}$, $Ala^{30}$ of the native sequence replaced by $Glu^{15}$, $Ala^{26,28}$, $Arg^{30}$;
vii) $Pro^{65}$ of the native sequence replaced by $Ser^{65}$;
viii) $Pro^{60,65}$ of the native sequence replaced by $Ser^{60,65}$; or
ix) $Glu^{11}$, $Pro^{65}$ of the native sequence replaced by $Arg^{11}$, $Ser^{65}$.

The above defined modifications may thus, if desired, be introduced into any polypeptide having at least one of the biological properties of naturally occurring G-CSF in order to improve the solution stability of the molecule. The above defined modifications may thus be applied to such polypeptides which differ in amino acid sequence from that specified herein for the naturally occurring G-CSFs in terms of the identity or location of one or more residues (for example substitutions, terminal and internal additions and deletions). As examples such polypeptides might include those which are foreshortened, for example by deletions; or those which are more stable to hydrolysis (and, therefore, may have more pronounced or longer lasting effects than naturally occurring); or which have been altered to delete one or more potential sites for 0-glycosylation (which may result in higher activities for yeast-produced products); or which have one or more cysteine residues deleted or replaced, for example by alanine or serine residues and are potentially more easily isolated in active form from microbial systems; or which have one or more tyrosine residues replaced by phenylalanine and may bind more or less readily to human G-CSF receptors on target cells. The proposed modifications of our above-identified European Patent Application No 91303868.3 may thus, for example be applied to either native G-CSF having of the $Cys^{17}$ native sequence replaced by $Ser^{17}$ or to allelic variants and analogues thereof known to possess at least one of the biological properties of naturally occurring G-CSF such as those described in PCT Patent Publication No WO 87/01132, in European Patent Publication No 243,153, in European Patent Publication No 256,843 in European Patent Publication No 272,603, in Biochemical and Biophysical Research Communications [1989] Vol. 159, No 1, pp 103-111 Kuga T. et al and in U.S. Pat. No 4,904,584.

Such G-CSF derivatives that have been tested have been found to possess improved solution stability over the corresponding unmodified polypeptide with either no significant difference in biological activity or an improved biological activity.

Solution stability is measured herein by determining the percentage of G-CSF derivative remaining in solution in phosphate buffered saline after 14 days at 37° C. given an initial concentration of 1 mg/ml, 5 mg/ml and/or 10 mg/ml. Measurement of solution stability is described in detail hereinafter in Reference Example 26. Conveniently G-CSF derivatives employed in the pharmaceutical compositions of the present invention will have a solution stability at 5 mg/ml of at least 35%, advantageously at least 50% and preferably at least 75%. Preferably the polypeptides of the present invention will have a solution stability at 10 mg/ml of at least 75%, especially at least 85%.

Advantageously the G-CSF derivatives employed in the pharmaceutical compositions of the present invention are selected to possess one of the further modifications (i), (ii), (iii), (iv), (v), (vi), (vii), (viii) or (ix) as hereinbefore defined, preferably one of the further modifications (i), (ii), (iv), (vi), (vii), (viii) or (ix) and especially further modification (ii), (iv), (vi), (vii), (viii) or (ix).

Particularly preferred derivatives for use in the pharmaceutical compositions of the present invention by virtue of their good solution stability include $[Arg^{11}, Ser^{17,27,60,65}]$G-CSF;

$[Glu^{15}, Ser^{17,27}, Ala^{26,28}, Lys^{30}]$G-CSF;

$[Arg^{11}, Glu^{15}, Ser^{17,27,60,65}, Ala^{26,28}, Lys^{30}]$G-CSF $[Arg^{11,23}, Ser^{17,27,60,65}]$G-CSF $[Arg^{11,34}, Ser^{17,27,60,65}]$G-CSF $[Arg^{11,40}, Ser^{17,27,60,65}]$G-CSF $[Ala^1, Thr^3, Tyr^4, Arg^{5,11}, Ser^{17,27,60,65}]$G-CSF $[Arg^{11}, Glu^{15,111}, Ser^{17,27,60,65,115,116}, Ala^{26,28}, Lys^{30}]$G-CSF $[Arg^{11,165}, Glu^{15}, Ser^{17,27,60,65}, Ala^{26,28}, Lys^{30,49,58}]$G-CSF $[Arg^{11}, Glu^{15}, Ser^{17,27,60,65}, Ala^{26,28,44,51,55}, Lys^{30,49,58}]$G-CSF $[Arg^{11,165}, Glu^{15,111}, Ser^{17,27,60,65,115,116}, Ala^{26,28,44,51,55}, Lys^{30,49,58}]$G-CSF $[Glu^{15}, Ser^{17,27}, Ala^{26,28}, Arg^{30}]$hu G-CSF

Especially preferred G-CSF derivatives for use in the pharmaceutical compositions of the invention by virtue of their excellent solution stability and good specific activity include:
i) $[Arg^{11}, Ser^{17,27,60,65}]$G-CSF,
ii) $[Glu^{15}, Ser^{17,27}, Ala^{26,28}, Lys^{30}]$G-CSF,
iii) $[Arg^{11}, Glu^{15}, Ser^{17,27,60,65}, Ala^{26,28}, Lys^{30}]$G-CSF,
iv) $[Arg^{11,40}, Ser^{17,27,60,65}]$G-CSF,
v) $[Arg^{11,23}, Ser^{17,27,60,65}]$G-CSF,
vi) $[Arg^{11,165}, Glu^{15}, Ser^{17,27,60,65}, Ala^{26,28}, Lys^{30,58}]$G-CSF
vii) $[Arg^{11}, Glu^{15,111}, Ser^{17,27,60,65,115,116}, Ala^{26,28}, Lys^{30}]$G-CSF,
viii) $[Glu^{15}, Ser^{17,27}, Ala^{26,28}, Arg^{30}]$G-CSF, and
ix) $[Ala^1, Thr^3, Tyr^4, Arg^{5,11}, Ser^{17,27,60,65}]$G-CSF
x) $[Ser^{17,27,60,65}]$G-CSF
xi) $[Arg^{11}, Ser^{17,27,65}]$G-CSF, and
xii) $[Ser^{17,27,65}]$G-CSF
of which (i), (ii), (iii), (vi), (vii), (viii), (x), (xi) and (xii) are most preferred.

These latter human G-CSF derivatives show not only excellent solution stability properties, but also possess improved specific activity over naturally occurring human G-CSF.

A presequence methionine may be either present or absent in the polypeptides of the present invention but is conveniently present.

With regard to the preparation of G-CSF derivatives for use in the pharmaceutical compositions of the present invention, it has been found advantageous to employ a production vector based on pAT153, comprising:

i) a promoter and where appropriate an operator therefor, for example a trp promoter or a T7A3 promoter. The T7A3 promoter is the A3 promoter of bacteriophage T7 [see Dunn J. J. and Studier F. W. J. Mol. Biol. 166, 477–535 (1983)]. The complete nucleotide sequence of bacteriophage T7 DNA and the locations of T7 genetic elements are set out in this reference;
ii) a ribosome binding site sequence, for example a trp leader ribosome binding site sequence;
iii) a cloning site for the gene to be expressed;
iv) a T4 transcription termination sequence (see SEQ ID No. 51 and FIG. 4)
v) a cer sequence (Summers D. et al MGG, 201, p334–338, 1985)
vi) a tetracycline repressor gene (Tet R)
vii) tetracycline resistance gene (Tet A)
viii) multiple restriction enzyme recognition sequences SEQ ID No 47. sets out a sequence which includes an EcoRI restriction endonuclease site (nucleotides 1–6), the A3 promoter sequence (nucleotides 7–52), the trp leader ribosome binding site sequence (nucleotides 53–78) and the translation initiation codon (nucleotides 79–81)

It may be advantageous to cultivate the host capable of expressing a G-CSF derivative (as hereinbefore defined) of the invention, in a growth medium and adding a supplement which includes yeast extract to the growth medium during cultivation. It is preferable that addition of the supplement which includes yeast extract is initiated at a predetermined time after the start of cultivation. The rate of addition of the supplement which comprises yeast extract is preferably such that the growth medium does not become exhausted of yeast extract. This is particularly advantageous where the production vector is used with a T7A3 promoter.

It may also be advantageous to cultivate a host, transformed with a recombinant vector carrying genetic material coding for a G-CSF derivative as hereinbefore defined in the presence of leucine and/or threonine in an amount sufficient to give improved accumulation of the G-CSF derivative. Thus it is particularly advantageous to effect the fermentation in the presence of leucine where the production vector is used with the trp promoter.

Purification of the G-CSF derivative could be effected as described in PCT Patent Publication No WO 87/01132, but there is no reference therein to the removal of detergent, particularly N-lauroyl sarcosine in salt form (for example Sarkosyl) from the G-CSF analogues prepared in this PCT Publication. Detergent removal is preferably effected in the presence of a phosphate buffered saline (pH 7.2–7.5). The phosphate buffered saline may conveniently be prepared from isotonic saline and may thus for example have a composition as described in Reference Example 3. In this regard it was found that other buffers were less preferred since either detergent removal, particularly N-lauroyl sarcosine (in salt form) removal, was slower or more protein precipitated out. It is further preferred to effect detergent removal by diafiltration since this was found to improve efficiency without provoking increased protein precipitation. For example diafiltration was found to be preferable to conventional diffusion dialysis. Furthermore it was found that detergent concentration, particularly N-lauroyl sarcosine in salt form (e.g. Sarkosyl) concentration, could be reduced below 1% whilst retaining resolution during chromatography. A reduction in initial detergent concentration assists detergent removal and thus it is preferred to use the minimum concentration of detergent, for example N-lauroyl sarcosine (in salt form e.g. Sarkosyl), consistent with retaining resolution during chromatography. A particular concentration of detergent, for example N-lauroyl sarcosine (in salt form) e.g. Sarkosyl, is thus from 0.8% to 0.2%, preferably from 0.5 to 0.2%, especially about 0.3%.

In addition to the above it was found that the removal of detergent such as N-lauroyl sarcosine (in salt form) e.g. Sarkosyl activates a trace of proteolytic activity which may complicate product evaluation. It has further been found that this proteolytic activity may be significantly reduced and even eliminated if, after detergent removal by diafiltration, the pH is reduced to below 7.0 before substantial proteolysis, conveniently by diafiltration and preferably by dialysis. Thus the reduction or removal of trace proteolytic activity may be effected at a pH that is below 7.0 but which is sufficiently high to avoid significant hydrolysis of the polypeptide. The pH is advantageously in the range 6.0 to 4.5, preferably 5.8 to 5.0 especially about 5.4. A further advantage of this embodiment is that E.coli contaminants and/or degraded or incorrectly folded protein can be precipitated by effecting this lowering of pH. It is preferred that purification include the step of size exclusion chromatography since otherwise the problem of proteolytic degradation is increased and whilst the present embodiment will reduce such degradation it makes it difficult to eliminate.

In addition to the above processes, the introduction of solution stability into a G-CSF or derivative thereof enables substantial simplification of the process of extraction. Thus a process for extracting an active derivative of the invention (as hereinbefore defined) from an inclusion body thereof comprises 1) suspending said inclusion body in a detergent, particularly N-lauroyl sarcosine in salt form (e.g. Sarkosyl) 2) oxidation, 3) removal of detergent for example as hereinbefore described and 4) maintaining solution obtained following removal of detergent at an elevated temperature for example 30°–45° C., advantageously 34°–42° C. whereby to precipitate contaminating bacterial protein, product oligomers and/or degradation products. The said solution is conveniently maintained at said elevated temperature for from 6–24 hours, advantageously 8–18 hours preferably 10–14 hours, especially about 12 hours.

The extraction process may for example be effected by lysing host cells followed by centrifugation to obtain the inclusion body for example in the form of a pellet. The inclusion body may then be suspended in a detergent such as, for example N-lauroyl sarcosine in salt form (e.g. Sarkosyl), preferably 1–3%, especially about 2% N-lauroyl sarcosine in salt form (e.g. Sarkosyl). Suspension in detergent may be followed by oxidation, for example in the presence of copper sulphate (CuSO$_4$) which in turn may be followed by centrifugation.

Where it is possible to wash the inclusion body it is preferred to use urea rather than for example deoxycholate.

The extraction process enables the production process to be simplified for example by elimination of the need for the use of size exclusion columns. Moreover the high recovery of product from the heat treatment step appears to be one of the advantages of the increased solution stability of the G-CSF derivatives as hereinbefore defined. Indeed the greater the solution stability the more suited is the protein to the new extraction process. Thus for example it is preferred to apply this extraction process to the extraction of the G-CSF derivatives having a solution stability of at least 85% at 10 mg/ml. When the known analogue [Met$^{-1}$, Ser$^{17}$] G-CSF was extracted by the above process, rpHPLC indicated that only 40% of the desired product remained in solution after heat treatment of a retentate containing 1 mg/ml total protein. At 3 mg/ml total protein, only 19% of the analogue remained in solution.

A.1.2 Other polypeptides

Human calcitonin is described in U.K. Patent specification No. 1,270,595 and may be prepared for example by peptide synthesis or by recombinant techniques [see for example European Patent Publications Nos 77,689; 70,675; 95,351; 197,794; 201,511 and 308067 and U.S. Pat. Nos. 3,891,614 and 3,926,938]. Production of human calcitonin covalently conjugated to water soluble polymer by peptide synthesis may be preferable in view of the availability of a free N-terminal amino group as well as a further free amino group on the single lysine residue for covalent conjugation of water soluble polymer. Formation of human calcitonin by either peptide synthesis or recombinant techniques prior to conjugation with water soluble polymer may result in a heterogeneous mixture of products. If, however the desired relevant amino acid residue(s) is (are) covalently conjugated to water soluble polymer prior to incorporation in the total peptide synthesis a single molecular entity may be formed as product rather than a heterogeneous mixture. If desired however, the human calcitonin may of course be prepared by either peptide synthesis or recombinant techniques and the human calcitonin thus formed thereafter covalently conjugated to the water soluble polymer.

Interleukin-2 is a soluble immunoenhancing glycoprotein produced by T-lymphocytes following activation by antigens or mitogens in the presence of interleukin-1. Interleukin-2 induces T-cell growth and proliferation, potentiates the release of γ-interferon, B-cell growth factor and B-cell differentiation factor, enhances natural killer cell activity and restores T-cell function in immunodeficient disease states. The isolation of the human IL-2 gene has been described by S. Mita et al, Biochem, Biophys, Res. Commun. 117, 114 (1983) and the microbial production of interleukin-2 has been described for example in European Publication No 142,268. Moreover various analogues of interleukin-2 such as des-alanyl Ser$^{125}$ IL-2 have also been described for example in U.S. Pat. Nos 4,518,584 and 4,530,787. The conjugation of a polypeptide having IL-2 activity, such as des-alanyl Ser$^{125}$ IL-2, to polyethylene glycol has also been described in PCT Patent Publication WO 87/00056. Peptides possessing interleukin-2 activity such as IL-2 per se and its analogues as well as such peptides covalently conjugated to water soluble polymer such as polyethylene glycol are of potential interest in the treatment of cancer.

Human growth hormone (HGH) is a species specific anabolic protein that promotes somatic growth, stimulates protein synthesis, regulates carbohydate and lipid metabolism and increases serum levels of somatomedins. The amino acid sequence of HGH and the cloning and expression of DNA for HGH in bacteria is described in D V Goeddel et al, Nature 281, 544 (1979) and in Belgian Patent No 884,012 and in U.S. Pat. No 4,342,832. The cloning and expression of DNA for HGH in mammalian cells is described by G. N. Pavakis et al in Proc. Natl. Acad, Sci, USA 78. 7398 (1981) and in French Patent No 2,534,273.

It will be appreciated that HGH contains two species of protein, one with a molecular mass of 22kDa and another of 20kDa (see U J Lewis et al, J Biol Chem 253, 2679–2687 (1978) and R N P Singh and U J Lewis, Prep. Biochem. 11 559–570 (1981)). The 20kDa variant form of growth hormone (20K-HGH) constitues 5–10% of the total HGH in human anterior pituitary gland, plasma and urine. Amino acid sequence analysis shows that 20K-HGH varies from 22K-HGH only in that it lacks the sequence of amino acids 32–46. The 20K-HGH form possesses comparable growth promoting and other biological activities, but shows no or less insulin-like activity. The molecular cloning of DNA encoding the 20K-HGH variant is described in Biochimica et Biophysica Acta 949 (1988) 125–131 by N Masuda et al.

Interferon is the name given to a family of species specific vertebrate proteins that confer non-specific resistance to a broad range of viral infections, affect cell proliferation and modulate immune responses. The interferons have been widely described in the literature [see for example C. Weissmann, H. Weber, Prog. Nucl. Acid. Res. Mol. Biol. 33, 251–300 (1986) and K C Zoon, Interferon 9, 1–12 (1987)]. The 3 major components of the interferon family are designated α-, β- and γ- and have been identified based on their antigenic and physicochemical properties, the nature of their inducers and the cellular source from which they are derived (Nature 286, 110 (1980). The interferons may be prepared by any desired technique such as for example by recombinant DNA technology. The production of interferon α has been described by S. Nagata et al, Nature 284, 316 (1980) and by D V Goeddel et al, Nature 287, 411 (1980), but a particularly good description of the production of interferon α$_2$ is by M D Edge et al, Nucleic Acids Research Vol 11 , No 18, 6419–6435 (1983). The recombinant production of interferon-β has been described by T. Taniguchi et al., Proc. Natl, Acad. Sci. USA 77, 5230 (1980) and by R Derynck et al, Nature 285, 542 (1980). The recombinant production of interferon-γ has been described by P W Gray et al, Nature 295, 503 (1982) and the structure of the human interferon-γ gene has been described by P W Gray and D V Goeddel, Nature 298, 859, 1982. Interferons are further discussed in Biotechnology and Genetic Engineering Reviews Vol 2 p 215(1984) by M D Edge and R Camble.

It should be appreciated that at least certain interferons may be labile about pH 8.5.

The interferon employed is advantageously interferon α or interferon β, preferably interferon α and especially interferon α$_2$.

In general peptides for use in the present invention may be produced by recombinant techniques or by peptide synthesis. Peptide synthesis may be a preferred preparative technique where the size of the peptide permits and where more than one free amino group (for example the N-terminal amino group and one or more lysine residues) is present for covalent conjugation with a water soluble polymer as exemplified above. Such a preparative technique has the advantage that lysine residues covalently conjugated to water soluble polymer may be introduced at specific sites in the molecule to form a single molecular entity rather than the heterogeneous mixture of products that may result from covalent conjugation of water soluble polymer to a peptide having multiple free amino groups.

Regardless of the preparative technique employed it may be advantageous to modify the peptide i) by substituting existing residues for other residues, such as lysine residues, for attachment of water soluble polymer molecules, ii) by the addition of new such residues for attachment of water soluble polymer molecules for example at the N- and/or C- terminus or elsewhere in the molecule provided activity is not destroyed or unacceptably reduced and/or iii) by substituting or removing one or more such residues, for example lysine residues, to reduce the degree of attachment of water soluble polymer molecules whereby to decrease the heterogeneous nature of the product and/or to avoid attachment of water soluble polymer at sites in the molecule where such attachment would reduce or destroy the activity of the peptide.

Covalent conjugation of water soluble polymer molecules such as polyethylene glycol to formed peptide or to specific amino acids prior to peptide formation may be effected by any convenient means such as by methods described herein.

A.2 Water soluble polymer

The water soluble polymer covalently conjugated to the polypeptide may for example be a dextran or poly(N-vinyl pyrrolidone), but is preferably selected from polyethylene glycol, polypropylene glycol homopolymers, polyoxyethylated polyols and polyvinyl alcohol, wherein the said homopolymer is unsubstituted or substituted at one end with an alkyl group.

Particular polymers to which the polypeptide is attached include a homopolymer of polyethylene glycol (PEG) or a polyoxyethylated polyol, provided that the polymer is soluble in water at room temperature. Examples of polyoxyethylated polyols include, for example, polyoxyethylated glycerol, polyoxyethylated sorbitol or polyoxyethylated glucose.

The glycerol backbone of polyoxyethylated glycerol is the same backbone occurring naturally in, for example, animals and humans in mono-, di-, and triglycerides. Therefore, this branching would not necessarily be seen as a foreign agent in the body.

Preferably the polymer is unsubstituted polyethylene glycol (PEG), monomethyl PEG (mPEG), or polyoxyethylated glycerol (POG), especially monomethyl PEG (mPEG) and it is conveniently coupled to the polypeptide via an amide or urethane linkage formed for example from the 4-hydroxy-3-nitrobenzene sulfonate ester or the N-hydroxysuccinimide ester of a PEG, mPEG, or POG carboxylic acid or from the p-nitrophenylcarbonate or 2,4,5-trichlorophenylcarbonate of a PEG, mPEG or POG. If desired the polypeptide may be linked to mPEG via an amino acid or peptide as a spacer arm (see L. Sartore et al in Appl. Biochem. Biotechnol. 27 45-54 (1991)).

It is preferred that the molecular weight of the polymer be between about 300 and 100,000, more preferably between 350 and 40,000, depending, for example, on the particular polypeptide employed. In this regard the molecular weight quoted in relation to the water soluble polymers are number average molecular weights, but since such polymers should have a polydispersity (as hereinafter defined) of about 1 the number average molecular weight will approximate to the weight average molecular weight.

The PEG homopolymer may be unsubstituted, but it may also be substituted at one end with an alkyl group. Preferably the alkyl group is a $C_1$–$C_4$ alkyl group, and most preferably a methyl group. Advantageously the polymer is an unsubstituted homopolymer of PEG, a monomethyl-substituted homopolymer of PEG or polyoxyethylated glycerol, and has a lower molecular weight limit of preferably 1000, more preferably 1250 and especially 1500 and an upper molecular weight limit of for example 20,000. The upper molecular weight limit may if desired be as high as 40,000, but is advantageously 15,000 and preferably 10,000. Preferably the molecular weight is in the range 1000 to 15,000, for example 2000 to 10,000, especially 2000 to 5000.

Where the polypeptide has at least one of the biological properties of naturally occurring G-CSF and an unsubstituted homopolymer of PEG or a monomethyl-substituted homopolymer of PEG is used as the water-soluble polymer, the lower molecular weight of the water soluble polymer may be as low as 750 but will normally be 1000, advantageously 1250, preferably 1500 and especially about 2000.

The polypeptide will be covalently conjugated to a water soluble polymer such as polyethylene glycol, polypropylene glycol homopolymers, polyoxyethylated polyols and polyvinyl alcohol wherein the said homopolymer is unsubstituted or substituted at one end with an alkyl group.

Polypeptides described above may, for example, be conjugated to the polymer via either (1) free amino group(s), (2) at least one carbohydrate moiety on the protein, or (3) free sulfhydryl group(s) that is/are either present in the native molecule or is/are engineered into the molecule.

Such techniques are described in detail in PCT Patent Publication WO 89/06546 in relation to M-CSF.

In particular the present invention provides a method for preparing a G-CSF polypeptide (as herein defined) covalently conjugated to a polyethylene glycol or a G-CSF polypeptide covalently conjugated to a polyoxyethylated polyol which comprises contacting an excess of an activated ester or carbonate of polyethylene glycol (PEG) or polyoxyethylated polyol (POP) with a G-CSF polypeptide as herein defined whereby to form a G-CSF polypeptide substantially maximally covalently conjugated to PEG or POP. The activated carbonate of PEG or the activated carbonate of POP is preferably prepared by contacting PEG or POP, which has at least one hydroxyl group, and a chloroformate whereby to form the said activated carbonate.

Preferably the molar ratio of PEG or POP active ester or carbonate to G-CSF polypeptide is from 200:1 to 50:1, more preferably 150:1 to 50:1 especially about 100:1.

The process employed is similar to that disclosed in Applied Biochem and Biotech., 11:141-152 (1985) by Veronese et al and subsequently applied by Cetus Corporation to IL-2 and claimed in their U.S. Pat. No 4,902,502 (filed Jan. 23, 1989).

Where conjugation of water soluble polymer to polypeptide reduces the physiological activity of the conjugate below a desired level, this may, for example, be overcome by 1) employing a cleavable linkage between the polypeptide and the water soluble polymer so that following release of the conjugate in vivo the water soluble polymer is cleaved from the polypeptide to yield polypeptide of good physiological activity; or 2) tailoring the molecule of the polypeptide (for example as described in U.S. Pat. No 4,904,584) such that conjugation of water soluble polymer occurs at sites on the polypeptide that do not significantly adversely affect the physiological activity of the conjugate. If desired however a reduction in physiological activity of the polypeptide may simply be overcome or at least minimised by increasing the quantity of conjugate present in the pharmaceutical composition of the present invention.

B. Material of the composition

The material of the composition may be of any convenient type of polymer or mixture thereof such as polylactide (as hereinafter defined) or biodegradable hydrogels derived from amphipathic block copolymers (for example as described in European Patent No 92,918) and mixtures of polylactides and such hydrogels. Hydrogels can have a particular utility as these can be designed such that a component of the linear or branched block copolymer has a thermodynamic identity similar to that of the hydrophilic unit (water soluble polymer) attached to the polypeptide. Thus, for example, it may be particularly useful to employ pegylated polypeptides with amphipaths containing polyethylene glycol.

The material of the composition may thus for example be polylactide (as hereinafter defined) for example as described in European Patent Publication No 58,481.

The release of macromolecular drugs from polylactides is dependent on the structure of the polylactide (that is the distribution and length of co-monomer units in co-polymers of lactic acid/glycolic acid), the molecular weight of homo- and co-polymers of lactic acid/glycolic acid and the molecular weight distribution or polydispersity of said homo- and co-polymers. Consequently the preferred (but not limiting) polylactides are those which are insoluble in benzene and have an inherent viscosity at 1% w/v in chloroform at 25° C. of more than 0.09 dl/g but less than 4 dl/g or are soluble in benzene and have an inherent viscosity at 1% w/v chloroform of more than 0.09 dl/g but less than 0.5 dl/g and more preferably less than 0.3 dl/g. Another preferred class of polylactides are those which have a number average molecular weight of more than 2000 and which have controlled polydispersities such that for number average molecular weights of 2000 to 10000 the polydispersities range from 1.2 to 50 and for number average molecular weights of 5000 to 30000 the polydispersities range from 1.4 to 15. The preferred number average molecular weight range is 2000 to 20,000. The solution viscosity properties and their measurement and the measurement of molecular weights are described in 'Preparative Methods of Polymer Chemistry', 2nd Edition, pages 43 to 52, W. R. Sorenson and Tod W. Campbell, 1968, Interscience Publishers. These various properties of the polymer determine the degradation profiles of the polylactides alone as well as pharmaceutical compositions based on them. The degradation profiles include generation of microporosity in the degrading polylactide, water uptake by the degrading polylactide and ultimately erosion or weight loss from the degrading polylactide. In this regard diffusion of a physiologically active substance through polymer alone is a function of solubility/compatibility of the physiologically active substance with the rate controlling polymer as well as the molecular size of the physiologically active substance. For either or both of these reasons a physiologically active substance (as hereinbefore defined) may not be able to diffuse through the polymer phase. In such a situation release would have to occur by some other mechanism such as through aqueous pores in the polymer matrix. It may therefore be desirable to design polymers which will have a continuous water uptake with time and this continuous water uptake is associated with the generation of aqueous micropores in the degrading matrix which ultimately degrades to soluble fragments and erodes.

Whilst we do not wish to be bound by theoretical considerations we believe that covalent conjugation of polypeptide with a water soluble polymer particularly polyoxyethylene polymers to form a physiologically active substance (as hereinbefore defined) advantageously affects the percolation threshold (as hereinbefore defined) of a continuous release pharmaceutical composition. The percolation threshold is a function of level of incorporation in, and compatibility of the physiologically active substance with, the polymer matrix in the anhydrous composition as well as the nature and degree of phase separation on hydration of the composition. The chain length of the polypeptide, the molecular weight of the water soluble polymer and the level of incorporation of water soluble polymer are all features which affect compatibility of the physiologically active substances.

If desired the continuous release pharmaceutical compositions of the present invention may have a brief induction period before release of physiologically active substance commences. The length of this induction period may vary depending on the quantity of physiologically active substance to be released and the period over which it is designed to be released.

The continuous release pharmaceutical compositions of the present invention are preferably in other than microcapsule form, for example microspheres where the physiologically active substance is dispersed throughout the polymer up to and including the surface or other microparticulate forms wherein physiologically active substance extends up to the surface.

The continuous release compositions of the invention may be placed in the body of an animal (such as a human) which it is desired to treat with a polypeptide by, for example, intramuscular or subcutaneous injection or by sub-dermal surgical implantation, in conventional clinical or veterinary manner.

B.1 Process for preparation of continuous release pharmaceutical composition

The continuous release pharmaceutical compositions of the present invention may be prepared by any convenient process. Thus for example the material of the composition, for example as defined above, may be presented as a solution in an organic solvent such as glacial acetic acid in which the physiologically active substance as hereinbefore defined may be dissolved, for example as described in European Patent No 58,481.

B.2 Aqueous process

The continuous release pharmaceutical compositions of the present invention may also for example be prepared by the production of an aqueous dispersion of a polymer or copolymer having one or more carboxylic acid end groups, characterized in that the polymer or copolymer has a weight average molecular weight of at least about 3000 and is in the form of an ammonium or alkali metal salt thereof, and that at least 80% by weight of the solids content of the dispersion is capable of passing through a bacterial filter of $200m^{-9}$ pore size.

The production of such an aqueous dispersion may be effected by mixing a solution of the polymer or copolymer in a water-miscible organic solvent, and at least a stoichiometric amount of a solution of a water-soluble ammonium or alkali metal salt or hydroxide to form a dispersion of the corresponding ammonium or alkali metal salt of the polymer or copolymer in a mixed aqueous/organic solvent at essentially neutral pH, and then evaporating the water-miscible organic solvent to produce an aqueous dispersion of the polymer or copolymer salt, of which at least 80% by weight of the solids content is capable of passing through a bacterial filter of $200 m^{-9}$ pore size.

The polymer or copolymer used in the above process may, for example, be selected from the homopolymers poly(D-, L- and DL-lactic acid), poly(D-, L- and DL-lactide), polyglycolic acid, polyglycolide, poly-E-caprolactone and poly(hydroxybutyric acid); copolymers derived from two or more of the monomers from which these homopolymers are derived; graft or branched block copolymers comprising one of these homopolymers or copolymers and a hydrophilic polymer selected from poly(vinyl alcohol), poly(vinylpyrrolidone), poly(ethylene oxide), poly(ethylene glycol), polyacrylamide, polymethacrylamide, dextran, alginic acid, sodium alginate, gelatin, or a copolymer of any two or more of the monomers from which these are derived.

Preferred polymers or copolymers for use in this aqueous process are the homopolymers poly(D-, L- and DL-lactic acid) and poly(D-, L- and DL-lactide, and the copolymers poly(D-, L- or DL-lactic acid-co-glycolic acid) and poly(D-, L- or DL-lactide-co-glycolide).

A preferred water-miscible solvent for use in this aqueous process is acetone, 2-butanone (methyl ethyl ketone), dioxan, hexafluoroisopropanol, tetrahydrofuran, methanol or ethanol, and particularly acetone; and a preferred water-soluble ammonium or alkali metal salt or hydroxide is sodium, potassium or ammonium bicarbonate, sodium, potassium or ammonium carbonate, or sodium, potassium or ammonium hydroxide.

An alternative solvent for use in this aqueous process is a water-immiscible solvent such as dichloromethane. Such a solvent results in an aqueous dispersion of copolymer salt of larger particle size.

The solution of the water-soluble ammonium or alkali metal salt or hydroxide may be a solution in water, or in a mixture of water and a water-miscible organic solvent, for example methanol or ethanol.

The evaporation of the water-miscible solvent is preferably carried out under reduced pressure, and at a temperature as little above ambient temperature as possible.

If the polymer or copolymer solution in an organic solvent is added to the aqueous phase, and this addition is completed before the organic solvent is evaporated, high yields of particles capable of passing a $200 m^{-9}$ filter are only obtained if the concentration of the polymer or copolymer in the organic solvent does not exceed about 1.5% weight to volume.

In this process, the mixing of the solution of the polymer or copolymer in a water-miscible organic solvent with the solution of a water-soluble ammonium or alkali metal salt or hydroxide is preferably carried out under high-shear stirring, for example with a Ystral homogenizer capable of providing stirring at up to 25,000 rpm (revolutions per minute), or similar apparatus.

Preferably, solubilising protein such as foetal calf serum (FCS) and human serum albumin (HSA) will be absent from the pharmaceutical composition.

In preparing the pharmaceutical compositions of the present invention the preferred parameters for a given composition may be determined by trial and error based on the above detailed discussion as a guideline. In respect of certain polypeptides, such as interleukin-2 (IL-2), human growth hormone (HGH) and interferon$\alpha_2$ (IFN$\alpha_2$) one parameter that may be altered with advantage to achieve the desired release profile is the protein loading of the composition which in the case of IL-2, HGH and IFN$\alpha_2$ will normally be between 5 and 20% by weight, preferably 10 to 18%, especially about 12.5–16% by weight.

It should be emphasised that workers with water soluble polymers such as polyethylene glycol have hitherto found it necessary to restrict the extent of modification of the desired polypeptide if high physiological activity is to be retained. Thus the conjugation of a water soluble polymer, in excess, with a physiologically active polypeptide has hitherto resulted in a substantial reduction in, or complete loss of, physiological activity. The need to restrict the extent of modification of the polypeptide results in an increase in the heterogeneous distribution of a given number of water soluble polymer molecules around a number, commonly a large number, of potential sites for modification. Such a high degree of heterogeneity may have little effect on such parameters as solubility and half life, but may be disadvantageous for controlled and complete release from a continuous release pharmaceutical composition since a heterogeneous population of isomers may decrease the consistency and completeness of release from the composition. Surprisingly, it has been found that G-CSF derivatives of our European Patent Application No. 91303868.3 and especially [Arg$^{11}$, Ser$^{17,27,60,65}$] G-CSF (either with or without a presequence methionine, but conveniently with such a presequence methionine) may be subjected to exhaustive modification with a water soluble polymer such as described above especially a polyethylene glycol (PEG) such as monomethyl-polyethylene glycol (mPEG) whilst retaining at least one of the biological properties of naturally occurring G-CSF to a significant degree. Thus, for example, pegylated G-CSF derivatives that have been tested have been found to retain the G-CSF activity of native G-CSF within a factor of about 2 in vitro. Indeed dose response curves obtained in respect of in vivo studies with pegylated [Arg$^{11}$, Ser$^{17,27,60,65}$]G-CSF show an activity about double the activity of native G-CSF. Such exhaustive modification results in a substantially less heterogeneous population of isomers which in a continuous release pharmaceutical composition substantially increases the consistency and completeness of release from such compositions.

Thus the most preferred physiologically active substance for use in the pharmaceutical composition of the present invention is pegylated [Arg$^{11}$, Ser$^{17,27,60,65}$]human G-CSF in which a presequence methionine may be either present or absent, but is conveniently present, in the G-CSF moiety and in which each polyethylene glycol (PEG) moiety has a molecular weight of 2000–5000Da., the ratio of G-CSF moiety to PEG moieties being from 1:3–1:4 especially about 1:3.9.

Glossary of terms

The following glossary of terms used in the present specification is provided to assist the reader:

The term "an aqueous physiological-type environment" means the body of a warm-blooded animal, particularly the musculature of subcutaneous tissue or the circulatory system of such an animal, or aqueous liquids that mimic such an environment. Such aqueous liquids may optionally be buffered to a physiological pH, at a temperature of between 35 and 40° C. and may for example be used in laboratory investigations.

The term "continuous release" is used in this specification solely to define a release profile which is essentially monophasic, although it may have a point of inflection, but certainly has no "plateau" phase, when cumulative release of physiologically active substance is plotted as a function of time.

The term "monophasic" as used herein means release continuously over a time interval during which there may be a point of inflection, but certainly no plateau phase, when cumulative release of physiologically active substance is plotted as a function of time.

The term "polylactide" is used in a generic sense to include polymers of lactic acid alone, copolymers of lactic acid and glycolic acid, mixtures of such polymers, mixtures of such copolymers, and mixtures of such polymers and copolymers, the lactic acid being either in racemic or in optically active form.

The term "acid-stable" is to be understood as meaning that the physiologically active substance is stable under the conditions encountered within the claimed formulation during the period of use envisaged. The pH within the claimed formulation will vary but will generally be no greater than pH8 and will not normally be less than pH2. These pH values generally represent extremes and the pH within a given formulation may well never be less than pH 2.5 or pH3. The relevant temperature will normally be mammalian body temperature, generally up to about 40° C. The period of use envisaged may vary from for example 1 week to 6 months.

The term "polydispersity" is defined as the Mw/Mn where Mw is the weight average molecular weight and Mn is the number average molecular weight. Absolute measurement of number average molecular weight can be measured by end group analysis or by vapour pressure osmometry. Measurement of number and weight average molecular weights as well as polydispersity may also be effected by size exclusion chromatography relative to polystyrene standards.

The term "percolation threshold" is used herein to define the state achieved when aqueous drug (physiologically active substance as hereinbefore defined) phase achieves continuity with the external environment and with other domains of aqueous drug (physiologically active substance as hereinbefore defined) within the continuous release pharmaceutical composition of the present invention.

The term "naturally occurring G-CSF" as used herein refers to those G-CSFs that have been found to exist in nature and includes the two polypeptides having the amino acid sequence set out in SEQ ID No 43 (as hereinafter defined). These two polypeptides differ only in so far as a tripepride insert Val-Ser-Glu is present in one polypeptide between positions 35 and 36, but absent in the other. The numbering system used throughout the present specification is based on the naturally occurring polypeptide without the Val-Ser-Glu insert and the term "native" as used herein also refers to this polypeptide without Val Ser Glu insert. It will be appreciated that the modifications described herein are applicable to all naturally occurring forms of G-CSF and analogues thereof as described above and consequential revision of the position numbers of the polypeptide may be necessary depending on the form of naturally occurring G-CSF selected for modification.

The term "having at least one of the biological properties of naturally occurring G-CSF" as applied to a polypeptide means that the polypeptide is active in at least one of the biological asays detailed in U.S. Pat. No. 4,810,643 at col. 20, line 21 through col. 24, line 48, and FIG. 9.

The term 'solution stability' means the decreased tendency of a substance to precipitate from solution under physiological conditions of pH, temperature and ionic strength. The property of solution stability is thus different from that of solubility.

BRIEF DESCRIPTION OF THE DRAWINGS

FIG. 1 (SEQ ID NO:44 and SEQ ID NO:57) shows the nucleotide sequence of the 167 bp fragment referred to in Reference Example 5;

FIG. 2 shows the amino acid sequence and corresponding nucleotide sequence of native human (hu) G-CSF and restriction sites;

FIG. 3 shows the amino acid sequence and corresponding nucleotide sequence of [Ser17,27]hu G-CSF (SEQ ID NO:46) and restriction sites.

FIG. 4A shows the nucleotide sequence of the T4 transcription terminator having (a) terminal SalI and HindIII restriction sites (SEQ ID NO:48 and SEQ ID NO:48); and (b) terminal SalI and StyI restriction sites (SEQ ID NO:49 and SEQ ID NO:59);

FIG. 6 shows the nucleotide sequence of the EcoRI-SalI fragment referred to in Reference Example 6(b) but omitting the inteferon $\alpha_2$ gene sequence;

Figure 5:
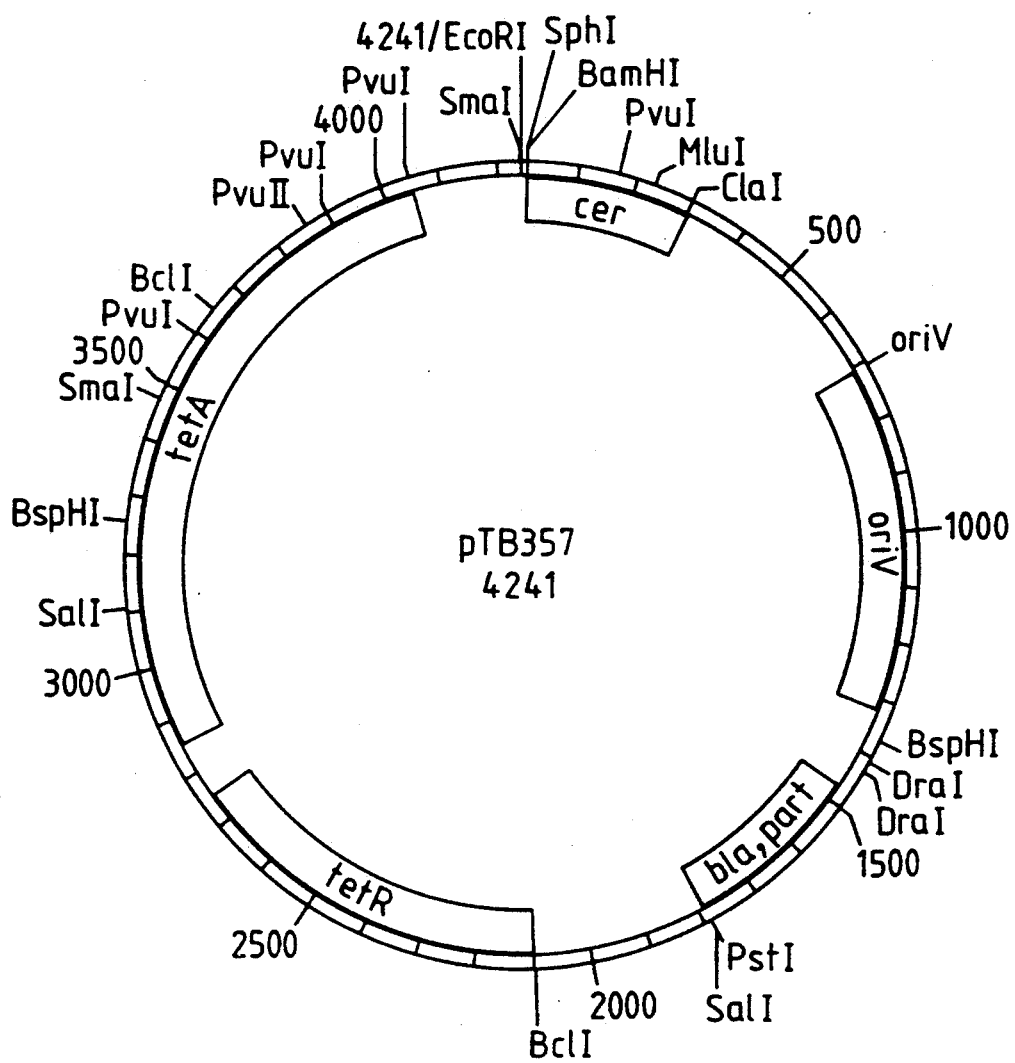
FIG. 5 shows a restriction map of pTB357 (also referred to herein as pLB004)

The following materials are referenced to hereinafter in the Reference Examples and Examples and their constitution is as follows:

BUFFERS FOR RESTRICTION ENZYMES
Stability: stable at −20° C.
Buffer composition:

| Buffer components | Final concentration in mmol/l (1:10 diluted set buffer) | | | | |
|---|---|---|---|---|---|
| | A | B | L | M | H |
| Tris acetate | 33 | — | — | — | — |
| Tris-HCl | — | 10 | 10 | 10 | 50 |
| Mg-acetate | 10 | — | — | — | — |
| MgCl$_2$ | — | 5 | 10 | 10 | 10 |
| K-acetate | 66 | — | — | — | — |
| NaCl | — | 100 | — | 50 | 100 |
| Dithioerythritol (DTE) | — | — | 1 | 1 | 1 |
| Dithiothreitol (DTT) | 0.5 | — | — | — | — |
| 2-Mercaptoethanol | — | 1 | — | — | — |
| pH at 37° C. | 7.9 | 8.0 | 7.5 | 7.5 | 7.5 |

The above buffers are available from Boehringer Mannheim.

In the site-directed mutagenesis procedure - Reference Example 4

Buffer 1
100 mM Tris HCl pH 8.0
100 mM NaCl
20 mM MgCl$_2$

Buffer 2
10 mM Tris HCl pH 8.0
20 mM NaCl
1 mM EDTA

Buffer 3
12 mM Tris HCl pH 7.7
30 mM NaCl
10 mM MgCl$_2$
3 mM 2-mercaptoethanol

Buffer 4
60 mM Tris HCl pH 8.0
90 mM NaCl
6 mM MgCl$_2$
10 mM DTT

Nucleotide mix 1 250 μM each of dATP, dGTP, dCTP=S (phosphorothioate derivative of dCTP), dTTP and 1 mM ATP Nucleotide mix 2 250 μM each of dATP, dGTP, dCTP, dTTP and 350 μM ATP

Geneclean (TM)

The kit contains 1) 6M sodium iodide 2) a concentrated solution of sodium chloride, Tris and EDTA for making a sodium chloride/ethanol/water wash; 3) Glassmilk (TM)- a 1.5 ml vial containing 1.25 ml of a suspension of silica matrix in water.

This is a technique for DNA purification based on the method of Vogelstein and Gillespie published in Proceedings of the National Academy of Sciences USA (1979) Vol 76, p 615.

Alternatively any of the methods described in "Molecular Cloning—a laboratory manual" Second Edition, Sambrook, Fritsch and Maniatis (Cold Spring Harbor Laboratory, 1989) can be used.

Random Label Kit Product of Pharmacia No 27-9250

The procedure is described in "Molecular Cloning - a Laboratory Manual" Second Edition, Sambrook, Fritsch and Maniatis, pp 10.13-10.17 (Published by Cold Spring Harbor Laboratory 1989).

Sequenase (TM)

Chemically modified T7 DNA polymerase, based on the procedure of Tabor and Richardson published in "Proceedings of the National Academy of Sciences USA (1987) vol 84 pp 4767-4771.

Ultrogel AcA gels

A mixed matrix of polyacrylamide and agarose which provides the high resolution of polyacryamide and the rigidity of agarose in a synergistic association of the two components. Ultrogel AcA 54 contains 5% polyacrylamide and 4% agarose.

| M9 minimal media | |
|---|---|
| Ammonium chloride | 1 g |
| Disodium hydrogen orthophosphate | 6 g |
| Potassium dihydrogen orthophosphate | 3 g |
| Sodium chloride | 0.5 g |
| In distilled water | 1 l. |
| Supplements/75 ml | |
| 300 μl 50% glucose | |
| 75 μl 1 M MgSO$_4$ | |
| 75 μl 0.1 M CaCl$_2$ | |
| 75 μl 4 mg/ml thiamine | |
| 75 μl 20% casein amino acids | |

Trace Element Solution (TES)

TES has the following composition:

| | | | |
|---|---|---|---|
| AlCl$_3$6H$_2$O | 0.1 mg l$^{-1}$ | 100 μg l$^{-1}$ |
| CoCl$_2$6H$_2$O | 0.04 mg l$^{-1}$ | 40 μg l$^{-1}$ |
| KCr(SO$_4$)$_2$12H$_2$O | 0.01 mg l$^{-1}$ | 10 μg l$^{-1}$ |
| CuCl$_2$2H$_2$O | 0.01 mg l$^{-1}$ | 10 μg l$^{-1}$ |
| H$_3$BO$_3$ | 0.005 mg l$^{-1}$ | 5 μg l$^{-1}$ |
| KI | 0.1 mg l$^{-1}$ | 100 μg l$^{-1}$ |
| MnSO$_4$H$_2$O | 0.1 mg l$^{-1}$ | 100 μg l$^{-1}$ |
| NiSO$_4$6H$_2$O | 0.0045 ng l$^{-1}$ | 4.5 μg l$^{-1}$ |

| | | |
|---|---|---|
| -continued | | |
| Na$_2$MoO$_4$H$_2$O | 0.02 mg l$^{-1}$ | 20 μg l$^{-1}$ |
| ZnSO$_4$7H$_2$O | 0.02 mg l$^{-1}$ | 20 μg l$^{-1}$ | and is added to growth media at 0.5 ml/l

T4 DNA ligase

Described in "Molecular Cloning—a Laboratory Manual" Second Edition, Sambrook, Fritsch and Maniatis 5.60–5.64 (Published by Cold Spring Harbor Laboratory 1989) and also by Weiss B. et al J Biol. Chem. Vol 243 p 4543 (1968).

OXOID phosphate buffered saline

OXOID phosphate buffered saline as used herein is provided by Dulbecco 'A' tablets having the formula:

| | |
|---|---|
| Sodium chloride grams per liter | 8.0 |
| Potassium chloride | 0.2 |
| Disodium hydrogen phosphate | 1.15 |
| Potassium dihydrogen phosphate | 0.2 |
| pH | 7.3 |

10 tablets are dissolved in 1 liter of distilled water and autoclaved for 10 minutes at 115° C. to give a solution free of insoluble matter. The above solution corresponds to the original formulation of Dulbecco and Vogt (1954) J. Exp. Med. 99(2), 167–182 except that calcium and magnesium are omitted.

All nucleotide sequences referred to herein are specified in the conventional 5'→3' sense.

The derivatives of the present invention are based on human G-CSF which is also referred to as hu G-CSF.

Since the derivatives prepared in the Examples are all prepared using E.coli, a presequence methionine will generally be present.

The term "N-lauroyl sarcosine" as used herein refers to the use of the said substance in salt form. Thus in the Examples N-lauroyl sarcosine is used in the form of the sodium salt.

Monomethyl polyethylene glycol 5000 is also referred to herein as methyl polyethylene glycol 5000 and is referred to in certain catalogues of research chemicals as methoxy polyethylene glycol 5000.

The following non-limiting Examples are given by way of illustration only.

EXAMPLE 1

Continuous release pharmaceutical composition containing PEG5000-[Met$^{-1}$, Ser$^{17,27}$]hu G-CSF

GLACIAL ACETIC ACID PROCESS

Formulation A (protein at 20% loading)

Figure 13:
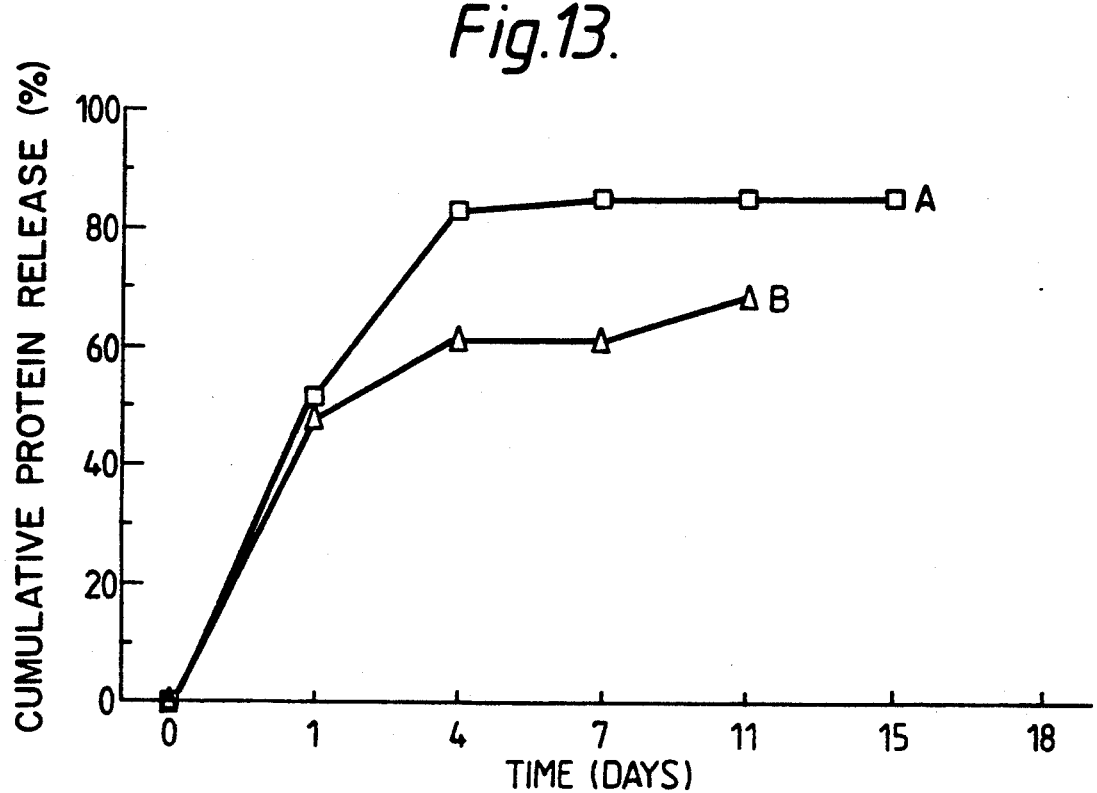
FIG. 13 shows the release of PEG 5000[Met$^{-1}$, Ser$^{17,27}$ ]hu G-CSF from 50% d,l-lactide/50% glycolide copolymer continuous release pharmaceutical compositions A and B (see Examples 4 and 5), both such compositions being prepared by a glacial acetic acid process.

27.7mg of polylactide (50 weight % d,l-lactide/50 weight % glycolide copolymer, weight average molecular weight 7673, polydispersity 2.59) was dissolved in 1.0 ml of glacial acetic acid. 1 ml of an aqueous solution of PEG 5000-[Met$^{-1}$, Ser$^{17,27}$]hu G-CSF (9 mg/ml) (from Reference Example 3) was freeze dried and then dissolved in a further 1 ml aliquot of glacial acetic acid The two solutions were mixed and a further 2×0.5 ml aliquots of glacial acetic acid used to rinse the glassware. The solution was immediately frozen in a bath of dichloromethane/drikold and freeze dried overnight. The freeze dried powder was mixed thoroughly using a hydraulic press with plattens heated to 85° C., and was then moulded at this temperature to give a slab 1 mm thick. The slab was cut into depots weighing approximately 10mg. The depots were then placed in plastic vials containing 2ml of OXOID phosphate buffered saline and 0.02% sodium azide and stored at 37° C. At regular intervals the aqueous medium was removed and replaced by fresh buffer. Release of PEG 5000-[Met$^{-1}$, Ser$^{17,27}$]hu G-CSF was determined by hplc analysis of the medium and the cumulative protein release calculated (see FIG. 13).

EXAMPLE 2

Continuous release pharmaceutical composition containing PEG 5000-[Met$^{-1}$, Ser$^{17,27}$]hu G-CSF-Glacial acetic acid process Formulation B (15.36% protein loading)

155.43 mg of polylactide (50 weight % d,l-lactide/50 weight % glycolide copolymer, weight average molecular weight 7791.2, polydispersity 2.65) was dissolved in 2.0 ml of glacial acetic acid. 3.79 ml of an aqueous solution of PEG 5000-[Met$^{-1}$, Ser$^{17,27}$]hu G-CSF (10.56 mg/ml) (from Reference Example 3) was freeze dried (post freeze drying weight 104.94 mg) and then dissolved in a further 2.0 ml aliquot of glacial acetic acid. The two solutions were mixed and a further 4×0.5 ml aliquots of glacial acetic acid used to rinse the glassware. The solution was immediately frozen in a bath of dichloromethane/drikold and freeze dried overnight. The freeze dried powder was mixed thoroughly using a hydraulic press with plattens heated to 70° C., and was then moulded at this temperature to give a slab 1 mm thick. The slab was cut into depots weighing approximately 70 mg. The depots were then placed in plastic vials containing 2 ml of OXOID phosphate buffered saline and 0.02% sodium azide and stored at 37° C. At regular intervals the aqueous medium was removed and replaced by fresh buffer. Release of PEG 5000-[Met$^{-1}$, Ser$^{17,27}$]hu G-CSF was determined by hplc analysis of the medium and the cumulative protein release calculated (see FIG. 13).

COMPARATIVE EXAMPLE 1

Continuous release pharmaceutical composition containing [Met$^{-1}$, Ser$^{17,27}$]hu G-CSF alone

GLACIAL ACETIC ACID PROCESS

Formulation C (protein at 20% loading)

Figure 14:
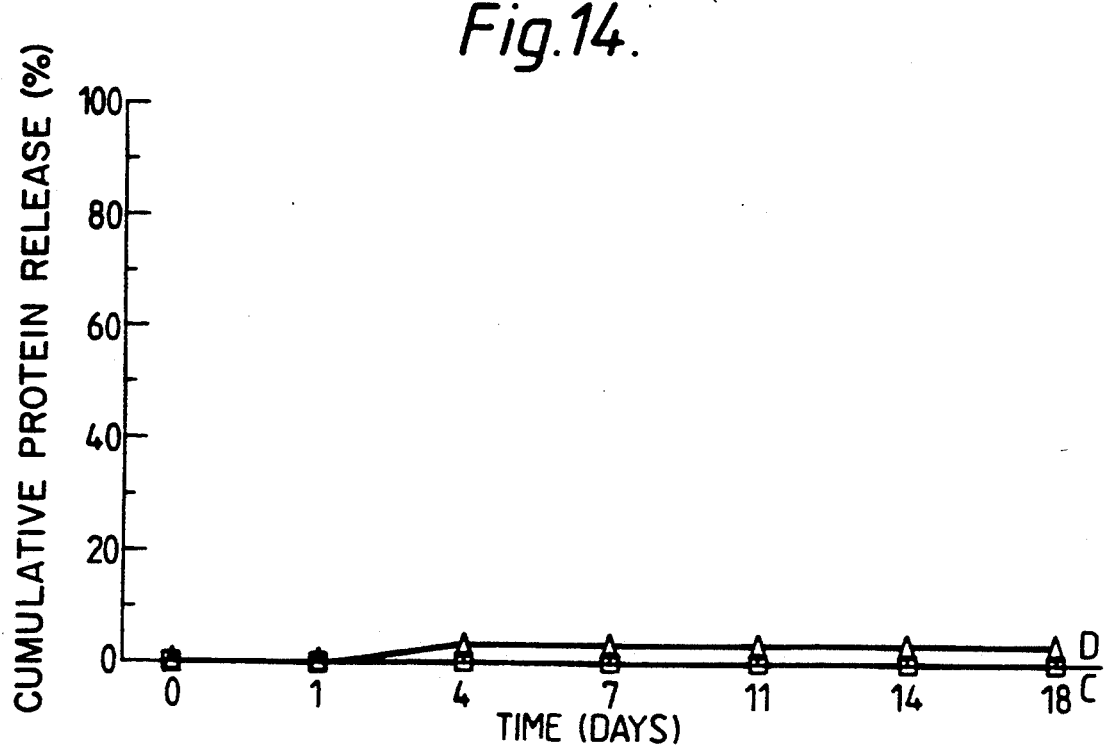
FIG. 14 shows the release of unpegylated [Met$^{-1}$, Ser$^{17,27}$]hu G-CSF from 50% d,l-lactide/50% glycolide copolymer continuous release pharmaceutical compositions C and D (see Comparative Examples 1 and 2) in which composition C comprises unpegylated [Met$^{-1}$, Ser$^{17,27}$]hu G-CSF alone and composition D comprises a mixture of unpegylated [Met$^{-1}$, Ser$^{17,27}$]hu G-CSF and methyl PEG 5000, both compositions being prepared by a glacial acetic acid process.

160.73 mg of polylactide (50 weight % d,l-lactide/50 weight % glycolide copolymer, weight average molecular weight 7673, polydispersity 2.59) was dissolved in 2.0 ml of glacial acetic acid. 4,088 ml of an aqueous solution of [Met$^{-1}$, Ser$^{17,27}$]hu G-CSF (10.0mg/ml) was freeze dried and then dissolved in a further 2.0 ml aliquot of glacial acetic acid. The two solutions were mixed and a further 2×0.5 ml aliquots of glacial acetic acid used to rinse the glassware. The solution was immediately frozen in a bath of dichloromethane/drikold and freeze dried overnight. The freeze dried powder was mixed thoroughly using a hydraulic press with plattens heated to 95° C., and was then moulded at this temperature to give a slab 1 mm thick. The slab was cut into depots weighing approximately 74 mg. The depots were then placed in plastic vials containing 2 ml of OXOID phosphate buffered saline and 0.02% sodium azide and stored at 37° C. At regular intervals the aqueous medium was removed and replaced by fresh buffer. Release of [Met$^{-1}$, Ser$^{17,27}$]hu G-CSF was determined by hplc analysis of the medium and the cumulative protein release calculated (see FIG. 14).

COMPARATIVE EXAMPLE 2

Continuous release pharmaceutical composition containing [Met$^{-1}$, Ser$^{17,27}$]hu G-CSF and methyl PEG 5000

GLACIAL ACETIC ACID PROCESS

Formulation D (protein at 20% loading)

120.66 mg of polylactide (50 weight % d,l-lactide/50 weight % glycolide copolymer, weight average molecular weight 7673, polydispersity 2.59) was dissolved in 2.0 ml of glacial acetic acid. 3.935 ml of an aqueous solution of [Met$^{-1}$, Ser$^{17,27}$]hu G-CSF (10.0 mg/ml) was freeze dried and then dissolved in 2.0 ml of a solution containing 40.82 mg methyl PEG 5000 in glacial acetic acid. The two solutions were mixed and a further 2×0.5 ml aliquots of glacial acid used to rinse the glassware.

The solution was immediately frozen in a bath of dichloromethane/drikold and freeze dried overnight. The freeze dried powder was mixed thoroughly using a hydraulic press with plattens heated to 95° C., and was then moulded at this temperature to give a slab 1 mm thick. The slab was cut into depots weighing approximately 74 mg. The depots were then placed in plastic vials containing 2 ml of OXOID phosphate buffered saline and 0.02% sodium azide and stored at 37° C. At regular intervals the aqueous medium was removed and replaced by fresh buffer. Release of [Met$^{-1}$, Ser$^{17,27}$]hu G-CSF was determined by hplc analysis of the medium and the cumulative protein release calculated (see FIG. 14).

EXAMPLE 3

Continuous release pharmaceutical composition containing PEG 5000-[Met$^{-1}$,Glu$^{15}$,Ser$^{17,27}$,Ala$^{26,28}$,Lys$^{30}$]hu G-CSF

GLACIAL ACETIC ACID PROCESS

Formulation E (protein at 20% loading)

120.34 mg of polylactide (50 weight % d,l-lactide/50 weight % glycolide copolymer, weight average molecular weight 7673, polydispersity 2.59) was dissolved in 2.0 ml of glacial acetic acid. 3.738 ml of an aqueous solution of PEG 5000-[Met$^{-1}$,Glu$^{15}$,Ser$^{17,27}$, Ala$^{26,28}$,Lys$^{30}$]hu G-CSF (10.7 mg/ml) (from Reference Example 8) was freeze dried and then dissolved in a further 2.0 ml aliquot of glacial acetic acid. The two solutions were mixed and a further 2×0.5 ml aliquots of glacial acid used to rinse the glassware. The solution was immediately frozen in a bath of dichloromethane/drikold and freeze dried overnight. The freeze dried powder was mixed thoroughly using a hydraulic press with plattens heated to 85° C., and was then moulded at this temperature to give a slab 1 mm thick. The slab was cut into depots weighing approximately 70 mg. The depots were then placed in plastic vials containing 2 ml of OXOID phosphate buffered saline and 0.02% sodium azide and stored at 37° C. At regular intervals the aqueous medium was removed and replaced by fresh buffer. Release of PEG 5000-[Met$^{-1}$,Glu$^{15}$,Ser$^{17,27}$,Ala$^{26,28}$, Lys$^{30}$]hu G-CSF was determined by hplc analysis of the medium and the cumulative protein release calculated (see FIG. 17).

EXAMPLE 4

Continuous release pharmaceutical composition containing PEG 5000-[Met$^{-1}$, Arg$^{11}$, Ser$^{17,27,60,65}$]hu G-CSF

GLACIAL ACETIC ACID PROCESS

Formulation F (protein at 20% loading polypeptide)

120.40 mg of polylactide (50 weight % d,l-lactide/50 weight % glycolide copolymer, weight average molecular weight 7673, polydispersity 2.59) was dissolved in 2.0 ml of glacial acetic acid. 3.478 ml of an aqueous solution of PEG 5000 [Met$^{-1}$,Arg$^{11}$, Ser$^{17,27,60,65}$]hu G-CSF (11.5 mg/ml) (from Reference Example 7) was freeze dried and then dissolved in a further 2.0 ml aliquot of glacial acetic acid. The two solutions were mixed and a further 2×0.5 ml aliquots of glacial acid used to rinse the glassware. The solution was immediately frozen in a bath of dichloromethane/drikold and freeze dried overnight. The freeze dried powder was mixed thoroughly using a hydraulic press with plattens heated to 85° C., and was then moulded at this temperature to give a slab 1 mm thick. The slab was cut into depots weighing approximately 72 mg. The depots were then placed in plastic vials containing 2 ml of OXOID phosphate buffered saline and 0.02% sodium azide and stored at 37° C. At regular intervals the aqueous medium was removed and replaced by fresh buffer. Release of PEG 5000-[Met$^{1}$,Arg$^{11}$,Ser$^{17,27,60,65}$]hu G-CSF was determined by hplc analysis of the medium and the cumulative protein release calculated (see FIG. 18).

EXAMPLE 5

Continuous release pharmaceutical composition containing PEG5000 [Met$^{-1}$]hu G-CSF A. Glacial Acetic Acid Process.

120.11 mg of polylactide (50 weight % d,l-lactide/50 weight % glycolide copolymer, weight average molecular weight 9429, polydispersity 2.02) were dissolved in 20 ml of anhydride-free glacial acetic acid. 3,738 ml of an aqueous solution of PEG 5000 [Met$^{-1}$] G-CSF (10.7 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/-Drikold and freeze-dried overnight. The freeze-dried powder was mixed thoroughly using a hydraulic press with plattens heated to 65° C. and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$] G-CSF was determined by HPLC analysis of the medium and cumulative protein release calculated (see Table 1 hereinafter).

B. Aqueous Process.

4.0g of polylactide (50 weight % d,l-lactide/50 weight % glycolide copolymer, weight average molecular weight 9429 polydispersity 2.02) were dissolved in 16.0 ml of dichloromethane and placed under high shear (Ystral 1500 homogeniser). To this were added 4 ml dropwise of aqueous sodium bicarbonate solution (20 mg/ml). A further 40 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.87 mg of the sodium salt of the polymer were dispersed-in 2.0 ml of distilled water. 3.738 ml of an aqueous solution of PEG-5000 [Met$^{-1}$]hu G-CSF (10.7 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG-5000 [Met$^{-1}$]hu G-CSF was determined by HPLC analysis of the medium and cumulative protein release calculated (see Table 1 hereinafter).

EXAMPLE 6

Continuous release pharmaceutical composition containing PEG 5000 [Met$^l$, Ser $^{17}$]hu G-CSF A. Glacial Acetic Acid Process 119.75 mg of polylactide (50 weight % d,l-lactide/50 weight % glycolide copolymer, weight average molecular weight 9429 polydispersity 2.02) were dissolved in 20 ml of anhydride-free glacial acetic acid 4.95 ml of an aqueous solution of PEG 5000 [Met$^{-1}$, Ser$^{17}$]hu G-CSF (see Reference Example 13) (8.08 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 70 mg. The depots were then placed in plastic vials containing 2.0 ml of 0.02% w/v sodium azide solution of OXOID phosphate-buffered saline and stored at 37° C. At regular intervals, the aqueous medium was removed and replaced by fresh buffer. Release of PEG 5000 [Met$^{-1}$, Ser$^{17}$]hu G-CSF was determined by HPLC analysis of the medium and cumulative protein release calculated (see Table 1 hereinafter).

B. Aqueous Process 4.0g of polylactide (50 weight % d,l-lactide/50 weight X glycolide copolymer, weight average molecular weight 9429, polydispersity 2.02) were dissolved in 16.0 ml of dichloromethane and placed under high shear (Ystral 1500 homogeniser). To this were added 4 ml dropwise of aqueous sodium bicarbonate solution (20 mg/ml). A further 40 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.80 mg of the sodium salt of the polymer were dispered in 2.0 ml of distilled water. 4.95 ml of an aqueous solution of PEG 5000 [Met$^{-1}$, Set$^{17}$]hu G-CSF (8.08 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Me$^{-1}$, Ser$^{17}$]hu G-CSF was determined by HPLC analysis of the medium and cumulative protein release calculated (see Table 1 hereinafter).

EXAMPLE 7

Continuous release pharmaceutical composition containing PEG 5000 [Met$^{-1}$, Arg$^{11,16}$, Ser$^{17,27,60,65}$]hu G-CSF A. Glacial Acetic Acid Process 20.72 mg of polylactide (50 weight % d,l-lactide/50 weight % glycolide copolymer, weight average molecular weight 9429 polydispersity 2.02) were dissolved in 2.0 ml of anhydride-free glacial acetic acid. 3.47 ml of an aqueous solution of PEG 5000 [Met$^{-1}$,Arg $^{11,16}$, Ser$^{17,27,60,65}$]hu G-CSF (see Reference Example 19) (11.53 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 65 mg. The depots were then placed in plastic vials containing 2.0 ml of 0.02% w/v sodium azide solution in OXOID phosphate-buffered saline and stored at 37° C. At regular intervals the aqueous medium was removed and replaced by fresh buffer. Release of PEG 5000 [Met$^{-1}$, Arg$^{11,16}$, Ser$^{17,27,60,65}$]hu G-CSF was determined by HPLC analysis of the medium and cumulative protein release calculated (see Table 1 hereinafter).

B. Aqueous Process 4.0g of polylactide 50 weight % d,l-lactide/50 weight % glycolide copolymer, weight average molecular weight 9429, polydispersity 2.02) were dissolved in 16.0 ml of dichloromethane and placed under high shear (Ystral 1500 homogeniser)- To this were added 4 ml dropwise of aqueous sodium bicarbonate solution (20 mg/ml). A further 40 ml of distilled water were added and a fine white dispersion produced. The dichloromethane was then removed using a rotary evaporator. The dispersion was immediately frozen in a bath of dichloromethane/Drikold and freeze-dried overnight.

This sodium salt of the polymer was subsequently stored under vacuum at room temperature prior to use.

119.71 mg of the sodium salt of the polymer were dispersed in 2.0 ml of distilled water. 3.47 ml of an aqueous solution of PEG 5000 [Met$^{-1}$, Arg$^{11,16}$, Ser$^{17,27,60,65}$]hu G-CSF (11.53 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 65° C., and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Ar$^{11,16}$, Ser$^{17,27,60,65}$]hu G-CSF was determined by HPLC analysis of the medium and cumulative protein release calculated (see Table 1 hereinafter).

EXAMPLE 8

Continuous release pharmaceutical composition containing PEG5000 [Met$^{-1}$, Arg$^{11,23}$, Ser$^{17,27,60,65}$]hu G-CSF A. Glacial Acetic Acid Process 120.11 mg of polylactide (50 weight % d,l-lactide/50 weight % glycolide copolymer, weight average molecular weight 9429 polydispersity 2.02) were dissolved in 2.0 ml of anhydride-free glacial acetic acid. 3.66 ml of an aqueous solution of PEG 5000 [Met$^{-1}$, Arg$^{11,23}$, Ser$^{17,27,60,65}$]hu G-CSF (see Reference Example 14) (10.93 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer Release of PEG 5000 [Met$^{-1}$, Arg$^{11,23}$, Ser$^{17,27,60,65}$]hu G-CSF was determined by HPLC analysis of the medium and cumulative protein release calculated (see Table 1 hereinafter).

B. Aqueous Process 4.0g of polylactide (50 weight % d,l-lactide/50 weight % glycolide copolymer weight average molecular weight 9429, polydispersity 2.02) were dissolved in 16 ml of dichloromethane and placed under high shear (Ystral 1500 homogeniser). To this were added 4 ml dropwise of aqueous sodium bicarbonate solution (20 mg/ml). A further 40 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.71 mg of the sodium salt of the polymer were dispered in 2.0 ml of distilled water. 3.66 ml of an aqueous solution of PEG 5000 [Met$^{-1}$, Arg$^{11,23}$, Ser$^{17,27,60,65}$]hu G-CSF (10.93 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 65° C. and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer Release of PEG 5000 [Met$^{-1}$, Arg$^{11,23}$, Ser$^{17,27,60,65}$]hu G-CSF was determined by HPLC analysis of the medium and cumulative protein release calculated (see Table 1 hereinafter).

EXAMPLE 9

Continuous release pharmaceutical composition containing PEG 5000 [Met$^{-1}$, Arg$^{11,34}$, Ser$^{17,27,60,65}$]hu G-CSF A. Glacial Acetic Acid Process 120.65 mg of polylactide (50 weight % d,l-lactide/50 weight % glycolide copolymer, weight average molecular weight 10691 polydispersity 1.75) were dissolved in 2.0 ml of anhydride-free glacial acetic acid. 3,810 ml Of an aqueous solution of PEG 5000 [Met$^{-1}$, Arg$^{11,34}$, Ser$^{17,27,60,65}$]hu G-CSF (see Reference Example 20) (10.5 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals the aqueous medium was removed and replaced by fresh buffer Release of PEG 5000 [Met$^{-1}$, Ar$^{11,34}$, Ser$^{17,27,60,65}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser). To this were added 5 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.15 mg of the sodium salt of the polymer were dispersed in 2.0 ml of distilled water. 3.810 ml of an aqueous solution of PEG 5000 [Met$^{-1}$, Arg$^{11,34}$, Ser$^{17,27,60,65}$]hu G-CSF (10.5 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 90° C., and was then moulded to give a slab 1 mm thick. The slab was cut into depots weighing approximately 75 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11,34}$, Ser$^{17,27,60,65}$]hu G-CSF was determined by HPLC analysis of the medium and cumulative protein release calculated (see Table 1 hereinafter).

EXAMPLE 10

Continuous release of pharmaceutical composition containing PEG 5000 [Met$^{-1}$, Arg$^{11,40}$, Ser$^{17,27,60,65}$]hu G-CSF.

A. Glacial Acetic Acid Process 120.74 mg of polylactide (50 weight % d,l-lactide/50 weight % glycolide copolymer, weight average molecular weight 10691, polydispersity 1.75) were dissolved in 2.0 ml of anhydride-free glacial acetic acid. 3.77 ml of an aqueous solution of PEG 5000 [Met$^{-1}$, Arg$^{11,40}$, Ser$^{17,27,60,65}$]hu G-CSF (see Reference Example 21) (10.6 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 95° C. and was then moulded to give a slab 1 mm thick. The slab was cut into depots weighing approximately 85 mg. The depots were then placed in plastic vials containing 2.0 ml of 0.02% w/v sodium azide solution in OXOID phosphate-buffered saline and stored at 37° C. At regular intervals the aqueous medium was removed and replaced by fresh buffer Release of PEG 5000 [Met$^{-1}$, Arg$^{11,40}$, Ser$^{17,27,60,65}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser). To this were added 5 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.20 mg of the sodium salt of the polymer were dispersed in 2.0 ml of distilled water. 3.77 ml of an aqueous solution of PEG 5000 [Met$^{-1}$, Arg$^{11,40}$, Ser$^{17,27,60,65}$]hu G-CSF (10.6 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 95° C. and was then moulded to give a slab 1 mm thick. The slab was cut into depots weighing approximately 72 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11,40}$, Ser$^{17,27,60,65}$]hu G-CSF was determined by HPLC analysis of the medium and cumulative protein release calculated (see Table 1 hereinafter).

EXAMPLE 11

Continuous release pharmaceutical composition containing PEG 5000 [Met$^{-1}$, Ala$^1$, Thr$^3$, Tyr$^4$, Arg$^{5,11}$, Ser$^{17,60,65}$]hu G-CSF A. Glacial Acetic Acid Process 119.79 mg of polylactide (60 weight % d,l-lactide/50 weight % glycolide copolymer, weight average molecular weight 10691, polydispersity 1.75) were dissolved in 2.0 ml of anhydride-free glacial acetic acid. 3.175 ml of an aqueous solution of PEG 5000 [Met$^{-1}$, Ala$^1$, Thr$^3$, Tyr$^4$, Arg$^{5,11}$, Ser $^{17,27,60,65}$]hu G-CSF (see Reference Example 22) (12.6 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 95° C. and was then moulded to give a slab 1 mm thick. The slab was cut into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Ala$^1$, Thr$^3$, Tyr$^4$, Arg$^{5,11}$, Ser$^{17,27,60,65}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser). To this were added 5 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

119.67 mg of the sodium salt of the polymer were dispered in 2.0 ml of distilled water. 3.175 ml of an aqueous solution of PEG 5000 [Met$^{-1}$, Ala$^1$, Thr$^3$, Tyr$^4$, Arg$^{5,11}$, Ser$^{17,27,60,65}$]hu G-CSF (12.6 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 95° C. and was then moulded to give a slab 1 mm thick. The slab was cut into depots weighing approximately 90 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Ala$^1$, Thr$^3$, Tyr$^4$, Arg$^{5,11}$, Ser$^{17,27,60,65}$]hu G-CSF was determined by HPLC analysis of the medium and cumulative protein release calculated (see Table 1 hereinafter).

EXAMPLE 12

Continuous release pharmaceutical composition containing PEG5000 [Met$^{-1}$, Glu$^{15}$, Ser$^{17,27}$, Ala$^{26,28}$, Arg$^{30}$]hu G-CSF A. Glacial Acetic Acid Process 120.25 mg of polylactide (50 weight % d,l-lactide/50 weight % glycolide copolymer, weight average molecular weight 10691 polydispersity 1.75) were dissolved in 2.0 ml of anhydride-free glacial acetic acid. 2.899 ml of an aqueous solution of PEG 5000 [Met$^{-1}$, Glu$^{15}$, Ser$^{17,27}$, Ala$^{26,28}$, Arg$^{30}$]hu G-CSF (see Reference Example 15) (13.8 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 100 mg. The depots were then placed in plastic vials containing 2.0 ml of 0.02% w/v sodium azide solution in OXOID phosphate-buffered saline and stored at 37° C. At regular intervals the aqueous medium was removed and replaced by fresh buffer. Release of PEG 5000 [Met$^{-1}$ Glu$^{15}$, Ser$^{17,27}$, Ala$^{26,28}$, Arg$^{30}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser)- To this were added 5 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt or the polymer was subsequently stored under vacuum at room temperature prior to use.

120.37 mg of the sodium salt of the polymer were dispersed in 2.0 ml of distilled water. 2.899 ml of an aqueous solution of PEG 5000 [Met$^{-1}$, Glu$^{15}$, Ser$^{17,27}$, Ala$^{26,28}$, Arg$^{30}$]hu G-CSF (13.8 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 95° C., and was then moulded to give a slab 1 mm thick. The slab was cut into depots weighing approximately 100 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Glu$^{15}$, Ser$^{17,27}$, Ala$^{26,28}$, Arg$^{30}$]hu G-CSF was determined by HPLC analysis of the medium and cumulative protein release calculated (see Table 1 hereinafter).

EXAMPLE 13

Continuous release pharmaceutical composition containing PEG 5000[Met$^{-1}$, Ser$^{17,27,115,116}$, Glu$^{111}$]hu G-CSF.

A. Glacial Acetic Acid Process 120.80 mg of polylactide (50 weight % d,l-lactide/50 weight % glycolide copolymer, weight average molecular weight 10691, polydispersity 1.75) were dissolved in 2.0 ml of anhydride-free glacial acetic acid. 3.333 ml of an aqueous solution of PEG 5000[Met$^{-1}$, Ser$^{17,27,115,116}$, Glu$^{111}$]hu G-CSF (see Reference Example 16) (12.0 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 95 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000[Met$^{-1}$, Ser$^{17,27,115,116}$, Glu$^{111}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser). To this were added 5.0 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

119.83 mg of the sodium salt of the polymer was dispered in 2.0 ml of distilled water. 3 333 ml of an aqueous solution of PEG 5000[Met$^{-1}$, Ser$^{17,27,115,116}$, Glu$^{111}$]hu G-CSF (12.0 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichlormethane/Drikold and freeze-dried overnight. The freeze-dried powder was mixed thoroughly using a hydraulic press with plattens heated to 95° C., and was then moulded to give a slab 1 mm thick. The slab was cut into depots weighing approximately 95 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000[Met$^{-1}$, Ser$^{17,27,115,116}$, Glu$^{111}$]hu G-CSF was determined by HPLC analysis of the medium and cumulative protein release calculated (see Table 1 hereinafter).

EXAMPLE 14

Continuous release pharmaceutical composition containing PEG 5000 [Met$^{-1}$, Arg$^{11,165}$, Ser$^{17,27}$, Lys$^{58}$]hu G-CSF.

A. Glacial Acetic Acid Process 119.28 mg of polylactide (50 weight % d,l-lactide/50 weight % glycolide copolymer, weight average molecular weight 10691, polydispersity 1.75) were dissolved in 2.0 ml of anhydride-free glacial acetic acid. 2.224 ml of an aqueous solution of PEG 5000 [Met$^{-1}$, Arg$^{11,165}$, Ser$^{17,27}$, Lys$^{58}$]hu G-CSF (17.905 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 100 mg. The depots were then placed in plastic vials containing 2.0 ml of 0.02% w/v sodium azide solution in OXOID phosphate-buffered saline and stored at 37° C. At regular intervals the aqueous medium was removed and replaced by fresh buffer. Release of PEG 5000 [Met$^{-1}$, Arg$^{11,165}$, Ser$^{17,27}$, Lys$^{58}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer, weight average molecular weight 10691, polydispersity 1.75) were dissolved in 20 ml of dichloromethane and placed under high shear (Ystral 1500 homogeniser). To this were added 5.0 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use. 119.82 mg of the sodium salt of the polymer were dispersed in 2.0 ml of distilled water. 2 224 ml of an aqueous solution of PEG 5000 [Met$^{-1}$, Arg$^{11,165}$, Ser$^{17,27}$, Lys$^{58}$]hu G-CSF (17.985 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 95° C., and was then moulded to give a slab 1 mm thick. The slab was cut into depots weighing approximately 90 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11,165}$, Ser$^{17,27}$, Lys$^{58}$]hu G-CSF was determined by HPLC analysis of the medium and cumulative protein release calculated (see Table 1 hereinafter).

EXAMPLE 15

Continuous release pharmaceutical composition containing PEG 5000 [Met$^{-1}$, Ser$^{17,27}$, Lys$^{49,58}$, Ala$^{44,51}$, ]hu G-CSF.

A. Glacial Acetic Acid Process 119.83 mg of polylactide (50 weight % d,l-lactide/50 weight % glycolide copolymer, weight average molecular weight 10691, polydispersity 1.75) were dissolved in 2.0 ml of anhydride-free glacial acetic acid. 2.317 ml of an aqueous solution of PEG 5000 [Met$^{-1}$, Ser$^{17,27}$, Lys$^{49,58}$, Ala$^{44,51,55}$]hu G-CSF (see Reference Example 18) (17.262 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 100 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Ser$^{17,27}$, Lys$^{49,58}$, Ala$^{44,51,55}$]hu G-CSF was determined by HPLC analysis of the medium and cumulative protein release calculated (see Table 1 hereinafter).

B. Aqueous process 5.0g of polylactide (50 weight % d,l-lactide/50 weight % glycolide copolymer, weight average molecular weight 10691, polydispersity 1.75) were dissolved in 20 ml of dichlormethane and placed under high shear Ystral 1500 homogeniser. To this were added 5.0 ml dropwise of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

120.82 mg 9f the sodium salt of the polymer were dispersed in 2.0 ml of distilled water. 2,317 ml of an aqueous solution of PEG 5000 [Met$^{-1}$, Ser$^{17,27}$, Lys$^{49,58}$, Ala$^{44,51,55}$]hu G-CSF (17.262 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 95° C. and was then moulded to give a slab 1 mm thick. The slab was cut into depots weighing approximately 100 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Ser$^{17,27}$, Lys$^{49,58}$, Ala$^{44,51,55}$]hu G-CSF was determined by HPLC analysis of the medium and cumulative protein release calculated (see Table 1 hereinafter).

EXAMPLE 16

Continuous release pharmaceutical composition containing PEG 750 [Met$^{-1}$, Arg$^{11}$, Ser$^{17,27,60,65}$]hu G-CSF.

GLACIAL ACETIC ACID PROCESS 150.11 mg of polylactide (50 weight % d,l-lactide/50 weight % glycolide copolymer, weight average molecular weight 10691, polydispersity 1.75) were dissolved in 2.0 ml of anhydride-free glacial acetic acid. 4.678 ml of an aqueous solution of PEG 750 [Met$^{-1}$, Arg$^{11}$, Ser$^{17,27,60,65}$]hu G-CSF (see Reference Example 24) (8.55 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick The slab was cut into depots weighing approximately 75 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 750 [Met$^{-1}$, Arg$^{11}$, Ser$^{17,27,60,65}$]hu G-CSF was determined by HPLC analysis of the medium and cumulative protein release calculated (see Table 1 hereinafter).

EXAMPLE 17

Continuous release pharmaceutical composition containing PEG 2000 [Met$^{-1}$, Arg$^{11}$, Ser$^{17,27,60,65}$]hu G-CSF.

A. Glacial Acetic Acid Process 140.32 mg of polylactide (50 weight % d,l-lactide/50 weight % glycolide copolymer, weight average molecular weight 10691, polydispersity 1.75) were dissolved in 2.0 ml of anhydride-free glacial acetic acid. 4,695 ml an aqueous solution of PEG 2000 [Met$^{-1}$, Arg$^{11}$, Ser$^{17,27,60,65}$]hu G-CSF (see Reference Example 23) (8.52 mg/ml) were freeze-dried and then dissolved in a further 2.0 ml of the glacial acetic acid. The two solutions were mixed and a further 4×0.5 ml aliquots of the glacial acetic acid used to rinse the glassware. The solution was immediately frozen in a bath of dichloromethane/Drikold and freeze-dried overnight. The freeze-dried powder was mixed thoroughly using a hydraulic press with plattens heated to 90° C. and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 2000 [Met$^{-1}$, Arg$^{11}$, Ser$^{17,27,60,65}$]hu G-CSF was determined by HPLC analysis of the medium and cumulative protein release calculated (see Table 1 hereinafter).

B. Aqueous Process 5.0g of polylactide (50 weight % d,l-lactide/50 weight % glycolide copolymer weight average molecular weight 10691, polydispersity 1.75) were dissolved in 20 ml of dichloromethane and placed under high shear (Ystral 1500 homogeniser). To this were added 5.0 ml dropwise, of aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use. 140.85 mg of the sodium salt of the polymer were dispered in 2.0 ml of distilled water 4.695 ml of an aqueous solution of PEG 2000 [Met$^{-1}$, Arg$^{11}$, Ser$^{17,27,60,65}$]hu G-CSF (8.25 mg/ml) were freeze-dried and then dissolved in a further 2.0 ml of distilled water. The solution was added to the suspension and mixed. A further 4×0.5 ml aliquots of the distilled water were used to rinse the glassware. The solution was immediately frozen in a bath of dichloromethane/Drikold and freeze-dried overnight. The freeze-dried powder was mixed thoroughly using a hydraulic press with plattens heated to 90° C., and was then moulded to give a slab 1 mm thick. The slab was cut into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 2000 [Met$^{-1}$, Arg$^{11}$, Ser$^{17,27,60,65}$]hu G-CSF was determined by HPLC analysis of the medium and cumulative protein release calculated (see Table 1 below).

TABLE 1A

Release of G-CSF Analogues from Lactide:Glycolide:G 1:1 Formulations

| Example No | Process | Protein Load (by wt %) | Polymer Load (By wt %) | Polymer No. | Press Temp °C. |
|---|---|---|---|---|---|
| 5A | GAA | 16.26 | 48.81 | 310 | 65 |
| 5B | Aq | 16.16 | 48.83 | 310 | 65 |
| 6A | GAA | 16.89 | 50.56 | 310 | 65 |
| 6B | Aq | 16.84 | 50.87 | 310 | 65 |
| 7A | GAA | 17.49 | 52.79 | 310 | 65 |
| 7B | Aq | 17.65 | 52.82 | 310 | 65 |
| 8A | GAA | 16.94 | 50.88 | 310 | 65 |
| 8B | Aq | 16.88 | 50.95 | 310 | 65 |
| 9A | GAA | 16.54 | 49.87 | 312 | 90 |
| 9B | Aq | 16.60 | 49.87 | 312 | 90 |
| 10A | GAA | 16.49 | 49.77 | 312 | 95 |
| 10B | Aq | 15.73 | 47.27 | 312 | 95 |
| 11A | GAA | 15.23 | 45.60 | 312 | 95 |
| 11B | Aq | 14.87 | 44.48 | 312 | 95 |
| 12A | GAA | 16.08 | 48.35 | 312 | 90 |
| 12B | Aq | 16.12 | 48.52 | 312 | 95 |
| 13A | GAA | 16.51 | 49.85 | 312 | 90 |
| 13B | Aq | 16.38 | 49.06 | 312 | 95 |
| 14A | GAA | 16.19 | 48.27 | 312 | 90 |
| 14B | Aq | 15.92 | 47.68 | 312 | 95 |
| 15A | GAA | 15.63 | 46.81 | 312 | 90 |
| 15B | Aq | 15.06 | 45.48 | 312 | 95 |
| 16 | GAA | 19.17 | 71.95 | 312 | 90 |
| 17A | GAA | 17.30 | 60.93 | 312 | 90 |
| 17B | Aq | 17.56 | 62.82 | 312 | 90 |

The terms "GAA" and "Aq" used above refer to the glacial acetic acid and aqueous processes for formulation respectively

TABLE 1B

Rate of release of protein from above formulations

| Example No. | % Protein released at day | | | | | |
|---|---|---|---|---|---|---|
| | 1 | 4 | 6 | 11 | 16 | 18 |
| 5A | 27.1 | 36.5 | 37.1 | 37.5 | 37.5 | 37.5 |
| 4B | 33.3 | 37.5 | 38.6 | 39.1 | 40.1 | 40.1 |
| 6A | 77.0 | 96.4 | 102.7 | 106.7 | 111.3 | 112.9 |
| 6B | 56.8 | 86.6 | 98.3 | 103.9 | 109.4 | |
| 7A | 42.5 | 55.9 | 60.4 | 64.5 | 67.9 | 70.8 |
| 7B | 46.5 | 59.9 | 65.3 | 74.5 | 80.7 | 81.5 |
| 8A | 50.3 | 66.4 | 72.4 | 78.2 | 85.2 | 86.6 |
| 8B | 55.5 | 78.4 | 84.8 | 87.8 | 89.5 | 90.1 |

| | % Protein release at day | | | | |
|---|---|---|---|---|---|
| | 1 | 4 | 8 | 11 | 15 | 18 |
| 9A | 16.2 | 21.8 | 24.6 | 40.1 | 43.9 | |
| 9B | 27.2 | 37.3 | 41.6 | 45.0 | 54.1 | |
| 10A | 29.6 | 41.3 | 46.2 | | | |
| 10B | 33.8 | 51.1 | 59.9 | 64.6 | 69.3 | |
| 11A | 45.9 | 60.1 | 65.7 | | | |
| 11B | 42.0 | 66.0 | 72.9 | 74.6 | | |

| | % Protein release at day | | | | |
|---|---|---|---|---|---|
| | 1 | 3 | 8 | 11 | 15 | 18 |
| 12A* | 56.3 | 84.4 | 99.4 | 99.4 | | |
| 12B* | 51.7 | 74.9 | 89.3 | 93.8 | 99.2 | |
| 13A* | 37.3 | 67.7 | 85.8 | 108.6 | | |
| 13B* | 36.2 | 75.7 | 95.2 | 104.0 | 105.2 | |
| 14A* | 28.6 | 47.2 | 55.6 | 74.3 | | |
| 14B* | 24.2 | 48.3 | 61.0 | 77.8 | 81.6 | |
| 15A* | 58.1 | 84.4 | 96.0 | 96.2 | | |
| 15B* | 50.3 | 111.3 | 127.2 | 129.7 | 131.9 | 132.3 |

| | % Protein release at day | | | | |
|---|---|---|---|---|---|
| | 1 | 4 | 8 | 11 | 15 | 18 |
| 16 | 6.2 | 6.7 | 6.8 | 6.9 | 6.9 | 6.9 |
| 17A | 22.6 | 32.7 | 41.0 | 43.1 | 45.6 | 46.5 |
| 17B | 26.2 | 36.3 | 42.8 | 44.8 | 48.2 | 49.3 |

*Release figures worked out using protein content of formulation calculated by weight not amino acid analysis.

EXAMPLE 18

Continuous release pharmaceutical composition containing PEG 5000 [Met$^{-1}$, Arg$^{11}$, Ser$^{17,27,60,65}$]hu G-CSF (Lactide;Glycolide 80:20)

A. Glacial Acetic Acid Process (Protein at 5.52% loading)

158.91 mg of polylactide (80 weight % d,l-lactide/20 weight % glycolide copolymer, weight average molecular weight 7952, polydispersity 2.01) were dissolved in 2.0 ml of anhydride-free glacial acetic acid. 41.90 mg of a freeze-dried preparation of PEG 5000 [Met$^{-1}$, Arg$^{11}$, Ser$^{17,27,60,65}$]hu G-CSF were dissolved in a further 2.0 ml of the glacial acetic acid. The two solutions were mixed and a further 4×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 75° C., and was moulded into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11}$, Ser$^{17,27,60,65}$]hu G-CSF was determined by HPLC analysis of the medium and cumulative protein release calculated.

| Release of protein from formulation | |
|---|---|
| Day | % Release |
| 1 | 10.41 |
| 4 | 17.36 |
| 7 | 21.73 |
| 11 | 24.47 |
| 14 | 27.67 |
| 18 | 30.69 |

EXAMPLE 19

Continuous release pharmaceutical composition containing PEG 5000 Met$^{-1}$, Arg$^{11}$, Ser$^{17,27,60,65}$]hu G-CSF [80% (Lactide:Glycolide 50)/20% methyl polyethylene glycol 2000].

A. Glacial Acetic Acid Process (Protein at 5.23% loading)

159.87g of a hydrogel (80.7 weight % d,l-lactide/glycolide copolymer, 19.3 weight % 2000 MePEG) were dissolved in 2.0 ml of anhydride-free glacial acetic acid. 40.26 mg of a freeze-dried preparation of PEG 5000 [Met$^{-1}$, Arg$^{11}$, Ser$^{17,27,60,65}$]hu G-CSF (26.46 weight % protein) were dissolved in a further 2.0 ml of the glacial acetic acid. The two solutions were mixed and a further 4×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 60° C., and was then moulded into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11}$, Ser$^{17,27,60,65}$]hu G-CSF was determined by HPLC analysis of the medium and cumulative protein release calculated.

| Release of protein from formulation | |
|---|---|
| Day | % Release |
| 1 | 24.57 |
| 4 | 40.85 |
| 8 | 67.16 |
| 11 | 79.91 |
| 15 | 91.57 |

EXAMPLE 20

Continuous release pharmaceutical composition containing PEG 5000 [Met$^{-1}$, Arg$^{11}$ $^{17,27,60,65}$]hu G-CSF [80% (Lactide:Glycolide 100:0)/20% methyl polyethylene glycol 2000].

A. Glacial Acetic Acid Process (Protein at 5.23% loading)

159.70g of a hydrogel (82.5 weight % poly d,l-lactide, 17.5 weight % 2000 MePEG) were dissolved in 2.0 ml of anhydride-free glacial acetic acid. 39.50 mg of a freeze-dried preparation of PEG 5000 [Met$^{-1}$, Arg$^{11}$, Ser$^{17,27,60,65}$]lu G-CSF (26.46 weight % protein) were dissolved in a further 2.0 ml of the glacial acetic acid. The two solutions were mixed and a further 4×0 5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 60° C. and was then moulded into depots weighing approximately 70 mg. The depots were then placed in plastic vials containing 2.0 ml of 0.02% w/v sodium azide solution of OXOID phosphate-buffered saline and stored at 37° C. At regular intervals, the aqueous medium was removed and replaced by fresh buffer. Release of PEG 5000 [Met$^{-1}$, Arg$^{11}$, Ser$^{17,27,60,65}$]hu G-CSF was determined by HPLC analysis of the medium and cumulative protein release calculated.

| Release of protein from formulation | |
|---|---|
| Day | % Release |
| 1 | 25.19 |
| 4 | 63.52 |
| 8 | 86.20 |
| 11 | 93.67 |
| 15 | 97.50 |
| 18 | 98.88 |

EXAMPLE 21

Continuous release pharmaceutical composition containing PEG 5000 [Met$^{-1}$, Arg$^{11}$, Ser$^{17,27,60,65}$]hu G-CSF (Lactide:Glycolide 50:50)

A. Glacial Acetic Acid Process (Protein at 4.14% loading) 160.34 mg of polylactide (50 weight % d,l-lactide/50 weight % glycolide copolymer, weight average molecular weight 9827 polydispersity 2.18) were dissolved in 2.0 ml of anhydride-free glacial acetic acid. 40.73 mg of a freeze-dried preparation of PEG 5000 [Met$^{-1}$, Arg$^{11}$, Ser$^{17,27,60,65}$]hu G-CSF were dissolved in a further 2.0 ml of the glacial acetic acid. The two solutions were mixed and a further 4×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 60° C. and was moulded into depots weighing approximately 60 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer Release of PEG 5000 [Met$^{-1}$, Arg$^{11}$, Ser$^{17,27,60.65}$]hu G-CSF was determined by HPLC analysis of the medium, and cumulative protein release calculated.

| Release of protein from formulation | |
|---|---|
| Day | % Release |
| 1 | 18.05 |
| 4 | 40.00 |
| 8 | 57.47 |
| 11 | 66.18 |
| 14 | 72.06 |
| 18 | 77.77 |

EXAMPLE 22

Continuous release pharmaceutical composition containing PEG 5000 [Met$^{-1}$, Arg$^{11}$, Ser$^{17,27,60,65}$]hu G-CSF (Lactide:Glycolide 75:25)

GLACIAL ACETIC ACID PROCESS 161.46 mg of polylactide (75 weight % d,l-lactide/25 weight % glycolide copolymer, weight average molecular weight 12938, polydispersity 1.81) were dissolved in 2.0 ml of anhydride-free glacial acetic acid. 39.03 mg of a freeze-dried preparation of PEG TG50 were dissolved in a further 2.0 ml of the glacial acetic acid. The two solutions were mixed and a further 4×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 75° C. and was moulded into depots weighing approximately 80 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11}$, Ser$^{17,27,60,65}$]hu G-CSF was determined by HPLC analysis of the medium, and cumulative protein release calculated.

| Release of protein from formulation | |
|---|---|
| Day | % Release |
| 1 | 7.82 |
| 4 | 12.27 |
| 7 | 15.46 |
| 11 | 17.25 |
| 14 | 19.38 |
| 18 | 21.06 |

EXAMPLE 23

Continuous release pharmaceutical composition containing PEG 5000 [Met$^{-1}$, Arg$^{11}$, Ser$^{17,27,60,65}$]hu G-CSF (Lactide:Glycolide 100:0)

GLACIAL ACETIC ACID PROCESS (PROTEIN AT 5.3% LOADING)

158.67 mg of polylactide (100 weight % d,l-lactide/0 weight % glycolide copolymer, weight average molecular weight 9042 polydispersity 1.96) were dissolved in 2.0 ml of anhydride-free glacial acetic acid 40.42 mg of a freeze-dried preparation of PEG 5000 [Met $^{-1}$, Arg$^{11}$, Ser$^{17,27\ 60,65}$]hu G-CSF were dissolved in a further 2.0 ml of the glacial acetic acid. The two solutions were mixed and a further 4 ×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 75° C., and was moulded into depots weighing approximately 70 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 [Met$^{-1}$, Arg$^{11}$, Ser$^{17,27,60,65}$]hu G-CSF was determined by HPLC analysis of the medium, and cumulative protein release calculated.

| Release of protein from formulation | |
|---|---|
| Day | % Release |
| 1 | 13.02 |
| 4 | 22.46 |
| 7 | 29.44 |
| 11 | 33.15 |
| 14 | 36.34 |

-continued

| Release of protein from formulation | |
|---|---|
| Day | % Release |
| 18 | 41.31 |

EXAMPLE 24

Continuous release pharmaceutical composition containing PEG 5000 [Met$^{-1}$, Ser$^{17,27}$]hu G-CSF - Aqueous process i) Formulation G (protein at 20% loading)

4.0g of polylactide (50 weight % d,l-lactide/50 weight % glycolide copolymer, weight average molecular weight 7673, polydispersity 2.59) was dissolved in 12 ml of dichloromethane and placed under high shear (Ystral 1500 homogeniser). To this was added dropwise 4 ml of aqueous sodium bicarbonate solution (20 mg/ml). A further 60 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

160.31 mg of the sodium salt of the polymer was dispersed in 2 ml of distilled water. 4 396 ml of an aqueous solution of PEG 5000[Met$^{-1}$, Ser$^{17,27}$]hu G-CSF (9.1 mg/ml) was diluted to 5 mg/ml with distilled water and added to the polymer salt suspension. A further 4×0.5 ml aliquots of distilled water were used to rinse the glassware. The solution was immediately frozen in a bath of dichloromethane/Drikold and freeze dried overnight. The freeze-dried powder was mixed thoroughly using a hydraulic press with plattens heated to 90° C., and was then moulded at this temperature to give a slab 1 mm thick. The slab was cut into depots weighing approximately 105 mg. The depots were then placed in plastic vials containing 2 ml of OXOID phosphate buffered saline, 0.02% sodium azide and stored at 37° C. At regular intervals the aqueous medium was removed and replaced by fresh buffer. Release of PEG 5000 [Met$^{-1}$, Ser$^{17,27}$]hu G-CSF was determined by hplc analysis of the medium and cumulative protein release calculated.

ii) Formulation H (protein at 20% loading)

4.0g of polylactide (50weight % d,l-lactide/50 weight % glycolide copolymer, weight average molecular weight 7791.2, polydispersity 2.65) was dissolved in 16 ml of dichloromethane and placed under high shear (Ystral 1500 homogeniser). To this was added dropwise 4 ml of aqueous sodium bicarbonate solution (20 mg/ml). A further 40 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

Figure 15:
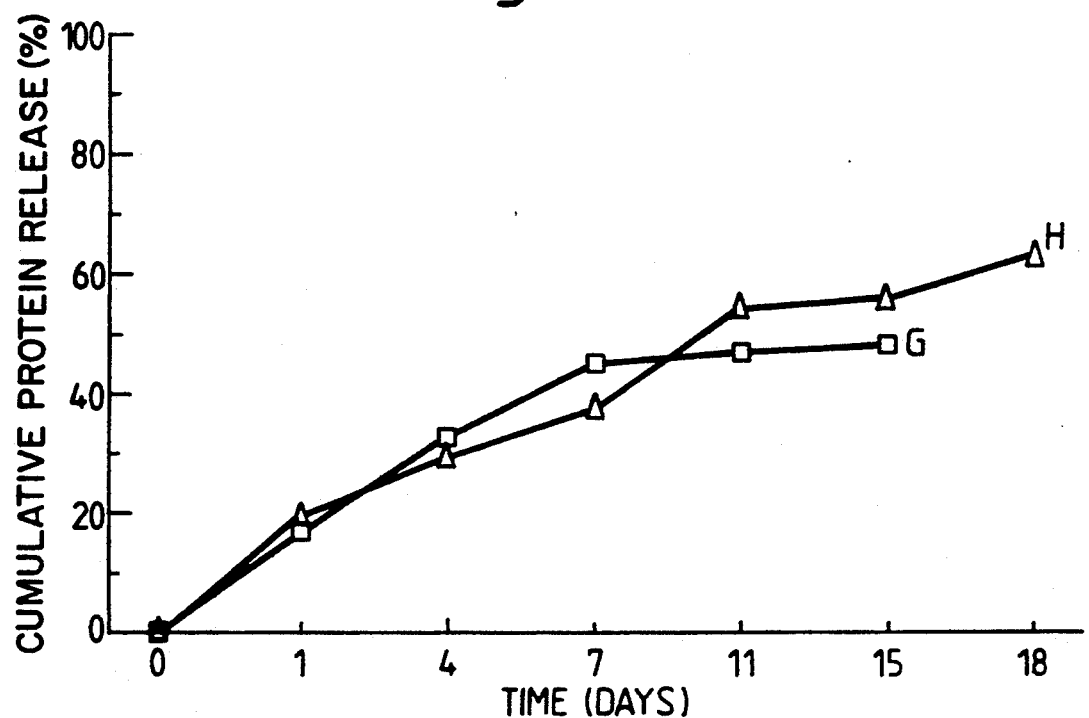
FIG. 15 shows the cumulative release of PEG 5000 [Met$^{-1}$, Ser$^{17,27}$]hu G-CSF from two different 50% d,l-lactide/50% glycolide copolymer continuous release pharmaceutical compositions G and H (see Example 24), both such compositions being prepared by an aqueous process.

89.84 mg of the sodium salt of the polymer was dispersed in 2 ml of distilled water. 3.33 ml of an aqueous solution of PEG 5000 [Met$^{-1}$, Ser$^{17,27}$]hu G-CSF (9 mg/ml) was added to the polymer salt suspension. A further 4×0.5 ml aliquots of distilled water were used to rinse the glassware. The solution was immediately frozen in a bath of dichloromethane/Drikold and freeze-dried overnight. The freeze-dried powder was mixed thoroughly using a hydraulic press with plattens heated to 95° C., and was then moulded at this temperature to give a slab 1 mm thick. The slab was cut into depots weighing approximately 63 mg. The depots were then placed in plastic vials containing 2 ml of OXOID phosphate buffered saline, 0.02% sodium azide and stored at 37° C. At regular intervals the aqueous medium was removed and replaced by fresh buffer. Release of PEG 5000 [Met$^{-1}$, Ser$^{17,27}$]hu G-CSF was determined by hplc analysis of the medium and cumulative protein release calculated. A comparison of cumulative release for formulations G and H is shown in FIG. 15.

COMPARATIVE EXAMPLE 3

Continuous release pharmaceutical composition containing [Met$^{-1}$, Ser$^{17,27}$]hu G-CSF alone - Aqueous process Formulation I (protein at 20% loading)

4.0g of polylactide (50 weight % d,l-lactide/50 weight % glycolide copolymer, weight average molecular weight 7791.2, polydispersity 2.65) was dissolved in 16 ml of dichloromethane and placed under high shear (Ystral 1500 homogeniser). To this was added dropwise 4 ml of aqueous sodium bicarbonate solution (20 mg/ml). A further 40 ml of distilled water was added and a fine white dispersion produced. The dichloromethane was removed using a rotary evaporator. The solution was immediately frozen in a bath of dichloromethane/Drikold and freeze-dried overnight. This sodium salt of the polymer was subsequently stored under vacuum at room temperature.

Figure 16:
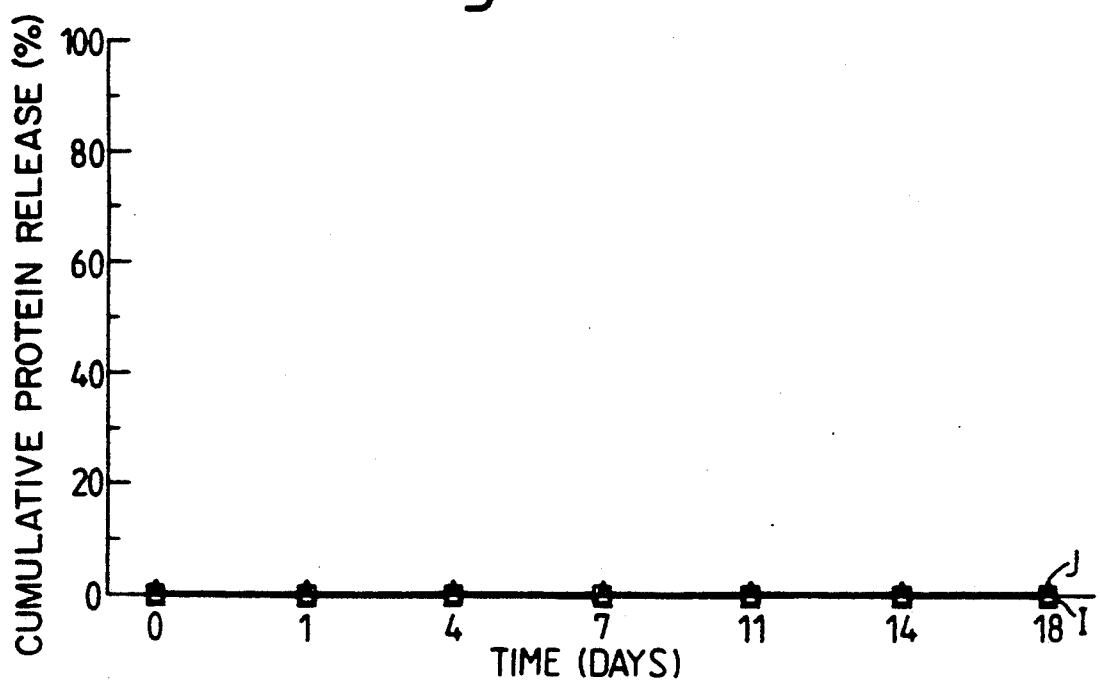
FIG. 16 shows the cumulative release of [Met$^{-1}$, Ser$^{17,27}$]hu G-CSF from a 50% d,l-lactide/50% glycolide copolymer continuous release pharmaceutical composition containing [Met$^{-1}$, Ser$^{17,27}$]hu G-CSF alone (see Comparative Example 3) and from a 50% d,l-lactide/50% glycolide copolymer continuous release pharmaceutical composition containing a mixture of [Met$^{-1}$, Ser$^{17,27}$]hu G-CSF and methyl Peg 5000 (see comparative Example 4) both compositions having been prepared by an aqueous process.

160.20 mg of the sodium salt of the polymer was dispersed in 2 ml of distilled water. 4.000 ml of an aqueous solution of [Met$^{-1}$, Ser$^{17,27}$]hu G-CSF (10.0 mg/ml) was diluted to 5 mg/ml with distilled water and added to the polymer salt suspension. A further 4×0.5 ml aliquots of distilled water were used to rinse the glassware. The solution was immediately frozen in a bath of dichloromethane/Drikold and freeze-dried overnight. The freeze-dried powder was mixed thoroughly using a hydraulic press with plattens heated to 95° C., and was then moulded at this temperature to give a slab 1 mm thick. The slab was cut into depots weighing approximately 81 mg. The depots were then placed in plastic vials containing 2 ml of OXOID phosphate buffered saline, 0.02% sodium azide and stored at 37° C. At regular intervals the aqueous medium was removed and replaced by fresh buffer. Release of [Met$^{-1}$, Ser$^{17,27}$]hu G-CSF was determined by hplc analysis of the medium and cumulative protein release calculated. Cumulative protein release for formulation I is shown in FIG. 16.

COMPARATIVE EXAMPLE 4

Continuous release pharmaceutical composition containing [Met$^{-1}$, Ser$^{17,27}$]hu G-CSF and methyl PEG 5000 - Aqueous process Formulation J (protein at 20% loading)

4.0g of polylactide (50 weight % d,l-lactide/50 weight % glycolide copolymer, weight average molecular weight 7791.2, polydispersity 2.65) was dissolved in 16 ml of dichloromethane and placed under high shear (Ystral 1500 homogeniser). To this was added dropwise 4 ml of aqueous sodium bicarbonate solution (20 mg/ml). A further 40 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

119.77 mg of the sodium salt of the polymer was dispered in 2 ml of distilled water 4 000 ml of an aqueous solution of [Met$^{-1}$, Ser$^{17,27}$]hu G-CSF (10.0 mg/ml) was diluted to 5 mg/ml with an aqueous solution containing 40.43 mg of methyl PEG5000 and added to the polymer salt suspension. A further 4×0.5 ml aliquots of distilled water were used to rinse the glassware. The solution was immediately frozen in a bath of dichloromethane/Drikold and freeze-dried overnight. The freeze dried powder was mixed thoroughly using a hydraulic press with plattens heated to 95° C., and was then moulded at this temperature to give a slab 1 mm thick. The slab was cut into depots weighing approximately 83 mg. The depots were then placed in plastic vials containing 2 ml of OXOID phosphate buffered saline, 0.02% sodium azide and stored at 37° C. At regular intervals the aqueous medium was removed and replaced by fresh buffer. Release of [Met$^{-1}$, Ser$^{17,27}$]hu G-CSF was determined by hplc analysis of the medium and cumulative protein release calculated. Cumulative protein release for formulation J is shown in FIG. 16.

EXAMPLE 25

Continuous release pharmaceutical composition containing PEG 5000 [Met$^{-1}$, Glu$^{15}$, Ser$^{17,27}$, Ala$^{26,28}$, Lys$^{30}$]hu G-CSF - Aqueous process Formulation K (protein at 20% loading)

4.0g of polylactide (50 weight % d,l-lactide/50 weight % glycolide copolymer, weight average molecular weight 7791.2, polydispersity 2.65) was dissolved in 16 ml of dichloromethane and placed under high shear (Ystral 1500 homogeniser). To this was added dropwise 4 ml of aqueous sodium bicarbonate solution (20 mg/ml). A further 40 ml of distilled water was added and a fine white dispersion produced. The dichloromethane was removed using a rotary evaporator. The solution was immediately frozen in a bath of dichloromethane/Drikold and freeze-dried overnight. This sodium salt of the polymer was subsequently stored under vacuum at room temperature.

Figure 17:
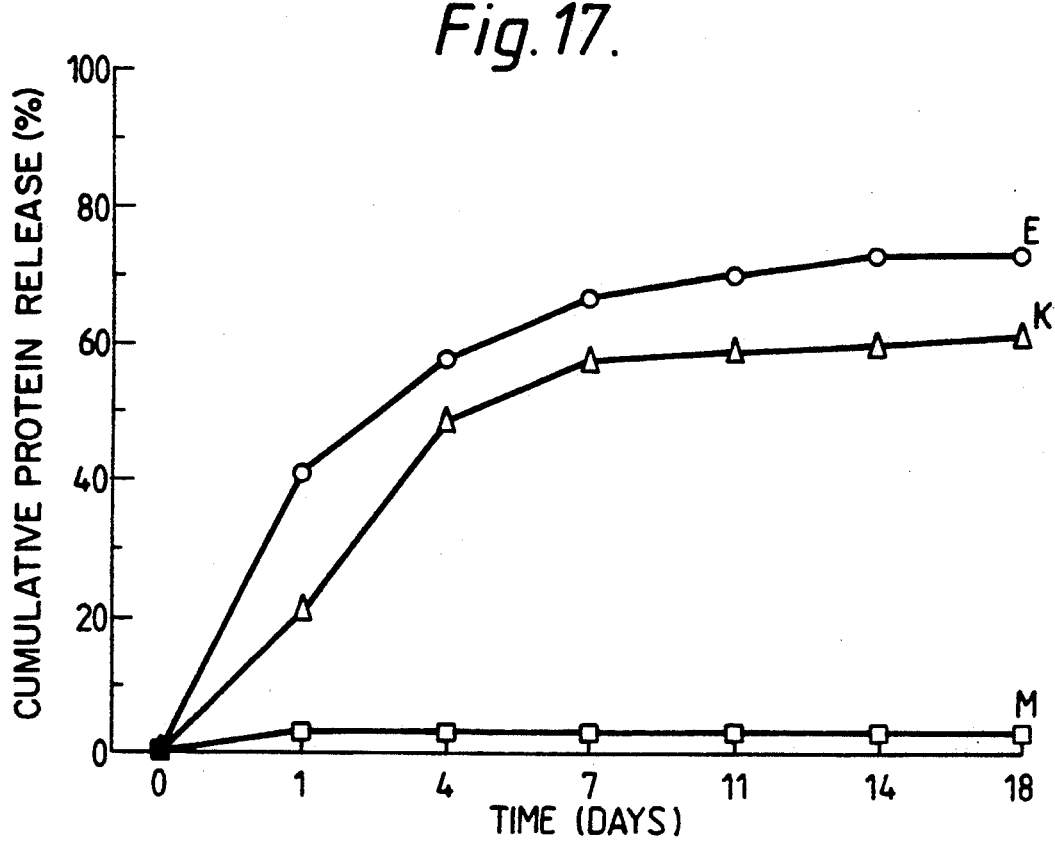
FIG. 17 shows the cumulative release of PEG 5000 [Met$^{-1}$, Ser$^{17,27}$, Ala$^{26,28}$, Lys30]hu G-CSF from 50% d,l-lactide/50% glycolide copolymer continuous release pharmaceutical compositions E (see Example 3), K (see Example 25), and M (see Comparative Example 5), composition E being prepared by the glacial acetic acid process and compositions K and M being prepared by an aqueous process.

120.8 mg of the sodium salt of the polymer was dispersed in 2 ml of distilled water. 3 738 ml of an aqueous solution of PEG 5000 [Met$^{-1}$, Glu$^{15}$, Ser$^{17,27}$, Ala$^{26,28}$, Lys$^{30}$]hu G-CSF (10.7 mg/ml) was added to the polymer salt suspension. A further 4×0.5 ml aliquots of distilled water were used to rinse the glassware. The solution was immediately frozen in a bath of dichloromethane/Drikold and freeze dried overnight. The freeze dried powder was mixed thoroughly using a hydraulic press with plattens heated to 80° C., and was then moulded at this temperature to give a slab 1 mm thick. The slab was cut into depots weighing approximately 95 mg. The depots were then placed in plastic vials containing 2 ml of OXOID phosphate buffered saline, 0.02% sodium azide and stored at 37° C. At regular intervals the aqueous medium was removed and replaced by fresh buffer. Release of PEG 5000 [Met$^{-1}$, Glu$^{15}$, Ser$^{17,27}$, Ala$^{26,28}$, Lys$^{30}$]hu G-CSF was determined by hplc analysis of the medium and cumulative protein release calculated. Cumulative protein release for formulation K is shown in FIG. 17.

EXAMPLE 26

Continuous release pharmaceutical composition containing PEG 5000 [Met$^{-1}$, Arg$^{11}$, Ser$^{17,27,60,65}$]hu G-CSF - Aqueous process.

A. Aqueous process
 i) Formulation L (protein at 20% loading)

4.0g of polylactide (50 weight % d,l-lactide/50 weight % glycolide copolymer, weight average molecular weight 7791.2, polydispersity 2.65) was dissolved in 16 ml of dichloromethane and placed under high shear (Ystral 1500 homogeniser). To this was added dropwise 4 ml of aqueous sodium bicarbonate solution (20 mg/ml). A further 40 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

Figure 18:
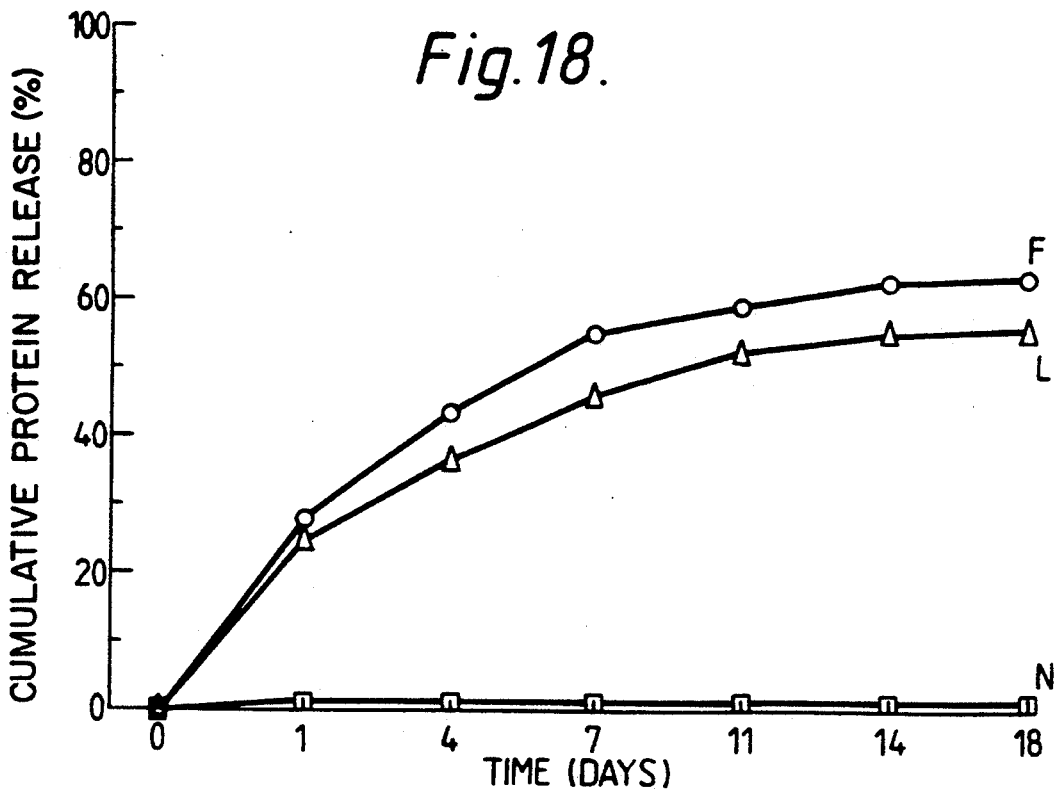
FIG. 18 shows the cumulative release PEG 5000 [Met$^{-1}$, Arg$^{11}$, Ser$^{17,27,60,65}$]hu G-CSF from 50% d,l-lactide/50% glycolide copolymer continuous release pharmaceutical compositions F (see Example 4), L (see Example 26) and N (Comparative Example 6), composition F being prepared by the glacial acetic acid process and compositions L and N being prepared by an aqueous process.

120.5 mg of the sodium salt of the polymer was dispersed in 2 ml of distilled water. 3.478 ml of an aqueous solution of PEG 5000 [Met$^{-1}$, Arg$^{11}$, Ser$^{17,27,60,65}$]hu G-CSF (11.5 mg/ml) added to the polymer salt suspension. A further 4×0 5 ml aliquots of distilled water were used to rinse the glassware. The solution was immediately frozen in a bath of dichloromethane/Drikold and freeze dried overnight. The freeze dried powder was mixed thoroughly using a hydraulic press with plattens heated to 90° C., and was then moulded at this temperature to give a slab 1 mm thick. The slab was cut into depots weighing approximately 84 mg. The depots were then placed in plastic vials containing 2 ml of OXOID phosphate buffered saline, 0.02% sodium azide and stored at 37° C. At regular intervals the aqueous medium was removed and replaced by fresh buffer. Release of PEG 5000 [Met$^{-1}$, Arg$^{11}$, Ser$^{17,27,60,65}$]hu G-CSF was determined by hplc analysis of the medium and cumulative protein release calculated. Cumulative protein release for formulation L is shown in FIG. 18.

COMPARATIVE EXAMPLE 5

Continuous release pharmaceutical composition containing [Met$^{-1}$, Glu$^{15}$, Ser$^{17,27,28}$, Ala$^{26,28}$, Lys$^{30}$, ]hu G-CSF alone - Aqueous process, Formulation M (protein at 20% loading)

4.0g of polylactide (50 weight % d,l-lactide/50 weight % glycolide copolymer, weight average molecular weight 7673, polydispersity 2.59) was dissolved in 12 ml of dichloromethane and placed under high shear (Ystral 1500 homogeniser). To this was added dropwise 4 ml of aqueous sodium bicarbonate solution (20 mg/ml). A further 60 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

160.98 mg of the sodium salt of the polymer was dispersed in 2 ml of distilled water. 4.124 ml of an aqueous solution of [Met$^{-1}$, Glu$^{15}$, Ser$^{17,27}$, Ala$^{26,28}$, Lys$^{30}$]hu G-CSF (9.7 mg/ml) was diluted to 50 mg/ml with distilled water and added to the polymer salt suspension. A further 4×0.5 ml aliquots of distilled water were used to rinse the glassware. The solution was immediately frozen in a bath of dichloromethane/-

Drikold and freeze-dried overnight. The freeze dried powder was mixed thoroughly using a hydraulic press with plattens heated to 75° C., and was then moulded at this temperature to give a slab 1 mm thick. The slab was cut into depots weighing approximately 81 mg. The depots were then placed in plastic vials containing 2 ml of OXOID phosphate buffered saline, 0.02% sodium azide and stored at 37° C. At regular intervals the aqueous medium was removed and replaced by fresh buffer. Release of [Met$^{-1}$, Glu$^{15}$, Ser$^{17,27}$, Ala $^{26,28}$, Lys$^{30}$]hu G-CSF was determined by hplc analysis of the medium and cumulative protein release calculated. Cumulative protein release for formulation M is shown in FIG. 17.

COMPARATIVE EXAMPLE 6

Continuous release pharmaceutical composition containing [Met$^{-1}$, Arg$^{11}$, Ser$^{17,27,60,65}$]hu G-CSF.

Formulation N (protein at 20% loading)

2.0g of polylactide (50 weight % d,l-lactide/50 weight % glycolide copolymer, weight average molecular weight 7673, polydispersity 2.59) was dissolved in 8 ml of dichloromethane and placed under high shear (Ystral 1500 homogeniser). To this was added dropwise 2 ml of aqueous sodium bicarbonate solution (20 mg/ml). A further 30 ml of distilled water was added and a fine white dispersion produced. The dichloromethane was removed using a rotary evaporator. The solution was immediately frozen in a bath of dichloromethane/Drikold and freeze dried overnight. This sodium salt of the polymer was subsequently stored under vacuum at room temperature.

159.99 mg of the sodium salt of the polymer was dispersed in 2 ml of distilled water. 3.988 ml of an aqueous solution of [Met$^{-1}$, Arg$^{11}$, Ser$^{17,27,60,65}$]hu G-CSF (10.03 mg/ml) was diluted to 5.0 mg/ml with distilled water and added to the polymer salt suspension. A further 4 ×0.5 ml aliquots of distilled water were used to rinse the glassware. The solution was immediately frozen in a bath of dichloromethane/Drikold and freeze dried overnight. The freeze dried powder was mixed thoroughly using a hydraulic press with plattens heated to 95° C., and was then moulded at this temperature to give a slab 1 mm thick. The slab was cut into depots weighing approximately 81 mg. The depots were then placed in plastic vials containing 2 ml of OXOID phosphate buffered saline, 0.02% sodium azide and stored at 37° C. At regular intervals the aqueous medium was removed and replaced by fresh buffer. Release of [Met$^{-1}$, Arg$^{11}$, Ser$^{17,27,60,65}$]hu G-CSF was determined by hplc analysis of the medium and cumulative protein release calculated. Cumulative protein release for formulation N is shown in FIG. 18.

EXAMPLE 27

Continuous release pharmaceutical composition PEG5000 human calcitonin

A. Glacial Acetic Acid Process (protein at 5.0% w/w loading)

396.23 mg of polylactide (50 weight % d,l-lactide/50 weight % glycolide copolymer, weight average molecular weight 10691, polydispersity 1.75) were dissolved in 4.0 ml of anhydride-free glacial acetic acid. 2.955 ml of an aqueous solution of PEG 5000 human calcitonin (8.46 mg/ml) were freeze-dried and then dissolved in a further 2.0 ml of the glacial acetic acid. The two solutions were mixed and a further 4 ×1.0 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 75° C. and was then extruded via a 16 gauge port. The extrudate was cut into depots weighing approximately 10 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 human calcitonin was determined by HPLC analysis of the medium and cumulative protein release calculated (see Table 2 below).

B. Aqueous Process 5.0 g of polylactide (50 weight % d,l-lactide/50 weight % glycolide copolymer, weight average molecular weight 10691, polydispersity 1.75) were dissolved in 20.0 ml of dichloromethane and placed under high shear (Ystral 1500 homogeniser). To this were added, dropwise 5.00 ml of an aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use.

392.62 mg of the sodium salt of the polymer were dispersed in 4.0 ml of distilled water. 2,955 ml of an aqueous solution of PEG 5000 human calcitonin (8.46 mg/ml) were freeze-dried and then dissolved in a further 2.0 ml of distilled water. The solution was added to the suspension and mixed. A further 4×1.0 ml aliquots of the distilled water were used to rinse the glassware. The solution was immediately frozen by dropping into liquid nitrogen and freeze-dried overnight. The freeze-dried powder was mixed thoroughly using a hydraulic press with plattens heated to 60° C., and was then extruded via a gauge 16 port. The extrudate was cut into depots weighing approximately 10 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 human calcitonin was determined by HPLC analysis of the medium and cumulative protein release calculated (see Table 2 below).

TABLE 2

| IN VITRO RELEASE OF PEPTIDE (GAA PROCESS) | | |
| --- | --- | --- |
| DAY | DEPOT A Cum % | DEPOT B Cum % |
| 1 | 15.4 | 10.9 |
| 2 | 15.4 | 10.9 |
| 7 | 15.4 | 10.9 |
| 8 | 56.5 | 41.3 |
| 16 | 66.5 | 57.2 |
| DAY | DEPOT C Cum % | DEPOT D Cum % |
| 1 | 6.9 | 7.9 |
| 2 | 6.9 | 7.9 |
| 7 | 6.9 | 7.9 |
| 9 | 27.9 | 27.9 |
| 16 | 45.4 | 31.6 |
| IN VITRO RELEASE OF PEPTIDE (AQUEOUS PROCESS) | | |
| DAY | DEPOT A Cum % | DEPOT B Cum % |

TABLE 2-continued

| | | |
|---|---|---|
| 1 | 20.9 | 24.7 |
| 2 | 30.5 | 35.6 |
| 7 | 41.5 | 57.1 |
| 8 | 51.3 | 72.3 |
| 16 | 65.0 | 88.3 |

| | DEPOT C Cum % | DEPOT D Cum % |
|---|---|---|
| 1 | 26.3 | 20.5 |
| 2 | 32.0 | 25.2 |
| 7 | 46.6 | 36.4 |
| 8 | 53.9 | 42.2 |
| 16 | 60.6 | 49.9 |

EXAMPLE 28

Continuous release pharmaceutical composition containing unpegylated human calcitonin A. Glacial Acetic Acid Process (protein at 5% w/w loading)

473.50 mg of polylactide (50 weight X d,l-lactide/50 weight % glycolide copolymer, weight average molecular weight 10691, polydispersity 1.75) were dissolved in 4.0 ml of anhydride-free glacial acetic acid. 25.56 mg of a freeze-dried preparation of human calcitonin were also dissolved in a further 2.0 ml of the glacial acetic acid. The two solutions were mixed and a further 4×2.0 ml aliquots of the glacial acetic acid used to rinse the glassware. The solution was immediately frozen by dropping into liquid nitrogen and freeze-dried overnight. The freeze-dried powder was mixed thoroughly using a hydraulic press with plattens heated to 75° C. and was then extruded via a 16 gauge port. The extrudate was cut into depots weighing approximately 10 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of human calcitonin was determined by HPLC analysis of the medium and cumulative protein release calculated. Analyses were performed on days 1, 2, 7, 8 and 16 and no evidence of significant release was detected over this period.

B. Aqueous Process (protein at 5.0% w/w loading)

5.0 g of polylactide (50 weight % d,l-lactide/50 weight % glycolide copolymer, weight average molecular weight 10691, polydispersity 1.75) were dissolved in 20.0 ml of dichloromethane and placed under high shear (Ystral 1500 homogeniser). To this were added, dropwise 5.00 ml of an aqueous sodium bicarbonate solution (20 mg/ml). A further 50 ml of distilled water were added and a fine white dispersion produced. The dichloromethane was then removed using a rotary evaporator. The dispersion was immediately frozen in a bath of dichloromethane/Drikold and freeze-dried overnight. This sodium salt of the polymer was subsequently stored under vacuum at room temperature prior to use. 474.84 mg of the sodium salt of the polymer were dispersed in 4.0 ml of distilled water. 25.65 mg of a freeze-dried preparation of human calcitonin were also dissolved in 2.0 ml of distilled water. The solution was added to the suspension and mixed. A further 4×1.0 ml aliquots of the distilled water were used to rinse the glassware. The solution was immediately frozen by dropping into liquid nitrogen and freeze-dried overnight. The freeze-dried powder was mixed thoroughly using a hydraulic press with plattens heated to 55° C. and was then extruded via a gauge 16 port. The extrudate was cut into depots weighing approximately 10 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of human calcitonin was determined by HPLC analysis of the medium and cumulative protein release calculated. Analyses were performed on days 1, 2, 7, 8 and 16 and no evidence of significant release was detected over this period.

EXAMPLE 29

Continuous release pharmaceutical composition containing PF. G5000 interleukin-2 (PEG 5000 IL-2)

Glacial Acetic Acid Process (protein at 20% w/w loading)

113.42 mg of polylactide (50 weight % d,l-lactide/50 weight % glycolide copolymer, weight average molecular weight 10691, polydispersity 1.75) were dissolved in 2.0 ml of anhydride-free glacial acetic acid 4.88 ml of an aqueous solution of PEG 5000 IL-2 (7.35 mg/ml) were freeze-dried and then dissolved in a further 1.0 ml of the glacial acetic acid. The two solutions were mixed and a further 4×0.5 ml aliquots of the glacial acetic acid used to rinse the glassware. The solution was immediately frozen by dropping into liquid nitrogen, and freeze-dried overnight. The freeze-dried powder was mixed thoroughly using a hydraulic press with plattens heated to 75° C. and formed into depots weighing approximately 30 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of PEG 5000 IL-2 was determined by HPLC analysis of the medium and cumulative protein release calculated (see Table 3 below).

TABLE 3

IN VITRO RELEASE OF PEPTIDE

| DAY | DEPOT A Cum % | DEPOT B Cum % |
|---|---|---|
| 1 | 31.3 | 37.7 |
| 2 | 41.8 | 41.1 |
| 4 | 43.9 | 45.8 |
| 8 | 45.5 | 47.0 |
| 16 | 46.5 | 47.7 |

EXAMPLE 30

Continuous release pharmaceutical composition containing unpegylated interleukin-2 (IL-2)

Glacial Acetic Acid Process protein at 20% w/w loading) 54.90 mg of polylactide (50 weight % d,l-lactide/50 weight % glycolide copolymer, weight average molecular weight 10691, polydispersity 1.75) were dissolved in 4.0 ml of anhydride-free glacial acetic acid. 45.09 mg of a freeze-dried preparation of IL-2 were also dissolved in a further 1.0 ml of the glacial acetic acid. The two solutions were mixed and a further 4×0.5 ml aliquots of the glacial acetic acid used to rinse the glassware. The solution was immediately frozen by dropping into liquid nitrogen and freeze-dried overnight. The freeze-dried powder was mixed thoroughly using a hydraulic press with plattens heated to 80° C., and was then formed into depots weighing approximately 30 mg. The depots were then placed in plastic vials containing 2.0 ml of 0.02% w/v sodium azide solution in OXOID phosphate-buffered saline and stored at 37° C. At regular intervals, the aqueous medium was removed and replaced by fresh buffer. Release of IL-2 was determined by HPLC analysis of the medium and cumulative protein release calculated. Analyses were performed on days 1,2,4,8 and 16 and no evidence of significant release was detected over this period.

REFERENCE EXAMPLE 1

Preparation of [Met$^{-1}$]human G-CSF modified with methyl polyethylene glycol 5000

Figure 2:
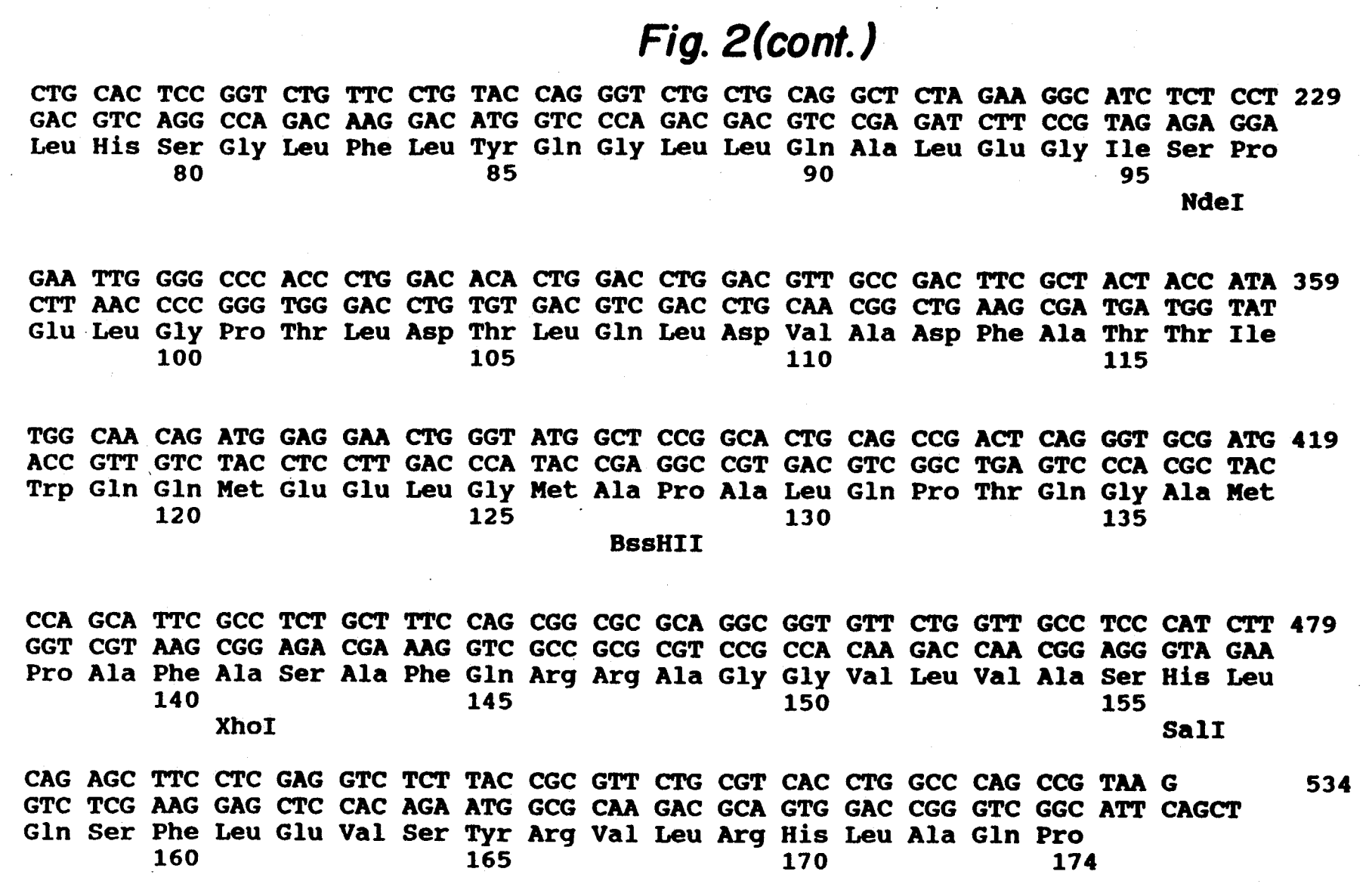

A. Preparation of [Met$^{-1}$]human G-CSF a) Preparation of a synthetic gene for [Met$^{-1}$]human G-CSF A DNA sequence (FIG. 2 and SEQ ID No 45) encoding the amino-acid sequence of the polypeptide of FIG. 2 (human G-CSF) was designed according to the following considerations:
1) Single—stranded cohesive termini to allow ligation at suitable sites in a plasmid.
2) A series of restriction endonuclease sequences throughout the gene to facilitate subsequent genetic manipulation.
3) Translation termination codon.
4) Codons at the 5'-end of the coding region were normally chosen to be A/T rich. Other codons were normally chosen as those preferred for expression in E.coli.

The gene was assembled from the 18 oligonucleotides (SEQ ID No.1 - SEQ ID No.18) shown hereinafter.

Preparation of Oligonucleotides

The oligonucleotide sequences shown hereinafter were prepared on an Applied Biosystems 380A DNA synthesiser from 5'-dimethoxytrityl base-protected nucleoside-2-cyanoethyl-N,N-diisopropylphosphoramidites and protected nucleosides linked to controlled-pore glass supports on a 0.2 micro mol scale, according to protocols supplied by Applied Biosystems Inc.

Alternatively, the oligonucleotide sequences may be prepared by manual methods as described by Atkinson and Smith in 'Oligonucleotide Synthesis, a Practical Approach' (M. T. Gait, Editor, IRL Press, Oxford, Washington DC, pages 35-81).

In detail, the preparation of the oligonucleotide sequences by use of the Applied Biosystems 380A DNA synthesiser was effected as follows:

Each oligonucleotide, after cleavage from the solid support and removal of all protecting groups, was dissolved in water (1 ml). A solution of 3 M sodium acetate (pH5.6; 40 μl) and ethanol (1 ml) was added to the oligonucleotide solutions (400 μl) and the mixtures stored at −70° C. for 20 hours. The resulting precipitates were collected by centrifugation (13,000rpm for 10 minutes) and the pellets washed with ethanol:water (7:3) (200 μl) then dried briefly in vacuo and dissolved in water (15 μl) and 10 μl of a formamide/dye mix. (10mM NaOH, 0.5 mM EDTA, 0.01% Bromophenol Blue, 0.01% xylene cyanol, 80% formamide.

The oligonucleotides were purified on a 10% polyacrylamide gel in 50 mM Tris-borate (pH8.3) containing 8.3 M urea. Oligonucleotides of correct length were identified by UV shadowing (Narang et al, 1979 in Methods in Enzymology Vol 68, 90-98)—normally the most prominent band—excised from the gel and electroeluted in 5mM tris-borate (pH 8.3) at 300mV for 3–4 hours. The aqueous solutions were concentrated to about 200 μl by treatment with n-butanol (mix, spin and removal of the upper organic layer). The purified oligonucleotides were precipitated at −70° C. for 20 hours from a 0.3 M sodium acetate solution by addition of ethanol (2.5 volumes).

Assembly of gene

Oligonucleotides SEQ ID No2—SEQ ID No 17 (400pM of each) [set out hereinafter] were phosphorylated with T4 polynucleotide kinase (3.6 units) for 2 hours at 37° C. in 25 μl of a solution containing ATP (800pM containing 25pM gamma- $^{32}$p ATP), 100 μM spermidine, 20mM MgCl$_2$, 50mM Tris-HCl (pH9.0) and 0.1 mM EDTA. The solutions were heated at 100° C. for 5 minutes to terminate the reactions, then mixed in pairs as shown in Table 1 to give duplexes A to I (Oligonucleotides SEQ ID No 1 and SEQ ID No 18 (400mM in 25 μl) were used unphosphorylated). 0.3 M Sodium acetate (pHS.6, 200 μl) and ethanol (850821) were added and the duplexes precipitated at −20° C. for 20 hours. The resulting precipitates were collected by centrifugation and washed with ethanol:water (7:3) then dissolved in water (50 μl). The pairs of oligonucleotides were annealed together by first heating the solutions to 100° C. for 2 minutes in a boiling water bath. The bath was then allowed to cool slowly to 40° C. (about 4 hours). Solutions containing 3 pairs of duplexes were combined as shown (see Table 1), to give groups I to III lyophilised and dissolved in 30 μl of a solution containing T4 DNA ligase (1 unit; BRL), 50mM Tris (pH7.6), 10mM magnesium chloride, 5% (w/v) PEG 8000, 1 mm ATP, 1 mm DTT. (BRL, Focus Vol 8 no 1 Winter 1986) and the DNA ligated at 30° C. for 5 minutes followed by 20 hours at 16° C. 3 M Sodium acetate (20 μl) and water (150Ul) was added and the product precipitated by addition of ethanol (750 μl) and cooling to −20° C. for 20 hours. The precipitate was collected by centrifugation and washed with ethanol (1 ml) then dissolved in water (15 μl) and formamide/dye mix (10 μl) and purified on a 10% polyacrylamide gel in 50mM Tris-borate (pH8.3), 1 mM EDTA and 8.3 M urea. Bands for strands of appropriate lengths (173–186 bases) were identified by autoradiography and isolated together by electroelution from a single gel slice as described above for individual oligonucleotide sequences. The DNA strands were annealed by first heating an aqueous solution (50 μl) at 100° C. for 2 minutes, then allowing it to cool to 40° C. over 4 hours. Groups I, II and III were ligated together essentially as described for the group preparation to give as the product, the gene sequence shown in FIG. 8. After precipitation, the gene was phosphorylated with T4 polynucleotide kinase as described previously for individual oligonucleotides, then dissolved in water (20 μl).

TABLE 1

| DUPLEX | OLIGONUCLEOTIDE | NUMBER OF BASES IN TOP STRAND | BOTTOM STRAND |
|---|---|---|---|
| A | SEQ ID No 1 + SEQ ID No 2 | 62 | 64 |
| B | SEQ ID No 3 + SEQ ID No 4 | 60 | 60 |
| C | SEQ ID No 5 + SEQ ID No 6 | 48 | 51 |
| D | SEQ ID No 7 + SEQ ID No 8 | 63 | 60 |
| E | SEQ ID No 9 + SEQ ID No 10 | 63 | 63 |
| F | SEQ ID No 11 + SEQ ID No 12 | 60 | 63 |

TABLE 1-continued

| DUPLEX | OLIGONUCLEOTIDE | NUMBER OF BASES IN TOP STRAND | BOTTOM STRAND |
|---|---|---|---|
| G | SEQ ID No 13 + SEQ ID No 14 | 63 | 60 |
| H | SEQ ID No 15 + SEQ ID No 16 | 60 | 60 |
| I | SEQ ID No 17 + SEQ ID No 18 | 55 | 53 |
| I | A + B + C | 170 | 175 |
| II | D + E + F | 186 | 186 |
| III | G + H + I | 178 | 173 | b) Cloning of the synthetic gene for [Met$^{-1}$]human G-CSF

The synthetic gene described above, was cloned into the plasmid vector, pSTP1 (Windass et al, Nucleic Acids Research (1983) Vol 10, p6639).

For vector preparation, 10 μg of STP1 was dissolved in water (37.5 μl) and 10 ×B restriction buffer (4.5 μl) (BCL). the restriction endonuclease SalI (3 μl) (BCL, 8 units/μl) was added and the mixture incubated at 37° C. for 1 hour until linearised plasmid was predominant over supercoiled and nicked circular forms. The DNA was precipitated with ethanol at 4° C. for 30 minutes, washed with ethanol:water (7:3) then dissolved in water (39.5 μl), 10X H buffer (4.5 μl) (BCL). The restriction endonuclease EcoRI (1 μl) (BCL, 90 units/μl) was added and the mixture incubated at 37° C. for 1 hour until the large EcoRI-SalI fragment was predominant. The DNA was precipitated at −20° C. for 20 hours, washed with ethanol:water (7:3) then dissolved in water (20 μl)

The large EcoRI - SalI fragment was purified on a 1% preparative agarose gel and electroeluted and precipitated as described previously, then dissolved in water (20 μl). For ligation of the synthetic gene, a mixture of vector DNA (2 μl of the EcoRI - SalI fragment solution), synthetic gene (5 μl of the aqueous solution described previously, 5X ligase buffer (6 μl -250mM Tris pH7.6 50mM MgCl$_2$, 25% W/V PEG8000, 5 MM ATP, 5mM DTT exBRL) water (15 μl) and T4 DNA ligase (2 μ, 1U/μl) was incubated at 16° C. for 4 hours. The DNA mix was used directly (either 1 μl of neat ligation mix or 2 μl of ligation mix diluted 5X with water) to transform E. coli strain HB101. The DNA mixture (1 or 2 μl) was added to competent E. coli HB101 cells (20 μl, BRL) on ice and the mixture incubated on ice for 45 min then heat shocked at 42° C. for 45 seconds. After 2 min on ice, 100 μl of SOC buffer (Bactotryptone 2%; Yeast Extract 0.5%; NaCl 10mm; KC12.5 MM; MgCl$_2$, MgSO$_4$ 20mm (10mm each); glucose 20mm) was added and the mixture incubated at 37° C. for 1 hour. Aliquots of suspensions were plated onto l plates with 50 μl/ml ampicillin. Transformants were screened for the presence of cloned synthetic gene by colony hybridisation analysis using standard methods described in "Molecular Cloning: A Laboratory Manual" by Maniatis et al (Cold Spring Harbor) and in UK Patent Application No 8502605. A total of 100 colonies were streaked onto filters (Schleicher and Schuell), grown at 37° C. for 20 hours, lysed and baked. The filter was hybridised at 65° C. for 20 hours with a radioactive probe prepared from oligonucleotide sequence SEQ ID No 1 (see hereinafter) by use of a random-label kit (Pharmacia). Five colonies 1–5 giving a positive hybridisation signal were grown up in L broth at 37° C. for 20 hours on a small scale (100 ml) and plasmid DNA prepared by centrifugation in a caesium chloride gradient essentially as described in "Molecular Cloning; A Laboratory Manual" by Maniatas et al (Cold Spring Harbor).

The DNA was sequenced by the standard dideoxy chain-termination method as described by Sanger et al in Proc. Nat. Acad Sci. USA 7–4, 5463–5467 (1977) using a Sequenase (Trade Mark) kit (United States Biochemical Corporation). Oligonucleotides SEQ ID No 19 to SEQ ID No 23 (see hereinafter) were used as sequencing primers.

TABLE 2

| CODE | PRIMING SITE |
|---|---|
| SEQ ID No 19 | 214–234 top strand |
| SEQ ID No 20 | 333–353 top strand |
| SEQ ID No 21 | 375–395 bottom strand |
| SEQ ID No 22 | 207–227 bottom strand |
| SEQ ID No 23 | 69–93 bottom strand |

The plasmid DNA from clone 5 contained the DNA sequence shown in FIG. 6, The plasmid (pAG88) was used to transform competent cells of the following E. coli strains by standard procedures:
HB101
CGSC 6300 (hereinafter also referred to a MSD 522)

The E. coli strains HB 101 and MSD 522 (CGSC 6300) are freely available. Thus for example they may be obtained from the E. coli Genetic Stock Centre, Yale University, USA. Moreover E. coli HB 101 may additionally be obtained from for example BRC supplied by GIBCO Limited (Unit 4, Cowley Mill Trading Estate, Longbridge Way, Uxbridge UB8 2YG, Middlesex, England) or from GIBCO Laboratories, Life Technologies Inc., 3175 Staley Road, Grand Island, N.Y. 14072, USA. The genotype of strain HB101 is described in the aforementioned "Molecular Cloning - A Laboratory Manual" as Sup E44 hsd S20 (r$_B^-$ m$_B^-$)rec A 13 ara-14 F$^-$leu 6 thi-1 proA2 lac Y1 gal K2 rps L20 xyl$^{-5}$ mtl−1. The genotype of MSD 522 (CGSC 6300) is set out in Reference Example 12.

c) Cloning of the gene for [Met$^{-1}$]human G-CSF into an expression vector

The gene described above was cloned into the plasmid pICI 0020 as described in Reference Example 3(c) to yield the expression plasmid pICI 1056.

d) Fermentation

The plasmid pICI 1056 was transformed and fermentation effected as described in Reference Example 3(e) to achieve expression of [Met$^{-1}$]human G-CSF.

e) Purification

Purification was effected as described in the second purification procedure developed to yield larger quantities of [Met$^{-1}$]hu G-CSF set out on pages 48 and 49 of PCT Patent Publication No. WO 87/01132 with final dialysis being effected against phosphate buffered saline.

B. Preparation of [Met$^{-1}$]hu G-CSF modified with Methyl polyethylene glycol 5000.

A solution of [Met$^{-1}$]hu G-CSF (300 mg) prepared as described in A above was concentrated to 8 mg/ml in 20mM sodium acetate, 37mM sodium chloride pH5.4 by ultrafiltration on an Amicon YM10 membrane (MW cut off 10kDa). To this solution was added an equal volume of 0.8 M sodium borate pH8.8 followed by methyl polyethylene glycol p-nitrophenyl carbonate approx MW 5000 (Sigma Chemical Co Ltd) (100 equivalents per mole [Met$^{-1}$]hu G-CSF) dissolved in water. The reaction was allowed to proceed at 20° C. for 3 hours with gentle stirring and quenched by the addition of 1 M ethanolamine hydrochloride pH8.0 (10 equivalents per mole of activated methyl polyethylene glycol). The reaction mixture was immediately adjusted to pH5.4 by titration with 1 M acetic acid and diluted to 500 ml with 20mM sodium acetate, 100mM NaCl, pH5.4. The mixture was diafiltered against 10 liters of the same buffer using an Amicon CH2A-1S spiral cartridge system fitted with an SIY30 membrane (MW cut off 30 kDa) until the yellow p-nitrophenol was no longer visible in the retentate. The retentate was concentrated to about 300 ml and placed in an Amicon 8400 stirred cell fitted with a YM30 (30kDa cut off) membrane. The retentate was concentrated to 50 ml and rediluted to 300 ml with 20mM sodium acetate, 100mM NaCl, pH5.4. This procedure was repeated four times and the product finally concentrated to about 25 ml. This concentrate was chromatographed on a column (5×90cm) of Ultrogel AcA54 equilibrated with 20mM sodium acetate, 100mM NaCl pH5.4 Fractions containing the modified protein were identified by monitoring protein at 280nm and methyl polyethylene glycol by iodine/potassium iodide titration (CR Acad Sci. Paris 274 1617 1972) pooled and exhaustively dialysed against water. The final product was concentrated to greater than 11.5 mg/ml by ultrafiltration on an Amicon YM30 membrane, filtered through a 0.22Um filter under sterile conditions and stored at 4° C. for further studies SDS-PAGE on the final modifed product indicated that no unreacted [Met$^{-1}$]hu G-CSF remained, all the product running as a high MW streak. Titrations of filtrates and retentates with iodine/potassium iodide showed that repeated diafiltration at pH 5.4 on a YM30 membrane (MW cut off 30kDa) effectively removed all non-protein bound methyl polyethylene glycol. The final product contained about 4 moles of methyl polyethylene glycol covalently bound per mole protein. The specific activity of unmodified derivative, $0.8 \times 10^9$ U/mg, fell to $0.2 \times 10^9$ U/mg (25%) in the modified product. The product was completely stable and showed no change in specific activity in solution at up to 10 mg/ml (by protein) at 37° C. over 14 days.

In this Reference Example the pH of the solution of [Met$^{-1}$]hu G-CSF is carefully controlled prior to pegylation in order to avoid or at least minimise dimerisation.

REFERENCE EXAMPLE 2

Preparation of [Met$^{-1}$] human G-CSF modified with methyl polyethylene glycol 5000.

Reference Example 1 was repeated except that the purification of [Met$^{-1}$]hu G-CSF was effected as follows: Frozen cell paste (500 g) was lysed and the crude pellet fraction separated, washed and solubilised as in Reference Example 4 (see hereinafter). The Sarkosyl-soluble extract was clarified by centrifugation at 30,000 xg for 30 minutes.

To 1 liter of supernatant was added dropwise 1 liter of acetone with stirring at 4° C. The precipitated protein was collected after 10 minutes by centrifugation at 15,000 xg for 30 minutes and the supernatant discarded. The pellet was resolubilised in 40mM sodium acetate, 6 M guanidine hydrochloride pH4.0 (500 ml) using a Polytron PT10-35 homogeniser fitted with a PTA 20 probe and allowed to stir for 1 hour at 4° C. prior to exhaustive dialysis in collodion tubing (Spectrapor, MW cut off 6–8kDa) against 20mM sodium acetate, pH5.4. The precipitated protein was removed by centrifugation at 15,000xg for 30 min and the supernatant loaded on a 50 ml column of CM cellulose (Whatman CM52) equilibrated with 20mM sodium acetate pH5.4. The column was washed with the same buffer until the E$_{280}$ of the eluant fell to baseline, then washed with four column volumes of 20mM sodium acetate pH5.4 containing 20mM NaCl. The product fraction containing [Met$^{-1}$]hu G-CSF was eluted by 37mM NaCl in 20mM sodium acetate, pH5.4, fractions pooled and either modified immediately with methyl polyethylene glycol 5000 or stored at −20° C. until required for further studies.

REFERENCE EXAMPLE 3

Preparation of [Met$^{-1}$, Ser$^{17,27}$]human G-CSF modified with methyl polyethylene glycol 5000

Preparation of human [Met$^{-1}$, Ser$^{17,27}$]G-CSF

The procedure for steps A a) and A b) in Reference Example 1 was repeated with the following modifications:

Oligonucleotides SEQ ID Nos 24, 25, 26 and 27 (as detailed hereinafter) replace SEQ ID Nos 1, 2, 3 and 4 respectively.

c) Cloning of the gene for human [Met$^{-1}$, Ser$^{17,27}$]G-CSF into an expression vector The gene described above (see FIG. 3) was cloned into plasmid vector pICI0020. This vector is a pAT153 based plasmid in which the 651 bp EcoRI-AccI region is replaced by a 167 bp EcoRI - ClaI fragment consisting of:

(1) a synthetic *E. coli* trp promoter and trp leader ribosome binding site
(2) a translation initiation codon
(3) a multiple restriction enzyme recognition sequence derived from M13mp18, containing sites for KpnI, BamHI, XbaI, SalI, PstI, SphI and HindIII
(4) a synthetic transcription termination sequence The DNA sequence of this region is shown in FIG. 1 (see also SEQ ID No 44).

The pICI0020 expression vector was digested to completion with KpnI (BCL) in 10mM Tris HCl (pH7.5), 10mM magnesium chloride. The DNA was precipitated with ethanol at −20° C. from a solution containing 0.3 M sodium acetate and then the 3'- sticky ends were removed by treatment with T4 DNA polymerase for 10 minutes at 37° C. as follows:

DNA (1 μg) in water (16 μl)
10 X T4 polymerase buffer (2 μl)
0.33 M Tris acetate pH7.9
0.1 M Magnesium acetate
0.66 M Potassium acetate
5 mM dithiothreitol
1 mg/ml bovine serum albumin (BSA PENTAX fraction V)
2 mM dNTP mixture (1 μl)
T4 DNA polymerase (1 μl; 2.5 units/μl BCL)

Water (80 μl) was added and the mixture extracted with phenol/chloroform (100 μl) and then with chloroform (100 μl). The DNA was precipitated with ethanol (250 μl) at −20° C. after addition of 3 M sodium acetate (10 μl) then digested to completion with SalI (BCL) in 150mM NaCl, 10mM MgCl$_2$ and 10mM Tris HCl (pH7.5). The Kpn-blunt ended to SalI vector was purified from a 0.7% agarose gel and isolated by use of Geneclean (trademark) following the manufacturer's (Bio101, USA) recommended procedure.

The synthetic gene was isolated from the pSTP1 vectors as follows. The vectors were digested with ScaI and SalI (both from BCL) in 100mM NaCl, 10mM MgCl$_2$ and 10mM Tris HCl (pH7.5). The 530 bp fragment was purified from a 0.7% agarose gel and isolated by use of Geneclean (trademark) following the manufacturer's (Bio101) recommended procedure.

For ligation, a mixture of the ScaI - SalI gene fragment (50 ng) and the pICI0020 vector fragment (100ng) in 20 µl of a solution containing 50mM Tris HCl (pH7.6), 10mM MgCl$_2$, 1 mM ATP, 1 mM DTT, 5% w/v PEG 8000 and T4 DNA ligase (2 units; BRL) were incubated at 16° C. for 20 hours. The resulting mixture was used to transform competent E. coli HB101 cells (as supplied by BRL) as described herein. Transformants were selected for by growth on L-agar plates containing 50 µg/ml ampicillin and screened for the presence of the gene by colony hybridisation with a 32p labelled probe (SEQ ID No 24) as described herein. Plasmid DNA was prepared from 6 positively hybridising colonies, purified by centrifugation in a caesium chloride gradient and the sequence confirmed by dideoxy sequencing as described herein.

The plasmid containing this gene was designated pICI 1080.

d) Subcloning of an expression cassette containing a gene for [Met$^{-1}$, Ser17,27]G-CSF into M13mp18.

The following subcloning was effected to provide a starting point for preparation of the G-CSF derivatives detailed in Reference Examples 7 and 8.

Plasmid DNA from pICI1080 (purified by caesium chloride density centrifugation) was digested to completion with EcoRI and SalI (BCL) according to the manufacturer's instructions. The small EcoRI-SalI fragment containing the trp promoter and [Met$^{-1}$, Ser$^{17,27}$]G-CSF gene was isolated from a 0.7% agarose gel by use of Geneclean (trademark). This fragment was cloned into an EcoRI-SalI cut M13mp18 vector (DNA supplied by Amersham International; enzymes from BCL). The fragments were ligated together in 5x BRL ligation Buffer using BRL T4 DNA ligase (described previously). The ligation mix was used to transfect competent E. coli TG1 cells (made competent according to the calcium chloride method of Mandel and Higa described in Molecular Cloning—A Laboratory Manual—Maniatis et al Cold Spring Harbor). The transfected cells were suspended in TY top agar containing 2% X-Gal in DMF and 200 µl log phase E. coli TG1 cells and were plated on 2x TY agar plates (TY top agar - 8 g Bactotryptone, 5 g Yeast Extract, 5 g NaCl, 3.75 g Bacto-agar in 500 µl sterile H$_2$O; TY plates - 8 g Bactotryptone, 5 g Yeast-extract, 5 g NaCl, 7.5 g Bactoagar in 500 ml sterile H$_2$O.)

Four white plaques were picked into 4×2 ml 1% E. coli TG1 cells in TY broth (Sg Bactotryptone, 5 g Yeast extract, 5 g NaCl in 500 ml sterile H$_2$O) aliquots and grown for 6 hours at 37° C. The 2 ml cultures were split into 0.5 ml and 1.5 ml aliquots. The bacteria were centrifuged out of solution in an Eppendorf, (trademark) microfuge and the supernatents were transferred to sterile eppendorf (tradmark) tubes. The 0.5 ml aliquots were stored at −20° C. as phage stocks. The 1.5 ml aliquots were used to prepare single stranded DNA following the method in the Amersham International M13 sequencing handbook (see below). These DNA samples were then sequenced using oligonucleotides SEQ ID No 22, SEQ ID No 23 and M13 Universal sequencing primer. The reactions were carried out using the Sequenase kit (trademark) according to the manufacturers instructions. All 4 clones had the correct DNA sequence for [Ser$^{17,27}$]G-CSF.

Large-scale single stranded DNA preparation

For single stranded DNA preparations of between 200–500 µg of DNA/ml, the method in the Amersham International "Oligonucleotide Directed Mutagenesis" was used. A detailed procedure is carried out as follows:

LARGE - SCALE SINGLE STRANDED DNA PREP

A. Preparation of 1 ml phage stock

1. Pick a single TG1 E.coli colony from a glucose/minimal medium plate. Grow overnight in 10 ml 2 ×TY medium, shaken at 37° C. Add 10 µl to 20 ml of fresh medium, and shake at 37° C. for 3 hours.

2. Inoculate 1 ml 2 ×TY medium in a 10 ml sterile culture tube with 100 µl of 3 hour culture from step 1.

3. Inoculate the 1 ml culture with a recombinant plaque.

4. Incubate for 4 hours with shaking at 37° C. Transfer to a microcentrifuge tube.

5. Centrifuge for 5 minutes at ambient temperature. Pour supernatent into a fresh tube.

Store overnight at 4° C. Set up an overnight culture of TG1 E.coli for the next stage.

B. Growth of 100 ml phage culture.

1. Inoculate 100 ml 2 ×TY medium with 1 ml of overnight TG1 culture and shake at 37° C. to an O.D $_{500}$ of 0.3 .

2. Add the 1 ml phage supernatant from A5 (above) to the 100 ml culture.

3. Incubate for 5 hours with shaking at 37° C. Transfer to centrifuge tubes.

4. Centrifuge at 5000 ×g for 30 minutes at 4° C.

5. Transfer supernatant to a clean centrifuge tube. Take care not to carry over any cells (retain bacterial pellet for RF DNA preparation)

6. Add 0.2 volumes of 20% w/v PEG 6000 in 2.5 M NaCl to the supernatent. Mix well and then leave to stand for 1 hour at 4° C.

7. Centrifuge at 5000 ×g for 20 minutes at 4° C. Dscard supernatent.

8. Centrifuge at 5000 ×g for 5 minutes, and remove all remaining PEG/NaCl with a drawn out Pasteur pipette.

9. Resuspend the viral pellet in 500 µl water (double distilled) and transfer to a microcentrifuge tube (1.5 ml).

10. Centrifuge for 5 minutes in a microcentrifuge to remove any remaining cells. Transfer the supernatent to a fresh microcentrifuge tube.

11. Add 200 µl 20% PEG 12.5 M NaCl to the supernatent mix well then leave to stand at ambient temperature for 15 minutes.

12. Centrifuge for 5 minutes, discard supernatant.

13. Centrifuge for 2 minutes. Carefully remove all traces of PEG/NaCl with a drawn out Pasteur pipette.

14. Resuspend the viral pellet in 500 µl double distilled water.

15. Add 200 µl phenol saturated with 10mM Tris HCl pH8.0, 1 mM EDTA. Vortex briefly.

16. Stand tube for 15 minutes at room temperature.

17. Centrifuge for 3 minutes.

18. Transfer supernatent to fresh tube.

19. Repeat steps 15-18.

20. Add 500 µl chloroform and extract aqueous phase twice.

21. Add 50 μl 3 M sodium acetate and 1 ml absolute ethanol. Mix.

22. Place in a dry ice and ethanol bath for 20 minutes.

23. Centrifuge for 15 minutes.

24. Wash each pellet with 1 ml −20° C. ethanol. Pour off.

25. Vacuum dry pellet and raise in 50 μl double distilled water. This procedure yields 100–200DE single stranded DNA.

e) Fermentation pICI 1080 was transformed into *E. coli* strain MSD 522 (CGSC 6300) (referred to in Reference Example 1A(b)) and the resultant recombinants purified and maintained on glycerol stocks at −80° C.

An aliquot of the culture was removed from stock and streaked onto agar plates of L-ampicillin to separate single colonies after overnight growth at 37° C. A single desired colony was removed and resuspended in 10 ml L-ampicillin broth and 100 μl immediately inoculated into each of 10 250 ml Erlenmeyer flasks containing 75 ml L-ampicillin broth. After growth for 16 h at 37° C. on a reciprocating shaker the contents of the flasks were pooled and used to inoculate a fermenter containing 20 L LCM50 growth medium.

Composition of LCM50

| | Made up of distilled water g/l |
|---|---|
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.00 |
| Yeast Extract (Difco) | 10.00 |
| Glycerol | 35.00 |
| L-Leucine | 2.5 |
| L-Threonine | 0.9 |
| MgSO$_4$. 7H$_2$O | 0.5 |
| CaCl$_2$. 2H$_2$O | 0.03 |
| Thiamine | 0.008 |
| FeSO$_4$/Citric Acid | 0.94/0.02 |
| Trace element solution (TES) | 0.5 ml |

Fermentations were then carried out at a temperature of 37° C. and pH, controlled by automatic addition of 6 M sodium hydroxide solution, of pH 6.7. The dissolved oxygen tension (dOT) set point was 50% air-saturation and was initially controlled by automatic adjustment of the fermenter stirred speed. Air flow to the fermenter, initially 20L/min, corresponding to 1 volume per volume per minute (VVM) was increased to 50 L/min (2.5 VVM) when the fermenter stirrer speed approached 80–90% of its maximum. Since the oxygen transfer rate (OTR) of the fermenters was unable to meet the oxygen uptake rate (OUR) of the bacteria at a cell density greater than that corresponding to an OD$_{550}$ of 50 under the conditions described, dOT in the fermenter at cell densities greater than this was maintained at 50% air-saturation by restricting bacteria oxygen uptake rate. This was achieved by formulating the medium to become carbon-limited at OD$_{550}$ of 50 and then supplying a feed of the limiting carbon source, together with ammonium sulphate and yeast extract, at a rate which restricted bacterial growth rate.

Fermentations were performed for 16h and during that time samples were taken for measurement of optical density (OD$_{550}$), cell dry weight and accumulation of G-CSF within the cells. G-CSF accumulation was measured by scanning Coomassie blue stained SDS-PAGE gels of whole cell lysates of the sampled bacteria as is well known in the art.

When OD550 reached 25, casein hydrolysate solution (100 g/l Oxzoid L41) was pumped into the fermenters at a rate of 1.5 g/l/h.

When OD$_{550}$ reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation with the fermenter stirred at ca 80% of its maximum. After ca 13-14h this fed-batch feed has replaced with a second feed containing glycerol (715 g/L) and ammonium sulphate (143 g/L) only. Casein hydrolysate feeding was maintained at 1.5 g/L/h throughout. After approximately 16 hours, when microscopic examination of the culture showed the presence of large inclusion bodies within a majority of the cells, bacteria were harvested on a Sorval RC3B centrifuge (7000 g, 30 min., 4° C) and stored frozen at minus 80° C.

f) Purification

Frozen cell paste (500 g) was resuspended at 4° C. in 50mM Tris HCl, 25mM EDTA, pH8.0 (5 liters) using a Silverson model AXR homogeniser. The suspension was lysed by passing three times through a Manton-Gaulin homogeniser at 6000psi and centrifuged at 5000×g for 30 minutes in a Sorvall RC3C centrifuge using a H6000A rotor. The supernatant was discarded and the pellet fraction stored at −20° C before further purification.

The pellet fraction (60–100 g) was thawed and resuspended in 1% w/v deoxycholic acid (sodium salt) in 5mM EDTA, 5mM dithiothreitol, 50mM Tris HCl, pH9.0 (1200 ml) containing 1 mg/ml of sodium azide using a Polytron homogeniser with a PTA 20 probe at speed setting 5. The suspension was mixed for 30 minutes at room temperature and centrifuged at 6500×g for 30 minutes in a Sorvall RCSC centrifuge using a GSA rotor. The supernatant was discarded and the pellet was retreated twice in the same manner. The pellet was next twice resuspended in water (1 liter) and centrifuged at 15,000×g for 20 minutes. The final pellet containing washed inclusion bodies was solubilised in 2% w/v N-lauroyl sarcosine sodium salt (Sarkosyl) in 50mM Tris. HCl, pH 8.0 (150 ml) containing 1 mg/ml sodium azide. Cuptic sulphate was added to 20 μM and the mixture stirred for 16 hours at 20° C. before centrifugation at 30,000×g for 30 minutes in a Sorvall RC5C centrifuge using an SS34 rotor. The supernatant containing the derivative was stored at −20° C. in 50 ml aliquots before further purification.

Solubilised derivative (20 ml) was thawed and passed through a 5 μm filter to remove any particulate material. The filtrate was applied to a column (5×90 cm) of Ultrogel AcA54 equilibrated with 0.3% w/v N-lauroyl sarcosine (sodium salt) in 50mM Tris. HCl, pH 8.0 containing 1 mg/ml sodium azide at 4° C. The column was eluted with the same buffer at a flow rate of 2.5 ml/minute and fractions of 10 ml were collected. Fractions containing the derivative protein were pooled (approximately 100 ml) and stored at 4° C.

Pooled derivative fractions from several columns were combined (300–500 ml) and dialysed against 10 mM sodium phosphate, 150 mM sodium chloride pH 7.4 (3-5 liters) containing 1 mg/ml sodium azide using an Amicon CH2A-1S spiral cartridge diafiltration apparatus equipped with a SLY10 membrane (10kDa cut-off). The retentate was centrifuged at 30,000×g for 30 minutes in a Sorvall RCSC centrifuge using an SS34 rotor, and the supernatant dialysed in Spectrapor 6-8 kDa cut-off dialysis tubing for 40 hours against three changes (8 liters/300 ml of supernatant) of 20mM sodium acetate, 100mM sodium chloride, pH 5.4 containing 1 mg/ml sodium azide. The precipitate which formed was removed by centrifugation at 30,000×g for 30 minutes and the supernatant dialysed for 24 hours against water containing 1 mg/ml sodium azide followed by 72 hours against six changes of water. The final retentate was clarified by centifugation at 30,000×g for 30 minutes and stored frozen at −20° C. (protein concentration about 1 mg/ml) or at 4° C. after freeze drying.

The concentration of N-lauroyl sarcosine (sodium salt) had fallen to below 0,001% w/v after diafiltration and was below the limit of detection (about 0.0001%) of the rpHPLC method used after dialysis against water.

B. Preparation of [Met$^{-1}$, Ser 17,27]hu G-CSF modified with methyl polyethylene glycol 5000

This was prepared as described in Reference Example 7. The final product contained about 4.1 moles of methyl polyethylene glycol covalently bound per mole of protein. The specific biological activity of [Met$^{-1}$, Ser$^{17,27}$]hu G-CSF (14×10$^9$ U/mg) only fell to 2.4×10$^8$ U/mg (17%) after modification. The product was completely stable and showed no change in specific activity in solution at up to 10 mg/ml (by protein) in PBS at 37° C. over 14 days. These results are strikingly similar to those found in Reference Example 7 and indicate the consistency of results obtained with a given arrangement of amino groups.

REFERENCE EXAMPLE 4

Preparation of [Met$^{-1}$, Arg$^{11}$, Ser$^{17,27,60,65}$]human G-CSF modified with methyl polyethylene glycol 5000.

The procedure described in Reference Example 7 was repeated except as follows,

Frozen cell paste (500 g) was resuspended at 4° C. in 50mM Tris. HCl, 25mM EDTA pH8.0 (5 liters) using a Polytron PT6000 homogeniser. The suspension was lysed by passing three times through a Manton-Gaulin homogeniser at 6000 psi and centrifuged at 5000×g for 30 minutes at 4° C. in a Sorvall RC3C centrifuge fitted with an H6000A rotor. The supernatant was discarded and the pellet fraction stored at −20° C. before further purification.

The pellet fraction (200-250 g) was thawed and resuspended in 1% w/v deoxycholic acid (sodium salt) in 5mM EDTA, 5mM dithiothreitol, 50 mM Tris HCl pH9.0 containing 1mg/ml sodium azide (3 liters) using a Polytron PT10-35 homogeniser fitted with a PTA20 probe. The suspension was mixed for 30 minutes at 20° C. and centrifuged at 5000×g for 30 minutes in a Sorvall RC3C centrifuge containing a H6000A rotor. The supernatant was discarded and the pellet was retreated twice in the same manner. The pellet was next twice resuspended in water (3 liters) and centrifuged at 5000×g for 30 minutes. The final pellet containing washed inclusion bodies was solubilised in 2% w/v N-lauroyl sarcosine sodium salt (Sarkosyl) in 50mM Tris. HCl pH8.0 (300 ml) containing 1 mg/ml sodium azide. Cupric sulphate was added to 20 μM and the mixture stirred for 16 hours at 20° C. before centrifugation at 30,000×g in a Sorvall RCSC centrifuge using an SS34 rotor. The supernatant containing the derivative was further purified immediately or stored at −20° C. until required.

Solubilised derivative was adjusted to 15 mg/ml total protein (estimated by E$_{280}$) in 2% w/v Sarkosyl in 50mM Tris.HCl pH8.0 containing 1 mg/ml sodium azide and passed through a 5 μM filter to remove any particulate material. The filtrate was applied in 80 ml aliquots to a column (10×90cm) of Sephacryl S200 HR equilibrated with 0.3% w/v Sarkosyl (sodium salt) in 50mM Tris. HCl pH8.0 containing 1 mg/ml sodium azide at 4° C. The column was eluted with the same buffer at a flow rate of 10 ml/minute and fractions of 40 ml were collected. Fractions containing the derivative protein were pooled and stored at 4° C.

Pooled derivative fractions from several column runs were combined (about 1000 ml) and dialysed against 10 liters 10mM sodium phosphate, 150mM sodium chloride pH7.4 containing 1 mg/ml sodium azide using an Amicon CH2A-IS diafiltration apparatus equipped with a SIY10 membrane cartridge (10 kDa cut-off). The retentate was centrifuged if necessary at 15,000×g for 30 minutes in a Sorvall RCSC centrifuge using a GSA rotor and the clarified retentate dialysed in Spectrapot 6-8 kDa cut-off dialysis tubing for 24 hours against three changes (8 liters/300 ml retentate) of 20mM sodium acetate, 100mM sodium chloride, pH5.4 at 4° C. The precipitate which formed was removed by centrifugation at 15,000×g for 30 minutes and the supernatant dialysed for 48 hours against four changes in water (8 liters/300 ml supernatant). The final retentate was clarified by centrifugation at 15,000×g for 30 minutes and made to 0.1 M sodium borate pH8.0. The purified derivative was modified with methyl polyethylene glycol immediately or stored at −20° C. until required.

REFERENCE EXAMPLE 5

Preparation of human [Met$^{-1}$, Ser$^{17,27}$]G-CSF modified with methyl polyethylene glycol 5000.

The procedure described in part A of Reference Example 3 was repeated except as follows:

The duplex I was phosphorylated with T4 polynucleotide kinase and digested with MstII (10 units) in 1X H buffer (BCL; 30 μl) for 2 hours at 37° C.

Following precipitation with ethanol, the 143 bp EcoRI-MstII fragment was purified on a 10% polyacrylamide gel containing 7 M urea, isolated by electroelution from a gel slice and the DNA strands annealed as described in Reference Example 1.

The synthetic EcoRI-MstII fragment described above was cloned into the plasmid vector pAG88 described in Reference Example 1. For vector preparation, pAG88 (10 μg) was digested with MstII (20 units; BCL) in 1 X H buffer (BCL; 100 μl) for 2 hours at 37° C. The DNA was precipitated with ethanol from 0.3 M sodium acetate at −20° C. then digested with EcoRI (20 units; BCL) in 1 X H buffer (BCL; 100 μl) for 2 hours at 37° C. Following precipitation with ethanol, the large EcoRI-MstII fragment was purified on a 1% agarose gel and purified using Geneclean (trademark) as described by the manufacturer (Bio 101, USA). Ligation of the 143 bp gene fragment into the large EcoRI MstII fragment was carried out as described in Reference Example 1 (b). Colonies containing the synthetic fragment were confirmed by screening with a radioactive probe prepared from oligonucleotide (SEQ ID No 24) and the correct sequence confirmed by DNA sequencing as described in Reference Example 1. The plasmid containing the gene for [Met$^{-1}$, Ser$^{17,27}$]G-

CSF was designated pICI1107 The gene was cloned into expression vector pICI 0020 and purification was effected as described in Reference Example 3.

REFERENCE EXAMPLE 6

Preparation of genes for derivatives of human G-CSF by site-directed mutagenesis The phosphorothioate method of Eckstein and coworkers was used:

Taylor, J W et al Nucleic Acids Research (1985) Vol pp 8749–8764

Taylor, J W et al Nucleic Acids Research (1985) Vol pp 8765–8785

Nakamaye, K et al Nucleic Acids Research (1986) Vol pp 9679–9698

Sayers, J R et al Nucleic Acids Research (1988) Vol pp 791–802

The procedure can be carried out using a kit supplied by Amersham International. The method is outlined below and incorporates changes to the original method with regard to the use of more than one mutagenic oligonucleotide and the incubation temperature for oligonucleotides of greater than 30 bases in length.

1. Annealing mutant oligonucleotide to single stranded DNA template:

| | |
|---|---|
| Single stranded DNA template (1 μg/μl) | 5 μl |
| Phosphoylated mutagenic oligonculeotide (1.6 pmol/1 μl) | 2.5 μl |
| Buffer 1 | 3.5 μl |
| Water | 6 μl |

Where two mutagenic oligonucleotides were used simultaneously, 2.5 μl (1.6 pmole/1 μl) of each phosporylated oligonucleotide was added to 5 μl single stranded DNA template (1 μg/μl) in 3.5 μl Buffer 1 and 3.5 μl water. Where 3 mutagenic oligonucleotides were used 2.5 μl (1.6 pmol/μl) of each phosporylated oligonucleotide was added to 5 μl single stranded DNA (1 μg/μl in 3.5 μl Buffer 1 and 1 μl water). The above ingredients were placed in a capped tube in a 70° C. water bath for 3 minutes if the oligonucleotide was <30bases in length or in a boiling water bath for 3 minutes if the oligonucleotide was >30 bases in length. The tube was then placed in a 37° C. water bath for 30 minutes.

2. Synthesis and ligation of mutant DNA strand:
To the annealing reaction were added

| | |
|---|---|
| MgCl$_2$ solution | 5 μl |
| Nucleotide mix 1 (contains dCTP alpha S) water | 19 μl |
| Klenow fragment (6 units) | 1.5 μl |
| T4 DNA ligase (5 units) | 2 μl |

The above ingredients were placed in a 16° C. waterbath and left overnight.

3. Removal of single stranded (non-mutant) DNA using disposable centrifugal filter units.

To the reaction from Step 2 the following ingredients were added:

| | |
|---|---|
| Water | 170 μl |
| 5M NaCl | 30 μl |

The 250 μl sample was added to the top half of the filter unit and centrifuged at 1500 rpm for 10 minutes at room temperature in a SORVALL RT6000B bench top centrifuge using a SORVALL H1000B swing out rotor. Sample passes through two nitrocellulose membranes which bind the single stranded DNA leaving the double stranded DNA to pass through to the collection tube below.

1000 μl of 500 mM NaCl were added and respun for 10 minutes to wash through any remaining RF DNA.

The following ingredients were added to the filtrate:

| | |
|---|---|
| 3M Sodium Acetate (pH6.0) | 28 μl |
| Cold Ethanol (−20° C.) | 700 μl |

The mixture was placed in a dry ice and ethanol bath for 20 minutes and centrifuged in an Eppendorf microfuge for 15 minutes. The pellet was then resuspended in 10 μl buffer 2.

4. Nicking of the non-mutant strand using Nci I.

To the reaction mix from step 3, was added 65 μl Buffer 3 and 8 units Nci I (1B1). The mixture was placed in a 37° C. water bath for 90 minutes.

5. Digestion of non-mutant strand using exonuclease III

To the reaction mix from step 4 was added

| | |
|---|---|
| 500 mM NaCl | 12 μl |
| Buffer 4 | 10 μl |
| Exonuclease III (50 units) | 2 μl |

The mixture was placed in a 37° C. water bath and incubated for 30 minutes at 37° C. (50 units of exonuclease III will digest approximately 3,000 bases in 30 minutes). The mixture was then placed in a 70° C. water bath for 15 minutes to inactivate the enzymes.

6. Repolymerisation and ligation of the gapped DNA.
To the reaction mix from step 5 was added

| | |
|---|---|
| nucleotide mix 2 | 13 μl |
| MgCl$_2$ solution | 5 μl |
| DNA polymerase I (4 units) | 1 μl |
| T4 DNA ligase (2.5 units) | 1 μl |

The mixture was placed in a 16° C. bath for 3 hours.

7. Transformation of competent host E. coli TG1 cells with the DNA:

300 μl of freshly prepared competent E. coli TG1 cells (prepared following the method of Mandel and Higa) were transformed with 20 μl of the reaction mix from step 6 (in duplicate). The transformants were plated out in a lawn of log phase TG1 cells in TY Top agar on TY plates and incubated overnight at 37° C.

The E. coli strain TG1 is freely available from for example the E. coli Genetic Stock Centre, Yale University, USA and from Amersham International plc, Amersham Place, Little Chalfont, Amersham, Buckinghamshire, England HP7 9NA as supplied in their "in vitro mutagenesis system, oligonucleotide directed" kit (Product code RPN 1523)

REFERENCE EXAMPLE 7

Preparation of [Met$^{-1}$, Arg$^{11}$, Ser$^{17,27,60,65}$]human G-CSF modified with methyl polyethylene glycol 5000

A. Preparation of human [Met$^{-1}$, Arg$^{11}$Ser$^{17,27,60,65}$]G-CSF

The procedure described in Reference Example 6 was repeated using the mutagenic template M13mp18 containing the gene for [Met$^{-1}$, Ser$^{17,27}$]G-CSF described in Reference Example 3 or 5. The mutagenic oligonucleotides used are designated SEQ ID No 28 and SEQ ID No 29 and are defined hereinafter.

The triplet ACG in SEQ ID No 28 serves to convert Gln at position 11 to Arg and the first and last AGA triplets in SEQ ID No 29 serve to convert Pro at positions 65 and 60 to Ser. The mutagenesis was carried out as described in Reference Example 6 using SEQ ID No 29 in a single priming mutagenesis. This yielded a single plaque which incorporated the Pro 60 Set and Pro 65 Ser changes. Single stranded DNA was prepared from this plaque as described in Reference Example 6. This DNA was used as a mutagenic template in a single priming mutagenesis using SEQ ID No 28 as mutagenic primer. This yielded >100 plaques, 3 of which were screened by DNA sequencing as previously described. All 3 had the full set of changes incorporated. Double-stranded RF DNA was prepared from one of the plaques by following the procedure for large scale preparation of single stranded DNA (step d in Reference Example 3) to step B5. The RF DNA was extracted from the bacterial pellet by the alkali lysis procedure of Birnboim and Doly (Nucleic Acids Research (1979) 7, 1513-1523) and purified by caesium chloride density gradient centrifugation as described in "Molecular Cloning—a Laboratory Manual" by Sambrook, Fritsch and Maniatis (Cold Spring Harbor Publication). The purified RF DNA was digested with EcoRI and SalI in buffer H as described previously and the 619bp fragment, containing the trp promoter, ribosome binding site, translation initiation codon and gene for [Met$^{-1}$, Ser$^{17,27}$]G-CSF isolated from a 0.7% agarose gel by use of Geneclean (TM). The fragment was ligated into an EcoRI-SalI digested pICI0020 vector, using a 2:1 molar excess of insert to vector, with T4 DNA ligase (BRL) and ligase buffer, essentially as described previously. The ligation mix was used to transform E. Coli strain HB101. Transformants were selected for by growth on L-agar plates containing 50 μg/ml ampicillin. Colonies were screened for the presence of the inserted DNA by restriction analysis of plasmid DNA prepared by the method of Birnboim and Doly as described in "Molecular Cloning—a Laboratory Manual" Sambrook, Fritsch and Maniatis (Cold Spring Harbor Publication). Plasmid DNA from a colony containing the expected 619bp EcoRI - SalI insert was used to transform E.coli strain MSD522 and designated pICI1239. Purification was effected as described in Reference Example 3.

B. Preparation [Met$^{-1}$, Arg$^{11}$, Ser$^{17,27,60,65}$]hu G-CSF modified with methyl polyethylene glycol 5000

A solution of [Met$^{-1}$, Arg$^{11}$, Ser$^{17,27,60,65}$]hu G-CSF (418 mg) in water (400 ml) was raised to pH 8.0 by the addition of 0.8 M sodium borate, pH 8.8 and concentrated to 50 ml (8 mg/ml) by ultrafiltration on an Amicon YM10 membrane (M.W. cut off 10kDa). To this solution was added an equal volume of 0.5M sodium borate, pH8.8, followed by methyl polyethylene glycol p-nitrophenyl carbonate, approx M.W. 5000, Sigma Chemical Co. Ltd (11.3 g, 100 equivalents, 20 equivalents per amino group on [Met$^{-1}$, Arg$^{11}$, Ser$^{17,27,60,65}$]hu G-CSF) dissolved in water (100 ml). The reaction was allowed to proceed at room temperature with gentle stirring for 3 hours and quenched by the addition of ethanolamine hydrochloride, pH 8.0 (10 equivalents per mole of activated methyl polyethylene glycol). The reaction mixture was concentrated on an Amicon YM30 membrane (M.W. cut off 30kDa) at 4° C. to a final retentate volume of 50 ml. The retentate was diluted with 0.1 M ammonium bicarbonate pH 8.0 (200 ml) and re-concentrated to 50 ml as before by ultrafiltration. This procedure was repeated four times and the product finally concentrated to about 25 ml. The concentrated solution of product was chromatographed on a column (5×90 cm) of Ultrogel AcA54 equilibrated with 10mM sodium phosphate, 150mM sodium chloride, pH7.4 containing 1 mg/ml sodium azide (PBS-azide). Fractions containing the modified protein were identified by monitoring protein at 280nm and polyethylene glycol by iodine/potassium iodide titration (C.R. Acad. Sci. Paris 274 1617, 1972), pooled and exhaustively dialysed against water. The final product was concentrated by ultrafiltration on an Amicon YM30 membrane to greater than 11.5 mg/ml, filtered through a 0.22 micron filter under sterile conditions and stored at 4° C. for further studies.

Protein estimates by amino acid analysis after acid hydrolysis indicated an overall recovery of 51% of [Met$^{-1}$, Arg$^{11}$, Ser$^{17,27,60,65}$]hu G-CSF in the final modified product. PAGE-SDS on the reaction mixture indicated no unreacted [Met$^{-1}$, Arg$^{11}$, Ser$^{17,27,60,65}$]hu G-CSF remained, all the product running as a high M.W. streak. Titration of filtrates and retentates with iodine/potassium iodide showed that repeated ultrafiltration at pH 8.0 on a YM 30 membrane effectively removed all non-protein bound methyl polyethylene glycol derivatives. This was confirmed by size exclusion chromatography on a column of Ultrogel AcA54 calibrated subsequently with blank ethanolamine quenched activated methyl polyethylene glycol. Iodine/potassium iodide titration of the [Met$^{-1}$, Arg$^{11}$, Ser$^{17,27,60,65}$]hu G-CSF covalently bound to methyl polyethylene glycol combined with protein estimates by amino acid analysis after acid hydrolysis indicated about 3.9 moles of methyl polyethylene glycol per mole of protein. The specific biological activity of the [Met$^{-1}$, Arg$^{11}$, Ser$^{17,27,60,65}$]hu G-CSF, (1.2 ×10$^9$ U/mg), fell to 2.2×10$^8$ U/mg (19%) after the modification with the methylpolyethylene glycol. The product was completely stable and showed no change in specific activity in solution at up to 10 mg/ml (by protein) in PBS at 37° C. over 14 days.

REFERENCE EXAMPLE 8

Preparation of [Met$^{-1}$, Glu$^{15}$, Ser$^{17,27}$,Ala$^{26,28}$, Lys$^{30}$]human G-CSF modified with methyl polyethylene glycol 5000

Preparation of human [Met$^{-1}$, Glu$^{15}$, Ser$^{17,27}$, Ala$^{26,28}$, Lys$^{30}$]G-CSF a) The procedure described in Reference Example 7 was repeated using the mutagenic template M13mp18 containing the gene for [Met$^{-1}$, Ser$^{17,27}$]G-CSF described in Reference Example 3 or 5. The mutagenic oligonucleotides used are designated SEQ ID No 33 and SEQ ID No 34 and are defined hereinafter.

The triplet TTC in SEQ ID No 33 serves to convert Leu at position 15 to Glu. In SEQ ID No 34 the first TTT triplet serves to convert Ala at position 30 to Lys and the triplets AGC serve to convert Gly at position 28 and 26 to Ala.

The mutagenesis procedure was essentially as described in Reference Example 6 as a double priming experiment and the expression cassette transferred to the expression plasmid to give pICI 1266.

b) Purification

Frozen cell paste was lysed and the crude pellet fraction separated as in Reference Example 3. The inclusion bodies in the pellet containing this protein were solubilised by the deoxycholic acid (sodium salt) buffer described in Reference Example 3. The following modified procedure was used for this protein.

Crude pellet fraction (60–100 g) was thawed and resuspended in 25 mM EDTA, 50mM Tris.HCl, pH 8.0 (1200 ml) using a Polytron homogeniser with a PTA 20 probe at speed setting 5. The suspension was mixed at room temperature for 30 minutes and centrifuged at 6,500×g for 30 minutes in a Sorvall RCSC centrifuge using a GSA rotor. The supernatant was discarded and the pellet retreated twice in the same manner. The pellet was next twice resuspended in water (1 liter) and centrifuged as in Reference Example 3. Thereafter the purification procedure was as in Reference Example 3.

B. Preparation of [Met$^{-1}$, Glu$^{15}$,Ser$^{17,27}$, Ala$^{26,28}$,Lys$^{30}$]hu G-CSF modified with methyl polyethylene glycol 5000

This was prepared as described in Reference Example 7, again using 100 molar equivalents of reagent even though this derivative contains an additional lysine residue at position 30. The final product contained about 4.7 moles of methyl polyethylene glycol covalently bound per mole of protein. This increased level of incorporation is consistent with the presence of an extra potential site for modification, and is reflected in a slight increase in MW on PAGE-SDS. The specific biological activity of unmodified derivative, $1.2 \times 10^9$ U/mg fell to $4.4 \times 10^7$ U/mg (3%) in the modified product The product was completely stable and showed no change in specific activity in solution at up to 10 mg/ml (by protein) in PBS at 37° C. over 14 days.

REFERENCE EXAMPLE 9

The procedure of Reference Examples 1, 3 and 5 was repeated using *E.Coli* TG1 instead of E. coli strain MSD 522 in the fermentation step (see for example Reference Example 3 (e)).

REFERENCE EXAMPLE 10

Alternative Extraction Process for Human [Met$^{-1}$, Arg$^{11}$, Ser$^{17,27,60,65}$] G-CSF The process of Reference Example 7 was repeated except that the extraction process was effected as follows:

Frozen cell paste (640 g) was resuspended at 4° C. in 50mM Tris HCl, 5mM EDTA, 5mM dithiothreitol, 2 M urea, pH 8.0 containing 1 mg/ml sodium azide (5 liters) using a Polytron homogeniser with a PTA20 probe at speed setting 7/8. The suspension was lysed by passing three times through a Manton-Gaulin Lab 60/60 homogeniser at 6000 psi and flushed through with a further 1 liter of buffer. Cooling was provided by a single pass Conair chiller at −20° C. The lysate was centrifuged at 5000×g for 30 minutes in a Sorvall RC3C centrifuge using an H6000A rotor.

The supernatant was discarded and the pellet (about 450 g) was resuspended in the same buffer (10 liters). The suspension was mixed for 30 minutes at room temperature and centrifuged at 5000 rpm for 30 minutes in two Sorvall RC3C centrifuges using H6000A rotors. the supernatant was discarded and the pellet retreated twice in the same manner. The pellet was next twice resuspended in water (10 liters) and centrifuged at 5000rpm for 30 minutes. The final pellets containing washed inclusion bodies were resuspended in 2% w/v N-lauroyl safcosine sodium salt in 50mM Tris HCl, pH 8.0 (1 liter) containing 1 mg/ml sodium azide using a Polytron homogeniser at speed setting 7. 20mM cuptic sulphate in water (1.5 ml) was added and the mixture stirred overnight at room temperature before centrifugation at 10,000 rpm for 30 minutes in a Sorvall RC5C centrifuge using a GSA rotor.

The supernatant containing the derivative was filtered through a 5 μm filter to remove any particulate matter, diluted six-fold with 50mM Tris HCl, pH 8.0 containing 1 mg/ml sodium azide at 4° C., and ultrafiltered at maximum pressure in an Amicon DC20 ultrafiltration device fitted with a S10Y10 cartridge (10 kDa cut-off) against 10mM sodium phosphate, 150mM sodium chloride pH 7.4 (90 liters) containing 1 mg/ml sodium azide. A precipitate formed towards the end of the ultrafiltration.

The retentate (2.1 mg/ml total protein, 1.7 mg/ml product) was collected in 4 liter, screw top, polypropylene containers and incubated overnight at 37° C. The precipitate which formed was removed by centrifugation at 5000rpm for 45 minutes in a Sorvall RC3C, and the supernatant stored at 4° C.

Monitoring by SDS-PAGE and rpHPLC, showed that during the final heat treatment contaminating E.-coli proteins, product oligomers, and degradation products were selectively precipitated, with some 85% of the desired product remaining in solution. The highly enriched clarified, heat treated product solution was fully biologically active and stable at 20 mg/ml at 37° C. over two weeks with no evidence of proteolytic degradation and less than 20% precipitation. This provided an excellent intermediate for further chromatographic purification.

REFERENCE EXAMPLE 11

Preparation of [Met$^{-1}$, Arg$^{11}$, Ser$^{17,27,60,65}$]human G-CSF using production vector including trp promoter a) Plasmid pICI1239 (described in Reference Example 7) was digested with EcoRI and SalI in buffer H as described previously. The small EcoRI-SalI fragment containing the trp promoter, ribosome binding site and gene for [Met$^{-1}$,Arg$^{11}$,Ser$^{17,27,60,65}$]hu G-CSF was isolated from a 0.7% agarose gel by use of Geneclean(TM). A vector fragment was prepared from pICI 0080 (see Reference Example 6) by digestion with EcoRI and XhoI in buffer H and the large EcoRI-XhoI fragment isolated from a 0.7% agarose gel by use of Geneclean(TM). The small EcoRI-SalI fragment was ligated into the EcoRI-XhoI vector fragment, using a 2:1 molar excess of insert to vector as described previously and the ligation mix used to transform E. coli strain MSD 522. Transformants were selected for growth on L-agar plates containing tetracycline (15 μg/ml). Three colonies were selected and grown up in M9 minimal media (75 ml) containing supplements and tetracycline (15 μg/ml) at 37° C. for 20 hours on a reciprocating shaker. Protein accumulation was measured by scanning Coomassie blue stained SDS-PAGE gels of whole cell lysate. All three clones expressed [Met$^{-1}$,Arg$^{11}$,Ser$^{17,27,60,65}$]hu G-CSF. Plasmid DNA from one of the colonies was designated pICI1327 and the sequence of the promoter and gene confirmed by standard dideoxy sequencing procedures as described previously.

b) Fermentation pICI 1327 was transformed into *E. coli* strain MSD 522 and the resultant recombinants purified and maintained on glycerol stocks at −80° C.

An aliquot of the culture was removed from stock and streaked onto agar plates of tetracycline to separate single colonies after overnight growth at 37° C. A single desired colony was removed and resuspended in 10 ml tetracycline broth and 100 μl immediately inoculated into each of 3 250 ml Erlenmeyer flasks containing 75 ml tetracycline broth. After growth for 16h at 37° C. on a reciprocating shaker the contents of the flasks were pooled and used to inoculate a fermenter containing 20L growth medium.

| Composition of Growth Medium | |
|---|---|
| | Made up of distilled water g/l |
| KH$_2$PO$_4$ | 3.0 |
| Na$_2$HPO$_4$ | 6.0 |
| NaCl | 0.5 |
| Casein hydrolysate (Oxoid L41) | 2.0 |
| (NH$_4$)$_2$SO$_4$ | 10.00 |
| Yeast Extract (Difco) | 10.00 |
| Glycerol | 35.00 |
| L-Leucine | 0.625 |
| MgSO$_4$. 7H$_2$O | 0.5 |
| CaCl$_2$. 2H$_2$O | 0.03 |
| Thiamine | 0.008 |
| FeSO$_4$/Citric Acid | 0.04/0.02 |
| Trace element solution (TES) | 0.5 ml l$^{-1}$ |
| Tetracycline | 10 mg l$^{-1}$ |

Fermentations were then carried out at a temperature of 37° C., and at a pH, controlled by automatic addition of 6 M sodium hydroxide solution, of pH 6.7. The dissolved oxygen tension (dOT) set point was 50% air-saturation and was initially controlled by automatic adjustment of the fermenter stirrer speed. Air flow to the fermenter, initially 20 L/min, corresponding to 1 volume per volume per minute (VVM) was increased to 50 L/min (2.5 VVM) when the fermenter stirrer speed approached 80-90% of its maximum. Since the oxygen transfer rate (OTR) of the fermenters was unable to meet the oxygen uptake rate (OUR) of the bacteria at a cell density greater than that corresponding to an OD$_{550}$ of 50 under the conditions described, dOT in the fermenter at cell densities greater than this was maintained at 50% air-saturation by restricting bacteria oxygen uptake rate. This was achieved by formulating the medium to become carbon-limited at OD$_{550}$ of 50 and then supplying a feed of the limiting carbon source, together with ammonium sulphate and yeast extract, at a rate which restricted bacterial growth rate.

Fermentations were performed for 18h and during that time samples were taken for measurement of optical density (OD$_{550}$), cell dry weight and accumulation of [Met$^{-1}$,Arg$^{11}$,Ser$^{17,27,60,65}$]human G-CSF within the cells. [Met$^{-1}$,Arg$^{11}$,Ser$^{17,27,60,65}$]human G-CSF accumulation was measured by scanning Coomassie blue stained SDS-PAGE gels of whole cell lysates of the sampled bacteria as is well known in the art.

When OD$_{550}$ reached 35 (8.5h), casein hydrolysate solution (100 g/10×zoid L41) was pumped into the fermenters at a rate of 0.75 g/1/h.

When OD$_{550}$ reached approximately 50, the supply of carbon-source in the fermentation batch became exhausted leading to a rapid rise in dOT from 50% air saturation. At this point, a feed containing glycerol (470 g/l), yeast extract (118 g/l) and ammonium sulphate (118 g/l) was pumped into the fermenters at a rate which returned and then maintained the dOT at 50% air saturation with the fermenter stirrer at ca 70-80% of its maximum. Casein hydrolysate feeding was maintained at 0.75 g/l/h throughout. After approximately 18 hours, when microscopic examination of the culture showed the presence of large inclusion bodies within a majority of the cells, bacteria were harvested on a Sorval RC3B centrifuge (7000 g, 30 min., 4° C.) and stored frozen at minus 80° C.

c) Purification

Purification was effected as described in Reference Example 3(f)

REFERENCE EXAMPLE 12

Preparation of [Met$^{-1}$,Arg$^{11}$,Ser$^{17,27,60,65}$]human G-CSF using production vector including T7A3 promoter a) An EcoRI-SalI fragment, containing a T7A3 promoter, a trp leader ribosome binding site sequence and a gene for [Met$^{-1}$,Ser$^{17,27}$]hu G-CSF was sub-cloned into M13 mp18 as described in part d) of Reference Example 3. The sequence of the EcoRI-SalI fragment is set out in SEQ ID No 47 and FIG. 3, SEQ ID No 47 consists of the EcoRI restriction site (nucleotides 1-6), the A3 promoter sequence of bacteriophage T7 (nucleotide 7-52), the trp leader ribosome binding site sequence (nucleotides 53-78)and translation initiation codon (nucleotides 79-81). FIG. 3 sets out the nucleotide sequence of [Met$^{-1}$,Ser$^{17,27}$]human G-CSF terminating in the SalI restriction site. It will be appreciated that the 3' terminal ATG codon of SEQ ID No 47 immediately precedes the ACT codon which codes for threonine (amino acid 1) in FIG. 3. The 5' nucleotide sequence AATTCAGT is thus absent from the EcoRI-SalI fragment. The EcoRI-SalI fragment may also be prepared by excision from pICI 1295 (see Reference Example 31). Site-directed mutagenesis was performed on single-stranded DNA as described in Reference Example 6 using oligonucleotide SEQ ID No 28 to convert the codon for Gln at position 11 to Arg. Double-stranded RF DNA was prepared from a plaque containing the Gln$^{11}$→Arg$^{11}$ change as described in Reference Example 7, except that at step B3 incubation was for 3 hours instead of 5 hours, and digested with EcoRI (as described previously) and SnaBI (as described in Reference Example 13). The resulting 144 bp EcoRI-SnaBI fragment containing the T7A3 promoter, trp leader ribosome binding site sequence and gene fragment with Arg$^{11}$ codon was isolated and ligated to an EcoRI-SnaBI cut vector from pICI 1327 (which contains codons for Ser$^{60}$ and Ser$^{65}$ and is described in Reference Example 11). The ligation mix was used to transform *E.coli strain* MSD522 and transformants selected for growth on L-agar plates containing tetracycline (15 μg/mg). Plasmid DNA from a colony containing the expected T7A3 promoter and [Met$^{-1}$, Arg$^{11}$,Se$^{17,27,60,65}$] hu G-CSF gene sequence were identified by sequencing DNA from the isolated plasmid and designated pICI 1386.

The fermentation was effected according to two alternative processes (b) and (c) below. Process (b) was effected at 37° C. and after 16 hours fermentation as described, microbial biomass was 35 g/l and [Met$^{-1}$, Arg$^{11}$,Ser$^{17,27,60,65}$]human G-CSF was estimated to be accumulated to 7 g/l fermentation broth. Process (c) was effected at 30° C. and the fermentation was accordingly slower because of the lower fermentation temperature. With regard to process(c), after 35 hours, the microbial biomass was 55 g/l and the [Met$^{-1}$,Arg$^{11}$,Ser$^{17,27,60,65}$]human G-CSF yield was estimated to be accumulated to 15 g/l fermentation broth.

b) *E. Coli* strain CGSC 6300 (genotype F$^-$,$\lambda^-$, lac+) obtained from the *E.coli* Genetic Stock Centre was transformed with plasmid pICI 1386. The resultant strain CGSC 6300 (pICI 1386) was purified and maintained in glycerol stocks at −80° C. An aliquot of the culture was removed from stock and streaked onto agar plates of L-tetracycline to separate single colonies after overnight growth (16h) at 37° C. A single colony of CGSC 6300 (pICI 1386) was removed and resuspended in 10ml L-tetracycline broth and 100 μl immediately inoculated into each of twenty 250ml Erlenmeyer flasks containing 75ml of L-tetracycline broth. After growth for 16h at 37° C. on a reciprocating shaker the contents of the flasks were pooled, and used to inoculate a fermenter containing 20 liters of modified LCM50 growth medium. The composition of the growth medium is in Table 1.

TABLE 1

Composition of growth medium
Modified LCM50 Growth Medium (A)

| | made up with distilled water g/l |
|---|---|
| KH$_2$PO$_4$ | 3.0 |
| Na$_2$HPO$_4$ | 6.0 |
| NaCl | 0.5 |
| Casein Hydrolysate (Oxoid L41) | 2.0 |
| (NH$_4$)$_2$SO$_4$ | 10.0 |
| Yeast extract (Difco) | 20.0 |
| Glycerol | 35.0 |
| MgSO$_4$.7H$_2$O | 0.5 |
| CaCl$_2$.2H$_2$O | 0.03 |
| Thiamine | 0.008 |
| FeSO$_4$/Citric acid | 0.04/0.02 |
| Trace element solution (TES) | (0.5 ml l$^{-1}$) |
| Tetracycline | (10 mg l$^{-1}$) |

The fermentation was then carried out at a temperature of 37° C. and at a pH, controlled by automatic addition of 6 M sodium hydroxide solution, of pH 6.7. The dissolved oxygen tension (dOT) set point was 50% air saturation and was initially controlled by automatic adjustment of the fermenter stirrer speed. Air flow to the fermenter was initially 20 L/min corresponding to 1.0 volume volume per minute (VVM) and was increased to 45 L/min manually when the fermenter stirrer speed reached its maximum (1000 rpm). The fermentation was performed for 16 h and during that time samples were taken for measurement of optical density of the culture (OD$_{550}$ biomass concentration, total microbial protein concentration and accumulation of [Met$^{-1}$, Arg$^{11}$, Ser$^{17,27,60,65}$]human G-CSF within the bacterial cells. Accummulation was measured by scanning Coomassie blue stained SDS-PAGE gels of whole cell lysates of the sampled bacteria as is well known in the art. Total microbial protein was estimated by the method of Lowry. A solution of yeast extract (225 g/L) was pumped into the fermenter 4.5h post inoculation at 1.7 g/L/h.

When the supply of carbon source (glycerol) in the growth medium became exhausted dOT increased rapidly from 50% air saturation. At this point a feed containing glycerol (714 g/l) and ammonium sulphate (143 g/L) was pumped. Since the bacterial oxygen sulphate rate (OUR) approached the maximum oxygen transfer rate of the fermenter (OTR) just prior to the carbon source in the batch growth medium becoming exhausted, the feed was pumped into the fermenter at a rate which restricted the bacterial OUR to approximately 80–90% of the fermenters maximum OTR. The feed rate was adjusted manually to return and then maintain dOT at 50% air saturation under the conditions described.

c) The fermentation process described in (b) was repeated but at a temperature of 30° C. for 35 hours. Except for the fermentation temperature of 30° C. the medium and fermentation conditions were identical to those described in (b).

d) Purification was effected as described in Reference Example 3(f).

REFERENCE EXAMPLE 13

A) Preparation of [Met$^{-1}$,Ser$^{17}$]hu G-CSF

The procedure described in Reference Example 5 for the preparation of [Met$^1$,Ser$^{17,27}$]hu G-CSF was repeated except as follows:

1) The duplex for phosphorylation was prepared from oligonucleotide sequences SEQ ID Nos 24, 25, 3 and 4, the sequences SEQ ID Nos 3 and 4 respectively replacing sequences SEQ ID Nos 26 and 27 employed in Reference Examples 3, 4 and 5.

2) The duplex referred to in (1) was phosphorylated with T4 polynucleotide kinase, but was digested with SnaBI (10 units) in 1 ×M buffer (BC; 30 μl) for 2 hours at 37° C.

3) Following purification with ethanol, the 72bp EcoRI-SnaBI fragment was purified as opposed to the 143 bp EcoRI-MstII fragment.

4) The synthetic EcoRI-SnaBI fragment was cloned into the plasmid vector pAG88 as described in REFERENCE EXAMPLE 1 and for vector preparation pAG88 was digested with SnaBI (20 units; BCL) in 1 ×M buffer (BCL: 100 μl) for 2 hours at 37° C. instead of Mst II in 1 ×H buffer.

5) Following precipitation with ethanol, the large EcoRI-SnaBI fragment was purified on a 1% agarose gel as opposed to the large EcoRI-MstII fragment.

6) The plasmid containing the gene for [Met$^{-1}$,Ser$^{17}$]hu G-CSF was designated pICI 1105.

B. Preparation of [Met$^{-1}$,Ser$^{17}$]hu G-CSF modified with methyl polyethylene glycol 5000.

A solution of [Met$^{-1}$, Ser$^{17}$]hu G-CSF (300mg, 6.25mg/ml) in water was diluted to 75ml with 1.1 M sodium borate pH8.9 to give a solution of protein (4mg/ml) in 0.4 M borate, pH8.7. To this solution was added dropwise with stirring a water solution (75ml) of methyl polyethylene glycol p-nitrophenyl carbonate approx MW5000 (Sigma Chemical Co Ltd) (100 equivalents per mole of protein; 20 equivalents per amino group). The reaction was stirred at room temperature for 3 hours and quenched by the dropwise addition of ethanolamine hydrochloride pH8 (10 equivalents per mole of activated methyl polyethylene glycol). The reaction mixture was diluted to 350 ml with 0.1 M ammonium bicarbonate pH8 and successively concentrated and diluted with this solvent in an Amicon stirred cell fitted with YM30 membrane (MW cut off 30kDa) until no yellow colour remained. The final concentrate (25 ml) was chromatographed on a column (5 x 90 cm) of Ultrogel AcA54 equilibrated and eluted with PBS-azide. Fractions containing the modified protein were identified by monitoring the protein at 280 nm, and methyl polyethylene glycol by iodine/potassium iodide titration, pooled and dialysed exhaustively against water. This product was concentrated on an Amicon YM30 membrane (MW cut off 30kDa) to 5mg/ml, filtered under sterile conditions through a 0.22 μfilter and stored at 4° C. for further studies.

SDS-PAGE on the final modified product indicated no unreacted [Met$^{-1}$,Ser$^{17}$]hu G-CSF remained all the product running as a high molecular weight streak. Titration of retentates and filtrates with iodine/potassium iodide showed that repeated ultrafiltration at pH8.0 on a YM30 membrane effectively removed all non-protein bound methyl polyethylene glycol. The final product contained about 3.5 moles of methyl polyethylene glycol covalently bound per mole protein. The specific activity of the unmodified derivative, $0.8 \times 10^9$ U/mg fell to $0.8 \times 10^8$ U/mg (10%) with modified product. The product was completely stable and showed no change in specific activity in solution at up to 10mg/ml (by protein) at 37° C. over 14 days,

REFERENCE EXAMPLE 14

Preparation of [Met$^{-1}$, Arg$^{11,23}$, Ser$^{17,27,60,65}$]human G-CSF modified with methyl polyethylene glycol 5000

A. Preparation of [Met$^{-1}$,Arg$^{11,23}$,Ser$^{17,27,60,65}$]hu G-CSF

A mutagenic template, M13mp18 containing the gene for [Met$^{-1}$,Arg$^{11,17,27,60,65}$]hu G-CSF, was prepared as described in part (d) of Reference Example 3 with plasmid pICI 1239 replacing pICI 1080. The procedure described in Reference Example 7 was repeated using the above template with mutagenic oligonucleotide designated SEQ ID No 38. This serves to convert the codon for Lys at position 23 of Arg. Double-stranded RF DNA was prepared from one phage containing the desired change and the expression cassette isolated and cloned as described in Reference Example 15 (see hereinafter) to give pICI 1388.

Further processing to yield the title compound was effected as described in Reference Examples 3 and 4.

B. Preparation of [Met$^{-1}$, Arg$^{11,23}$, Ser$^{17,27,60,65}$]hu G-CSF modified with methyl polyethylene glycol 5000.

A solution of [Met$^{-1}$Arg$^{11,23}$, Ser$^{17,27,60,65}$]hu G-CSF (300mg) in 0.1 M sodium borate, pH8.0 was concentrated to 37.5 ml by ultrafiltration on an Amicon YM10 membrane (MW cut off 10kDa). To this solution was added an equal volume of 0.8 M sodium borate pH8.8 followed by methyl polyethylene glycol p-nitrophenyl carbonate (approx MW 5000) (Sigma Chemical Company Ltd) (100 equivalents per mole [Met$^{-1}$, Arg$^{11,23}$, Ser$^{17,27,60,65}$]hu G-CSF) dissolved in water (75 ml). The reaction was allowed to proceed at 20° C. with gentle stirring for 3 hours and quenched by the addition of 1 M ethanolamine hydrochloride pH 8.0 (15 ml, 10 equivalent per mole of activated methyl polyethylene glycol). The reaction mixture was diluted to 500 ml with 0.1 M ammonium bicarbonate pH8.0 and diafiltered against 10 liters of the same buffer using an Amicon CH2A-IS spiral cartridge system fitted with an SLY30 membrane (MW cut off 30kDa) until yellow p-nitrophenol was no longer visible in the retentate. The retentate was concentrated to 300 ml and placed in an Amicon 8400 stirred cell fitted with a YM30 (30kDa cut off) membrane. The retentate was concentrated to 50 ml and re-diluted to 300 ml with 0.1 M ammonium bicarbonate, pH8.0. This procedure was repeated four times and the product finally concentrated to about 25 ml. The concentrated solution of product was chromatographed on a column (5×90 cm) of Ultrogel AcA54 equilibrated with 10mM sodium phosphate, 150mM sodium chloride pH7.1 containing 1 mg/ml sodium azide (PBS-azide). Fractions containing the modified protein were identified by monitoring protein at 280 nm and methyl polyethylene glycol by iodine/potassium iodide titration (CR Acad Sci Paris 274, 1617, 1972), pooled and exhaustively dialysed against water. The final product was concentrated by ultrafiltration on an Amicon YM30 membrane to greater than 11.5 mg/ml filtered through a 0.22 μm filter under sterile conditions and stored at 4° C. for further studies.

SDS-PAGE on the final modified product indicated no unreacted [Met$^{-1}$,Arg$^{11,23}$, Ser$^{17,27,60,65}$]hu G-CSF remained, all the product running as a high MW streak. Titration of filtrates and retentates with iodine/potassium iodide showed that repeated diafiltration at pH8.0 on a YM30 membrane effectively removed all non-protein bound methyl polyethylene glycol. The final product contained about 3.5 moles of methyl polyethylene glycol covalently bound per mole protein. The specific activity of unmodified derivative, $2.5 \times 10^9$ U/mg fell to $3.5 \times 10^8$ U/mg (14%) in the modified product. The product was completely stable and showed no change in specific activity in solution at up to 10mg/ml (by protein) at 37° C. over 14 days.

REFERENCE EXAMPLE 15

Preparation of [Met$^{-1}$, Glu$^{15}$, Ala$^{26,28}$, Ser$^{17,27}$, Arg$^{30}$]human G-CSF modified with methyl polyethylene glycol 5000

Preparation of [Met$^{-1}$,Glu$^{15}$, Ser$^{17,27}$,Ala$^{26,28}$,Arg$^{30}$]hu G-CSF A mutagenic template, M13mp18 containing the gene for [Met$^{-1}$, Glu$^{15}$, Ser$^{17,27}$,Ala$^{26,28}$,Lys$^{30}$]hu G-CSF, was prepared as described in part (d) of Reference Example 3 with plasmid pICI1266 replacing pICI1080. The procedure described in Reference Example 7 was repeated using the above template with mutagenic oligonucleotide designated SEQ ID No 37. This serves to convert the codon for Lys at position 30 to Arg. Double stranded RF DNA was prepared from one phage containing the desired change. An EcoRI-SalI expression cassette was isolated and cloned into pICIO080 as described in Reference Example 11 to give pICI1343.

Further processing to yield the title compound was effected as described in Reference Example 7 and purification was effected as described in Reference Example 8.

B) Preparation of [Met$^{-1}$,Glu$^{15}$,Ala$^{26,28}$,Ser$^{17,27}$,Arg$^{30}$]hu G-CSF modified with methylpolyethylene glycol 5000.

This was prepared as in Reference Example 14. The final product contained about 4 moles of methyl polyethylene glycol covalently bound per mole protein. The specific activity of unmodified derivative, $0.9 \times 10^9$ U/mg, fell to $0.6 \times 10^8$ U/mg (7%) in the modified product. The product was completely stable and showed no change in specific activity in solution at up to 10mg/ml (by protein) at 37° over 14 days.

REFERENCE EXAMPLE 16

Preparation of [Met$^{-1}$, Ser$^{17,27,115,116,111}$, Glu$^{111}$]human G-CSF modified with methyl polyethylene glycol 5000

A) Preparation of [Met$^{-1}$, Ser$^{17,27,115,116}$,Glu$^{111}$]human G-CSF

The procedure described in Reference Example 7 was repeated using the mutagenic template M13mp18 containing the gene for [Met$^{-1}$,Ser$^{17,27}$]G-CSF described in Reference Example 3 or 5. The mutagenic oligonucleotide used is designated SEQ ID No 30 (as hereinafter defined).

The triplet GCT serves to convert Thr at position 116 to Ser, the triplet AGA serves to convert Thr at position 115 to Ser and the triplet TTC serves to convert Ala at position 111 to Glu. The mutagenesis procedure was essentially as described for Reference Example 7 and the expression cassette was transferred to the expression plasmid to give pICI 1243. Fermentation and purification was effected as described in Reference Example 3 and 4.

B) Preparation of [Met$^{-1}$, Ser$^{17,27,115,116}$,Glu$^{111}$]hu G-CSF modified with methyl polyethylene glycol 5000.

This was prepared as in Reference Example 14. The final product contained about 4 moles of methyl polyethylene glycol covalently bound per mole protein. The specific activity of un modified derivative $0.7 \times 10^9$ U/mg fell to $0.8 \times 10^8$ U/mg (11%) in the modified product. The product was completely stable and showed no change in specific activity in solution at up to 10mg/ml (by protein) at 37° over 14 days.

REFERENCE EXAMPLE 17

Preparation of [Met$^{-1}$,Arg$^{11,165}$, Ser$^{17,27}$,Lys$^{58}$]hu G-CSF modified with methyl polyethylene glycol 5000

A) Preparation of [Met$^{-1}$,Arg$^{11}$, Ser$^{17,27}$, Lys$^{58}$, Arg$^{165}$]human G-CSF The procedure described in Reference Example 7 was repeated using the mutagenic template M13mp18 containing the gene for [Met$^{-1}$,Ser$^{17,27}$]G-CSF described in Reference Example 3 and 5. The mutagenic oligonucleotides used are designated SEQ ID No 28, SEQ ID No 31 and SEQ ID no 32 (as hereinafter defined).

The triplet TTT in SEQ ID No 31 serves to convert Trp at position 58 to Lys and in SEQ ID No 32 the second GCG triplet serves to convert Tyr at position 165 to Arg.

The mutagenesis procedure was initially carried out as a double priming experiment using SEQ ID No 31 and SEQ ID No 32 as mutagenic oligonucleotides as described for Reference Example 6. This yielded 2 plaques both of which had the SEQ ID No 32 change (Tyr 165 Arg) but no the SEQ ID No 31 change. Single stranded DNA was prepared from one of these plaques as described in Reference Example 3. This DNA was used as a mutagenic template in a double priming mutagenesis using SEQ ID No 28 and SEQ ID No 31 as mutagenic primers. This yielded 2 plaques one of which had the complete set of changes incorporated and the expression cassette was transferred to the expression plasmid to give pICI 1246. Fermentation and purification was effected as described in Reference Example 3 and 4.

B) Preparation of [Met$^{-1}$, Arg$^{11,165}$, Ser$^{17,27}$, Lys$^{58}$]hu G-CSF modified with methyl polyethylene glycol 5000

This was prepared as in Reference Example 14. The final product contained about 4.5 moles of methyl polyethylene glycol covalently bound per mole protein. The specific activity of un modified derivative, $0.8 \times 10^9$ U/mg fell to $0.1 \times 10^9$ U/mg (13%) in the modified product. The product was completely stable and showed no change in specific activity in solution at up to 10mg/ml (by protein) at 37° over 14 days.

REFERENCE EXAMPLE 18

Preparation of [Met$^{-1}$, Ser$^{17,27}$, Ala$^{44,51,55}$, Lys$^{49,58}$]human G-CSF modified with methyl polyethylene glycol 5000

A) Preparation of [Met$^{-1}$,Ser$^{17,27}$, Ala$^{44,51,55}$, Lys$^{49,58}$]human G-CSF.

The procedure describe in Reference Example 7 was repeated using the mutagenic template M13mp18 containing the gene for [Met$^{-1}$, Ser$^{17,27}$]G-CSF described in Reference Example 3 or 5. The mutagenic oligonucleotides used are designated SEQ ID No 35 and SEQ ID No 36 (as hereinafter defined). In SEQ ID No 35 the triplets AGC serve to convert Gly to Ala at position 51 and Pro to Ala at position 44 and the triplet TTT serves to convert Leu to Lys at position 49. In SEQ ID No 36 the triplet TTT serves to convert Trp to Lys at position 58 and the second AGC triplet serves to convert Gly to Aln at position 55.

The mutagenesis was carried out as a double priming experiment as described in Reference Example 6. This yielded 16 plaques. 8 Plaques were screened by DNA sequencing as described in Reference Example 7. All plaques had the SEQ ID No 36 changes (Gly55Ala, Trp58Lys) but none had the SEQ ID No 35 changes. Single stranded DNA was prepared from one of these plaques as described in Reference Example 3(d) and used as a mutagenic template in a single priming mutagenesis using SEQ ID No 35 as mutagenic primer. This yielded 50 plaques, 3 of which were screened by DNA sequencing, 2 had the complete set of changes. The expression cassette was transferred to the expression plasmid to give pICI 1297. Fermentation and purification was effected as described in Reference Examples 3 and 4.

B) Preparation of [Met$^{-1}$, Ser$^{17,27}$, Ala$^{44,51,55}$, Lys$^{49,58}$]hu G-CSF modified with methyl polyethylene glycol 5000.

This was prepared as in Reference Example 14. The final product contained about 3.5 moles of methyl polyethylene glycol covalently bound per mole protein. The specific activity of unmodified derivative, $0.75 \times 10^9$ U/mg fell to $0.32 \times 10^9$ U/mg (47%) in the modified product. The product was completely stable and showed no change in specific activity in solution at up to 10mg/ml (by protein) at 37° over 14 days.

REFERENCE EXAMPLE 19

Preparation of [Met$^{-1}$, Arg$^{11,16}$, Ser$^{17,27,60,65}$]human G-CSF modified with methyl polyethylene glycol 5000

A) Preparation of [Met$^{-1}$, Arg$^{11,16}$, Ser$^{17,27,60,65}$]hu G-CSF

The procedure described in Reference Example 14 was repeated with oligonucleotide designated SEQ ID No 38 replaced by SEQ ID No 42 (this serves to convert the codon for Lys at position 16 to Arg) to give pICI 1387.

Further processing to yield [Met$^{-1}$, Arg$^{11,16}$, Ser$^{17,27,60,65}$]hu G-CSF and the purification of this compound were effected as described in Reference Examples 3 and 4.

B) Preparation of [Met$^{-1}$,Arg$^{11,16}$, Ser$^{17,27,60,65}$]hu G-CSF modified with methyl polyethylene glycol 5000.

This protein precipitated when dialysed exhaustively against water in the final step of the purification procedure described in Reference Example 4. The precipitate was redissolved in 0.1 M sodium borate pH8.0 and modified with methyl polyethylene glycol 5000 as in Reference Example 14. The final product contained about 3.5 moles of methyl polyethylene glycol covalently bound per mole protein. The specific activity of unmodified derivative $2.3 \times 10^9$ U/mg, fell to $3.6 \times 10^8$ U/mg (16%) in the modified product. The product was completely stable and showed no change in specific activity in solution at up to 10mg/ml (by protein) at 37° C. over 14 days.

REFERENCE EXAMPLE 20

Preparation of [Me$^{-1}$, Arg$^{11,34}$, Ser$^{17,27,60,65}$]human G-CSF modified with methyl polyethylene glycol 5000

A) Preparation of [Met$^{-1}$, Arg$^{11,34}$, Ser$^{17,27,60,65}$]hu G-CSF

The procedure described in Reference Example 14 was repeated with oligonucleotide designated SEQ ID No 38 replaced by SEQ ID No 39 (this serves to convert the codon for Lys at position 34 to Arg) to give pICI1389.

Further processing to yield the title compound and the purification of the title compound were effected as described in Reference Examples 3 and 4.

B) Preparation of [Met$^{-1}$, Arg$^{11,34}$, Ser$^{17,27,60,65}$]hu G-CSF modified with methyl polyethylene glycol 5000.

This was prepared as in Reference Example 14. The final product contained about 4 moles of methyl polyethylene glycol covalently bound per mole of protein. The specific activity of unmodified derivative $1.4 \times 10^9$ U/mg fell to $2.0 \times 10^8$ U/mg (14%) in the modified product. The product was completely stable and showed no change in specific activity in solution at up to 10mg/ml (by protein) at 37° over 14 days.

REFERENCE EXAMPLE 21

Preparation of [Met$^{-1}$, Arg$^{11,40}$, Ser$^{17,27,60,65}$]human G-CSF modified with methyl polyethylene glycol 5000

A) Preparation of [Met$^{-1}$, Arg$^{11,40}$, Ser$^{17,27,60,65}$]hu G-CSF

The procedure described in Reference Example 14 was repeated with oligonucleotide SEQ ID No 38 replaced by SEQ ID No 40 (this serves to convert the codon for Lys at position 40 to Arg) to give pICI 1390.

Further processing to yield the title compound and the purification of the title compound were effected as described in Reference Examples 3 and 4.

B) Preparation of [Met$^{-1}$, Arg$^{11,40}$, Ser$^{17,27,60,65}$]hu G-CSF modified with methyl polyethylene glycol 5000.

This was prepared as in Reference Example 14. The final product contained about 4 moles of methyl polyethylene glycol covalently bound per mole protein. The specific activity of unmodified derivative $1.3 \times 10^9$ U/mg, fell to $3.0 \times 10^8$ U/mg (23%) in the modified product. The product was completely stable and showed no change in specific activity in solution at up to 10mg/ml (by protein) at 37° over 14 days.

REFERENCE EXAMPLE 22

Preparation of [Met$^{-1}$, Ala$^1$, Thr$^3$, Tyr$^4$, Arg$^{5,11}$, Ser $^{17,27,60,65}$]human G-CSF modified with methyl polyethylene glycol 5000.

A) Preparation of [Met$^{-1}$, Ala$^1$, Thr$^3$, Tyr$^4$, Ar$^{5,11}$, Ser$^{17,27,60,65}$]hu G-CSF The procedure described in Reference Example 14 was repeated with oligonucleotide SEQ ID No 38 replaced by SEQ ID No 41 (this serves to convert codons for Thr, Leu, Gly and Pro at positions, 1,3,4 and 5 to Ala, Thr, Tyr and Arg respectively to give pICI 1391. The polypeptide of this Example illustrates that the modification of the present invention may be applied to a polypeptide known to possess G-CSF activity in order to improve the solution stability of the polypeptide The known polypeptide is [Met$^{-1}$, Ala$^1$, Thr$^3$, Tyr$^4$, Arg$^5$, Ser$^{17}$]hu G-CSF which is described in European Patent Publication No 272,703 of Kyowa Hakko Kogyo Co Ltd.

Further processing to yield the title compound and the purification of the title compound were effected as described in Reference Example 3 and 4.

B) Preparation of [Met$^{-1}$, Ala$^1$, Thr$^3$, Tyr$^4$, Arg$^5$, Ser $^{17,27,60,65}$]hu G-CSF modified with methyl polyethylene glycol 5000.

This was prepared as in Reference Example 14. The final product contained about 4 moles of methyl polyethylene glycol covalently bound per mole protein. The specific activity of unmodified derivative $1.5 \times 10^9$ U/mg fell to $2.0 \times 10^8$ U/mg (14%) in the modified product. The product was completely stable and showed no change in specific activity in solution at up to 10mg/ml (by protein) at 37° C. over 14 days.

REFERENCE EXAMPLE 23

Preparation of [Met$^{-1}$, Arg$^{11}$, Ser$^{17,27,60,65}$]human G-CSF modified with methyl polyethylene glycol 2000 a) Preparation of methyl polyethylene glycol p-nitrophenyl carbonate approx MW 2000.

To a solution of p-nitrophenylchloroformate (2.32 g, 11.5 mmole) in acetonitrile (250 ml) at 0°–5° was added with stirring methyl polyethylene glycol average MW 2000 (Sigma Chemical Co Ltd) (20 g, 10 mmol) followed by triethylamine (1.11 g, 1.53 ml, 11 mmol) dropwise. The mixture was allowed to warm to room temperature and stirred for 24hr at 20° C. Precipitated triethylammonium hydrochloride was removed by filtration (0.46 g of a theoretical 1,375 g) and the filtrate after dilution with 1l diethyl ether (anhydrous) was stored at 0°–5° C. for 24hr. A white precipitate was collected by filtration and reprecipitated by dissolving in a minimum volume of ethanol at 35°–40° C. and cooling to 0° C. The product was reprecipitated from acetonitrile/diethyl ether (1:5 v/v) to yield the final product which was washed with ether and dried in vacuo to give a white solid 15.5 g. Microanalysis found C, 53.5. H,9.1. N 0.4. Cl0 showing the absence of chloroformate in the product.

b) Preparation of [Met$^{-1}$, Arg$^{11}$, Ser$^{17,27,60,65}$]hu G-CSF modified with methyl polyethylene glycol 2000

A solution of {Met$^{-1}$, Arg$^{11}$, Ser$^{17,27,60,65}$]hu G-CSF (1.5 g) in PBS-azide (300 ml, 5mg/ml) was dialysed against 0.4 M sodium borate pHS.8 ($7 \times 71$) to a final volume of 375 ml (4mg/ml). To this solution was added dropwise with stirring a water solution (375 ml) of methyl polyethylene glycol p-nitrophenyl carbonate, approx MW 2000 (10.0 g, 60 equivalents, 12 equivalents per amino group on [Met$^{-1}$, Arg$^{11}$, Ser$^{17,27,60,65}$]hu G-CSF). The reaction was allowed to proceed at room temperature for 3hr with gentle stirring and quenched by dropwise addition of ethanolamine hydrochloride, pH8.0 (10 equivalents per mole of activated methyl polyethylene glycol). The reaction mixture was concentrated on a YM10 membrane in an Amicon stirred cell (MW cut off 10kDa) at 4° C. to a final retentate volume of 50 ml. The retentate was diluted with 0.1 M ammonium bicarbonate pH8.0 (450 ml) and reconcentrated to 50 ml as before. This procedure was repeated seven times. The final concentrate was transferred to a second Amicon stirred cell fitted with a YM30 membrane (MW cut off 30kDa), diluted to 500 ml and reconcentrated to 50 ml. This procedure was repeated twice and the product concentrated to a final volume of 50 ml. The concentrated solution of product was chromatographed in two equal parts on a column (5×90 cm) of Ultrogel AcA54 equilibrated with PBS-azide. Fractions containing the modified protein were identified by monitoring protein at 280 nm and methyl polyethylene glycol by iodine/potassium iodide titration (C R Acad Sci Paris 274, 1617, 1972) pooled and exhaustively dialysed against water. The final water solution was concentrated in an Amicon stirred cell fitted with a YM30 membrane to a volume of 50 ml. The concentrate was diluted with water to a volume of 500 ml, reconcentrated and the procedure repeated a further five times. The final concentrate was filtered through a 0.22 micron filter under sterile conditions and stored at 4° C. for further studies Protein estimates by amino acid analysis after acid hydrolysis indicated an overall recovery of 47% of [Met$^{-1}$, Arg$^{11}$, Ser$^{17,27,60,65}$]hu G-CSF in the final modified product. PAGE-SDS on the reaction mixture after 3hr, and on the final water solution of product indicated no unreacted protein remaining, all the product running as a high MW streak. Titration of filtrates and retentates with iodine/potassium iodide showed that the repeated ultrafiltration on a YM30 membrane removed essentially all non protein bound methyl polyethylene glycol derivatives. This was confirmed by chromatographic analysis by HPLC on rpC4 (Dynamax 300A 12 $\mu$) eluting with a gradient of 40 to 90% acetonitrile - 0.1% TFA in water - 0.1% TFA and monitoring UV absorption at 280mm which gave a single peak. Fractions were freeze dried, re-constituted in water and monitored for protein at 280 nm and methyl polyethylene glycol by titration with iodine/potassium iodide and showed one coincident peak. Any residual non protein bound methyl polyethylene glycol would have been detected as a distinct, early eluting iodine/potassium iodide positive peak.

Iodine/potassium iodide titration of the [Met$^{-1}$, Arg$^{11}$, Ser$^{17,27,60,65}$]hu G-CSF covalently bound to methyl polyethylene glycol 2000 gave erratic results and did not permit estimation of PEG:protein ratios. The specific biological activity of the unmodified derivative, 1.2×10$^9$U/mg, fell to 1.5×10$^8$ U/mg (13%) in the modified product. The product was completely stable and showed no change in specific activity in PBS solution at up to 10mg/ml (by protein) at 37° C. over 14 days.

REFERENCE EXAMPLE 24

Preparation of [Met$^{-1}$, Arg$^{11}$, Ser$^{17,27,60,65}$]human G-CSF modified with methyl polyethylene glycol 750 a) Preparation of methyl polyethylene glycol p-nitrophenyl carbonate Approx MW750.

To a solution of p-nitrophenylchloroformate (5.1 g, 25.3mmol) in acetonitrile (50 ml) at 0°–5° C. was added with stirring methyl polyethylene glycol average MW750 (Sigma Chemical Co Ltd) (20 g, 26.67mmol) followed by triethylamine (2.69 g, 3.71 ml, 26.63mmol) dropwise over 30min. The reaction mixture was allowed to warm to room temperature and stirred for 8 hr. Precipitated triethylammonium hydrochloride was removed by filtration from the reaction mixture and the filtrate diluted with diethyl ether (anhydrous) (1l), cooled to 0° C. for four hours and refiltered. A total of 3.4 g of triethylammonium hydrochloride was collected. The filtrate was evaporated under reduced pressure and dried in vacuo to yield 23.5 g of a yellow waxy solid.

Microanalysis found Cl 0% showing the absence of chloroformate in the product.

A solution of [Met$^{-1}$, Arg$^{11}$, Ser$^{17,27,60,65}$]hu G-CSF (250mg) in PBS-azide (50 ml) was dialysed against water and then against 0.4 M sodium borate pH8.8. To the final solution (50 ml) at room temperature was added, dropwise with stirring, a water solution (50 ml) of methyl polyethylene glycol p-nitrophenyl carbonate approx MW750 (100 equivalents, 20 equivalents per amino group on [Met$^{-1}$, Arg$^{11}$, Ser$^{17,27,60,65}$]hu G-CSF) . The reaction mixture was stirred at room temperature for 3hrs and quenched by the dropwise addition of ethanolamine hydrochloride pH8 (10 equivalents per mole of activated methyl polyethylene glycol).

The reaction mixture was transferred to an Amicon stirred cell fitted with a YM10 membrane (MW cut off 10kDa) and concentrated. The concentrate (25 ml) was diluted to 350 ml with 0.1 M ammonium bicarbonate pH8 and concentrated to approx 25 ml. This procedure was repeated five times. The final concentrate (27 ml) was chromatographed on a column (5×90 cm) of Ultrogel AcA54 equilibrated and eluted with PBS-azide. Fractions containing modified protein were identified by monitoring protein at 280 nm and methyl polyethylene glycol by iodine/potassium iodide titration, pooled and exhaustively dialysed against water. The final product was concentrated in an Amicon stirred cell filtered with a YM10 membrane. The final concentrate was sterile filtered through a 0.2 $\mu$ filter and stored at 4° C. for further studies.

Protein estimates by amino acid analysis after acid hydrolysis indicated an overall recovery of approximately 80% [Met$^{-1}$, Arg$^{11}$, Ser$^{17,27,60,65}$]hu G-CSF in the final modified product. PAGE-SDS on the product gave a sharp band and indicated no unreacted [Met$^{-1}$, Arg$^{11}$, Ser$^{17,27,60,65}$]hu G-CSF remained.

Titration of filtrates and retentates with iodine/potassium iodide showed that the repeated ultrafiltration at pH8.0 on a YM10 membrane removed essentially all non-protein bound methyl polyethylene glycol derivatives Iodine/potassium iodide titration of the [Met$^{-1}$, Arg$^{11}$, Ser$^{17,27,60,65}$]hu G-CSF covalently bound to methyl polyethylene glycol gave very erratic results and did not permit estimation of PEG:protein ratios. The specific biological activity of the unmodified derivative 1.2×10$^9$U/mg, fell to 4×10$^8$ U/mg (33%) in the modified product. The product was completely soluble and showed no change in specific activity in PBS solution at up to 10mg/ml (by protein) at 37° C. over 14 days.

REFERENCE EXAMPLE 25

Characterisation of G-CSF derivatives before modification with methyl polyethylene glycol A water solution of the derivatives of Reference Examples 1,3,7,8 and 13-24 (protein concentration about 1 mg/ml) were concentrated to at least 11mg/ml of protein on an Amicon YM10 membrane at 4° C. To prevent any precipitation during concentration, the starting solution pH5.5 was first adjusted to pH8.5 by the addition of ammonium hydroxide to a final concentration of about 0.25mM. After concentration the pH of the solution had fallen to about 8.0.

The concentrated protein solution was adjusted to 10mg/ml protein (estimated from a 1 mg/ml solution giving an $A_{280}$ of 1.0) by addition of 20 fold concentrated phosphate buffered saline. This 10mg/ml solution of derivative in 10mM sodium phosphate, 150mM sodium chloride, pH7.4 (PBS) provided a common stock solution from which to establish homogeneity, identity, biological activity and solution stability of the protein.

Each derivative was shown to be at least 95% one component by PAGE-SDS run under reducing and non-reducing conditions and by reverse phase HPLC. Repeated amino acid composition analysis after acid hydrolysis in 6NHCl at 110° C. provided amino acid ratios for each derivative, and an accurate measurement of the protein concentration in the stock solution. This protein concentration together with the mean of bioassay titres obtained on at least six different days was used to determine the specific activity of the derivative. N-terminal sequence analysis and electrospray mass spectrometric analysis of selected derivatives gave the expected sequences and molecular weights.

Stock solutions of G-CSF derivatives modified with methyl polyethylene glycol (Reference Examples 1,3,7,8 and 13-24) were prepared in a similar manner to provide the data set out in these reference examples.

REFERENCE EXAMPLE 26

Solution Stability of G-CSF and derivatives thereof

Approximate dilutions of the stock solution of G-CSF, derivatives thereof and of such G-CSF derivatives modified with methyl polyethylene glycol in phosphate buffered saline (PBS) at 4° C. described in Reference Example 25 were tested for solution stability. Solutions of 1 mg/ml, 5mg/ml and sometimes 10mg/ml of protein in PBS were incubated at 37° C. for 14 days. Solutions were inspected visually at regular intervals for signs of precipitation. After 14 days each solution was centrifuged at 14,000rpm for 20 minutes, the supernatant removed by decantation and any pellet re-dissolved in PBS containing 1% w/v N-lauroyl sarcosine. The total protein content in each supernatant and re-dissolved precipitate was estimated by $A_{280}$ measurements and the monomer content in unmodified G-CSF and derivatives thereof was estimated by reverse phase HPLC. These were expressed as a percentage of the corresponding data given by solutions at the start of incubation and by a 1 mg/ml solution incubated at 4° C. for 14 days. Variations between total protein and monomer estimates were observed only in some of the re-dissolved pellets. The percentage protein remaining in solution in the supernatants from each starting concentration can thus be determined.

Following modification with methyl polyethylene glycol, G-CSF and all derivatives showed complete solution stability at up to 10mg/ml as mentioned in Reference Examples 1,3,7,8 and 13-24.

The specific activity of the product in each supernatant after incubation was shown to be the same as in the starting solution, and no differences were observed on PAGE-SDS under reducing or non-reducing conditions.

REFERENCE EXAMPLE 27

Bioassays.

1) G-CSF Bioassay

A factor dependent cell line, Paterson - G-CSF (FDCP-G), obtained from the Paterson Institute, Manchester, England was cloned by limiting dilution in the presence of G-CSF. A G-CSF responsive clone, designated clone E7, was used to determine human recombinant G-CSF activity. 2.5 ×FDCP-G clone E7 cells in 100 µl of RPMI 1640+10% FCS was added to an equal volume of RPMI 1640+10% FCS containing G-CSF. Each G-CSF sample was measured over 10 doubling dilutions. The final volume of RPMI 1640 (see Moore GE et al (1967) JAMA, 199, 519) +10% FCS (foetal calf serum) in each well of 96-well microtitre plate was 200 µl. The microtitre plate was incubated at 37° C. in 5% $CO_2$ in a humidified incubator for 4 days. 1.0 µCi of titrated thymidine was added per well and incubated over the final 6 hours. Cells were harvested onto glass fibre filter papers and the level of radioactivity determined by liquid scintillation counting. The level of tritiated thymidine incorporation was found to be directly proportional to the amount of G-CSF present. The FDCP-G clone E7 assay was calibrated using recombinant human G-CSF obtained from Amersham International with a declared specific activity of 108 units/mE of protein.

The potencies of G-CSF samples were determined by comparison to a standard of known activity.

The units of G-CSF activity per ml were calculated according to the following formula:

$$\left[ \frac{\text{Dilution of G-CSF standard giving 50\% maximal increase in }^3\text{H-thymidine incorporation}}{\text{Dilution of sample giving 50\% maximal increase in }^3\text{H-thymidine incorporation}} \right] \times \begin{array}{l} \text{Units/ml} \\ \text{activity} \\ \text{in G-CSF} \\ \text{standard} \end{array}$$

Interleukin-2 (IL-2) bioassay

Interleukin-2 was assayed for biological activity by monitoring the growth of a murine IL-2 dependent cell line CTL as described by Robb et al, J Exp Med 160 1126 1986 except the cells were incubated with IL-2 for 48h and pulsed with $^3$H-thymidine for 6-8 hours.

Calcitonin Bioassay using T47D cells

The bioassay for calcitonin is based on the principle that the human breast cancer cell line T47D bears adenylate cyclase linked receptors for calcitonin (Martin et al (1980) Biochem Biophys Res Commun 98: 150-156). Stimulation of T47D cells by calcitonin leads to the production of increased intracellular levels of cyclic AMP which can be quantified by radioimmunoassay. The amount of calcitonin or PEGylated calcitonin in unknown samples can be quantified by comparison to a standard curve prepared using known standard samples of calcitonin or PEGylated calcitonin.

In the bioassay, T47D cells were prepared as a suspension in serum-free medium or phosphate buffered saline. The cells were aliquoted into test-tubes and stimulated with standard calcitonin or PEGylated calcitonin, or with samples containing calcitonin or PEGylated calcitonin, in the presence of $10^{-4}$ M isobutylmethylxanthine for 20 minutes. The incubation was stopped by placing the cell suspensions in a boiling water bath for five minutes. The cells were lysed by two cycles of freeze-thawing in the presence of 0.01% Triton X-100 and cell debris sedimented by centrifugation at 10,000xg for five minutes.

Cyclic AMP in the lysate supernatent was quantified by radioimmunoassay using a commercially available kit (Amersham International TRK432). A standard curve was prepared by plotting amount of standard calcitonin or PEGylated calcitonin against cyclic AMP levels. The amount of calcitonin or PEGylated calcitonin in the unknown samples was determined by interpolation from the appropriate standard curve.

REFERENCE EXAMPLE 28

Preparation of human calcitonin (hCT) modified with methyl polyethylene glycol 5000

Lyophilised chemically synthesised hCT was purchased from Cambridge Research Biochemicals, Gadbrook Park, Rudheath, Northwich, Cheshire, England. Reverse phase and ion exchange HPLC revealed a single peak. 300mg in 75 ml $H_2O$ was modified with methyl polyethylene glycol as described in Reference Example 3 except that 5 equivalents of reagent were used per amino group on hCT. The reaction mixture was diafiltered on an Amicon YM10 membrane (molecular weight cut off 10kDa) at 4° C. against O.1 M ammonium bicarbonate pHS.0 to remove unreacted hCT. The retentate was concentrated to 36 ml and the volume made up to 60 ml with 50mM sodium phosphate pH7.0 containing 1.7 M ammonium sulphate. This solution was chromatographed in 5×12 ml batches on a 8 ml phenyl-superose column (Pharmacia/LKB) equilibrated in 50mM sodium phosphate pH7.0 containing 0.68 M ammonium sulphate. Free methyl polyethylene glycol did not bind to the column under these conditions and was removed by washing. The hCT modified with methyl polyethylene glycol was eluted using 50mM sodium phosphate pH7.0. The eluted peptide was dialysed into water using a Spectrapor dialysis membrane (MW cut off 6-8kDa) and concentrated using an Amicon YM10 membrane at 4° C. to a final concentration of 11mg/ml as determined by amino acid analysis after acid hydrolysis. This product which contained 1.5 moles methyl polyethylene glycol covalently bound per mole of hCT retained biological activity and was free of unmodified starting material.

REFERENCE EXAMPLE 29

Preparation of human interleukin-2 (IL-2) modified with methyl polyethylene glycol 5000

Lyophilised recombinant human IL-2 produced in E.coli was obtained from Biosource International, California. It was greater than 98% pure as determined by SDS-PAGE. Methods for the production of IL-2 in E.coli and its subsequent purification have been described (Karo et al, Biochem, Biophys. Res. Commun. 130, 692 (1988); Liang et al, Biochem J. 229 429 (1985), Koths et al U.S. Pat. No. 4569790 (1986)). A solution of 211mg in 30 ml H20 was modified with methyl polyethylene glycol approx MW 5000 and purified as described in Reference Example 3 using 20 equivalents per amino group on IL-2. The final product contained 3.4 moles of methyl polyethylene glycol per mole of protein, was free of unmodified starting material and retained biological activity.

REFERENCE EXAMPLE 30

Construction of pICI 0080 a) Construction of pTB357 (also referred to herein as pLB 004

Plasmid pTB357 utilises a repressed tetracycline resistance determinant, as found on the naturally-occurring plasmid RP4. This repressed system shuts off expression of the tetA gene in the absence of tetracycline whereas most drug resistant mechanisms have constitutive expression.

The tet locus was first mapped on RP4 by Barth and Grinter (J.Mol. Biol.113: 455–474, 1977). This was shown to consist of adjacent genes: tetA, the structural resistance gene and tetR, the repressor gene and this region has been sequenced (Klock et al, J. Bacteriol: 161:326–332, 1985). These genes are located on adjacent BglII-SmaI and SmaI-SmaI fragments. The BglII site is unique in RP4 but there are five SmaI sites (Lanka, Lurz and Furste, Plasmid 10: 303–307, 1983).

i) Cloning the tetA +tetR genes

The plasmid RP4 is well documented (Datta et al, J. Bacteriol 108: 1244, 1971) and is freely available. Furthermore the plasmid RP4 has been deposited with the National Collection of Type Cultures, 61 Colindale Avenue, London, NW9 5HT under accession nos. 50078 and 50437. E. coli strains containing this plasmid were grown in selective broth cultures and plasmid DNA was isolated a scale-up of the Holmes and Quigley method (Holmes and Quigley, Anal. Biochem 114: 193–197, 1981). It was deproteinized by treatment with 2.5 M ammonium acetate and reprecipitated with isopropanol. This plasmid DNA was treated, according to the supplier's recommended conditions, with restriction enzyme BglII and cut to completion. It was then partially cut by XmaI by using diluted enzyme and short incubation times. XmaI is an isoschizomer of SmaI but which produces 4-nucleotide cohesive ends at its cut sites.

The vector plasmid pUC8 (Yanisch-Perron, Vieira and Messing, Gene 33: 103–119, 1985) was similarly prepared and cut with BamHI and XmaI to completion. The RP4 fragments were cloned into this vector by ligation with T4 ligase at 12° C. for 16 hours. This was used to transform E. coli C600 made competent by the calcium chloride method (Maniatis et al, Cold Spring Harbor Laboratory, 1982). Cultures were then plated onto medium which selected for tetracycline resistance.

E. coli C600 is freely available from numerous sources including many culture collections such as the E.coli Genetic Stock Centre, Yale University, USA under accession No GCSC 3004. The genotype of E.coli C600 is K12 thr-1 leuB6 thi-1 hsdS1 lacY1 tonA21 $\lambda^-$supE44.

Several colonies with this resistance were checked for the expected phenotype (ampicillin and tetracycline resistance but not the kanamycin resistance indicative of RP4 itself). Colonies with the correct resistances were subjected to clone analysis by isolating plasmid DNA (Holmes and Quigley method). These preparations were cut with EcoRI and HindIII and analysed by gel electrophoresis. This established the size of the cloned insert which was found to be the 2.45 kb predicted for the BglII - XmaI - XmaI fragment from RP4. A clone carrying this fragment containing the tetA and tetR genes was designated pTB344.

ii) Removal of the tet gene from pAT153

It was necessary to remove the tet gene from the vector plasmid pAT153 before inserting the tetA +tetR cassette from RP4 to prevent gene duplication which can be a source of genetic instability. Also the tet gene may not be effectively suppressed by the non-cognate tetR. The removal was done by isolating plasmid pAT153 DNA and cutting it with EcoRI and AvaI. Between these sites, synthetic olignucleotides with the sequence SEQ ID No.56 and SEQ ID NO:63:

```
5' AATTCGCATGCGGATCCATCGATC 3'
   3' GCGTACGCCTAGGTAGCTAGAGCC 5'
``` were cloned. These fit the EcoRI and AvaI cohesive ends and contain SphI, BamHI and ClaI sites in addition. After transformation and selected, colonies were tested for the loss of the tetracycline resistance determinant. Plasmid DNA from one clone was sequenced to confirm that the predicted sequence was correct. This plasmid was designated pCH19.

iii) Insertion of the tetA +tetR genes

The tetA and tetR genes were isolated from pTB344 on an EcoRI to PstI fragment. The pUC8 vector was destroyed by curring with SspI because it carries the same selection determinant (ampicillin resistance) as pCH19. Plasmid pCH19 DNA was cut with EcoRI and PstI and then ligated with the 2.45 kb fragment carrying the tet genes. This was used to transform E. coli C600, the culture being plated out under selection for tetracycline resistant colonies. The insertion of the tet genes was designed to replace most of the bla genes in pCH19 which should thus lose its ampicillin resistance determinant. Loss of ampicillin resistance from the transformants was confirmed. A few clones were then used to isolate plasmid DNA which was subjected to restriction analysis. This confirmed that the constructed plasmid had the intended structure. It was designated pTB351.

iv) Insertion of the cer sequence

The naturally-occuring plasmid ColEI is very stably maintained in E.coli, whereas its derivatives pBR322 and pAT153 are not. Summers and Sherratt (Cell, 36: 1097–1103, 1984) demonstrated that this was due to the derivatives not containing a short (283 bp) sequence called cer which is present in the parent plasmid. This sequence contains a site-specific plasmid multimer-resolution system which prevents the accumulation of plasmid multimers formed by homologous recombination. Such multimers have a deleterious effect on the process of partition which normally ensures stable inheritance of daughter plasmids during bacterial cell division.

The cer sequence (Summers, Det al MGG, 201, p334-338, 1985) was isolated from plasmid pKS492 (provided by D. Sherratt) as a 289 bp fragment by cutting with BamHI and TaqI. The plasmid pTB351 was isolated as DNA from a dam strain of E. coli to prevent its ClaI site being blocked by the dam+methylation system. This DNA was cut with BamHI and ClaI (both these sites having been introduced on the synthetic oligonucleotide for this cloning). The cer fragment was ligated with the cut vector and then used to transform E. coli C600, selection being made for tetracycline reisistance. Transformant colonies were subjected to clone analysis by AvaI restriction and gel electrophoresis. The presence of an extra DNA band of about 300 bp indicated the acquisition of the cer fragment. Further restriction analyses were used to confirm that resultant plasmids had the correct structure. One of these was designated pTB357 (FIG. 5) and also designated pLB004.

b) Plasmid pCH101

The plasmid pCH101 corresponds to pICI 0020 (see Example 1c) except that the EcoRI-SalI fragment (see FIG. 1) is replaced by a fragment consisting of the SEO ID No 50 (see FIG. 6 also) and the interferon α2 gene sequence as described by Edge M. D. et al, Nucleic Acids Research 1983, Vol11, p6419–6435. In this regard the 3'-terminal ATG codon of SEQ ID No 50 immediately precedes the TGT codon which codes for cysteine (amino acid 1) in the interferon α2 sequence of the above-mentioned Edge M. D. et al Nucleic Acids Research reference. The 5' nucleotide sequence GATC-CATG and the complementary 3' nucleotide sequence GTAC are thus omitted from the nucleotide sequence of the aforementioned reference.

c) Insertion of an Expression Cassette into pTB357

An expression cassette consisting of the trp promoter, a ribosome binding site and the interferon α2 gene was isolated from plasmid pCH101 (see b above) on an EcoRI to SphI restriction fragment. This was ligated into the production vector (pTB357) (see (a) above) similarly cut with EcoRI and SphI. This DNA was used to transform a competent culture of E. coli C600 and tetracycline resistant colonies were isolated. A few of these were tested by DNA clone analysis for the acquisition of the SstI restriction site carried on the expression cassette. Clones positive in this respect were further tested by restriction mapping to check that the expected construct was correct. They were also checked for the conferred capacity to produce interferon α2 protein as analysed on a polyacrylamide-SDS gel stained with Coomassie blue. One such confirmed clone was designated pLB005.

d) Insertion of T4 transcription terminator into pTB 244

The T4 transcription terminator sequence in the form of the SalI to HindIII fragment (67 bases pairs long) (see SEQ ID No. 48 and FIG. 4a) was inserted into the multicloning site of an intermediate vector pTB 244 (described in European Patent Publication No. 237,269) between its SalI and HindIII sites. Clone analysis was used to confirm the structure of this construct (pTB244. T4 ter). From this vector, an SstI to SphI fragment containing most of the multicloning site and the T4 terminator was then isolated. This was inserted into pLB005 similarly cut with SstI and SphI thereby substituting the interferon α2 gene but leaving a cassette consisting of the trp promoter, multicloning site and T4 terminator. This construct was confirmed by clone analysis and the plasmid designated pLB013.

e) Substitution of the multicloning site

The multicloning site in pLB013 is not ideal for this vector in several respects: the SalI, BamHI and SmaI sites are not unique but exist elsewhere on the plasmid. This fragment was therefore excised by cutting with SstI and XbaI (both unique) and synthetic oligonucleotides with the sequence of SEQ ID No. 51 and SEQ ID NO.60:

```
5' AGCTCCATATGGTACCAGATCTCTCGAGAGTACTT
   GGTATACCATGGTCTAGAGAGCTCTCATGAAGATC 5'
``` were inserted in its place. Clones were analysed for acquisition of the new restriction sites and then confirmed by sequencing. One such plasmid was designated pLBO14. The new cloning sites inserted in this way are: NdeI, KpnI, BglII, XhoI and ScaI with the previous XbaI and SalI following them.

f) Further modification

It was discovered that the adjacent SstI and NdeI sites in pLB014 could not be cut by both these restriction enzymes either simultaneously or sequentially presumably because of their close proximity. An additional sequence was therefore inserted between them. This was done by cutting pLBO14 with SstI and KpnI and then inserting the synthetic oligonucleotide of SEQ ID No. 52 and SEQ ID NO.61.

5' AGCTCAGCTGCAGCATATGGTAC
       GTCGACGTCGTATAC 5'

Figure 7:
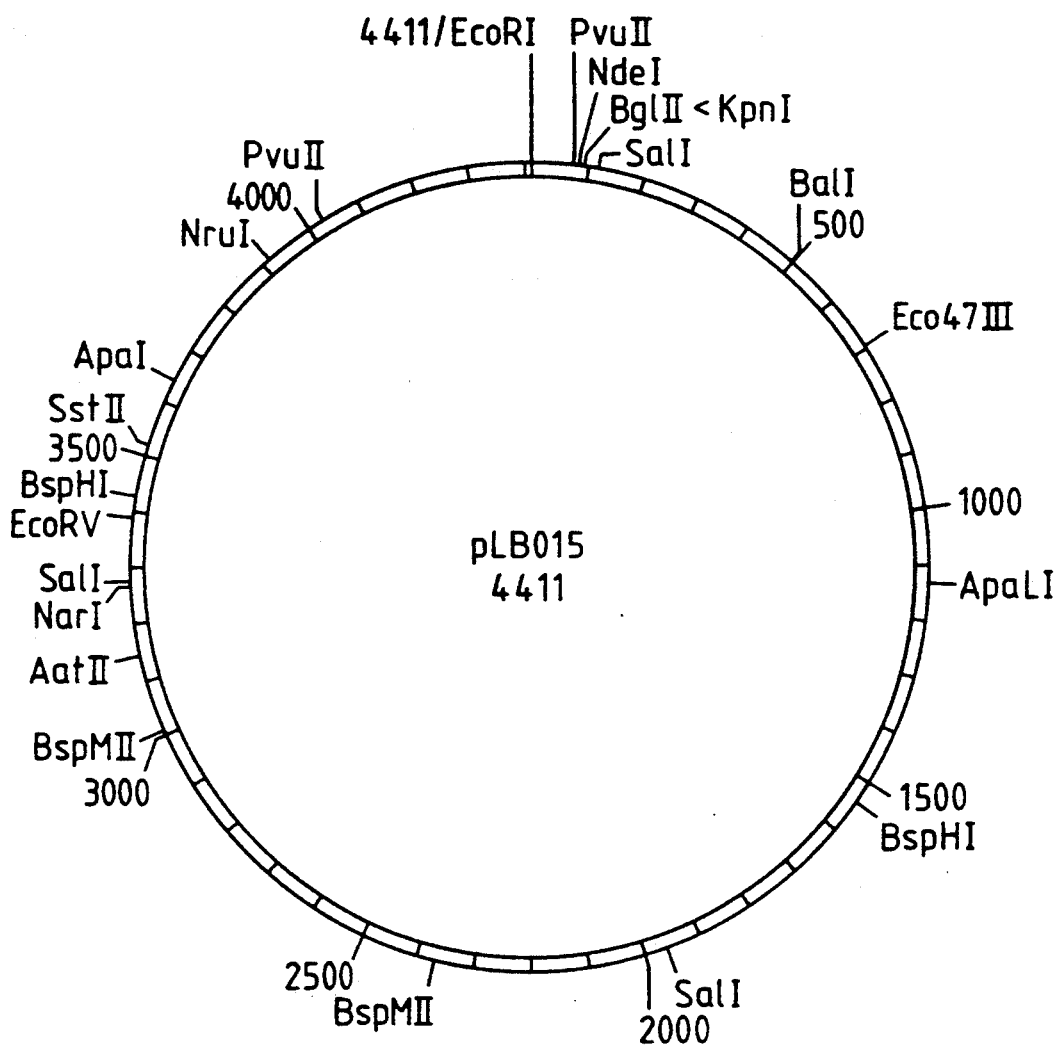
FIG. 7 shows a restriction map of pLB015(also referred to herein as pICI 0080)

Clones were analysed for acquisition of an extra PvuII or PstI site and then confirmed by sequencing. One such plasmid was designated pLB015 (=pICI 0080) (see FIG. 7). This plasmid, unlike pLB014, is efficiently cut by SstI and NdeI. This is to provide a place to insert a variety of ribosome binding site sequences correctly positioned with respect to the upstream trp promoter and with NdeI designed to provide the ATG start codon of the gene to be expressed.

REFERENCE EXAMPLE 31

Figure 8:
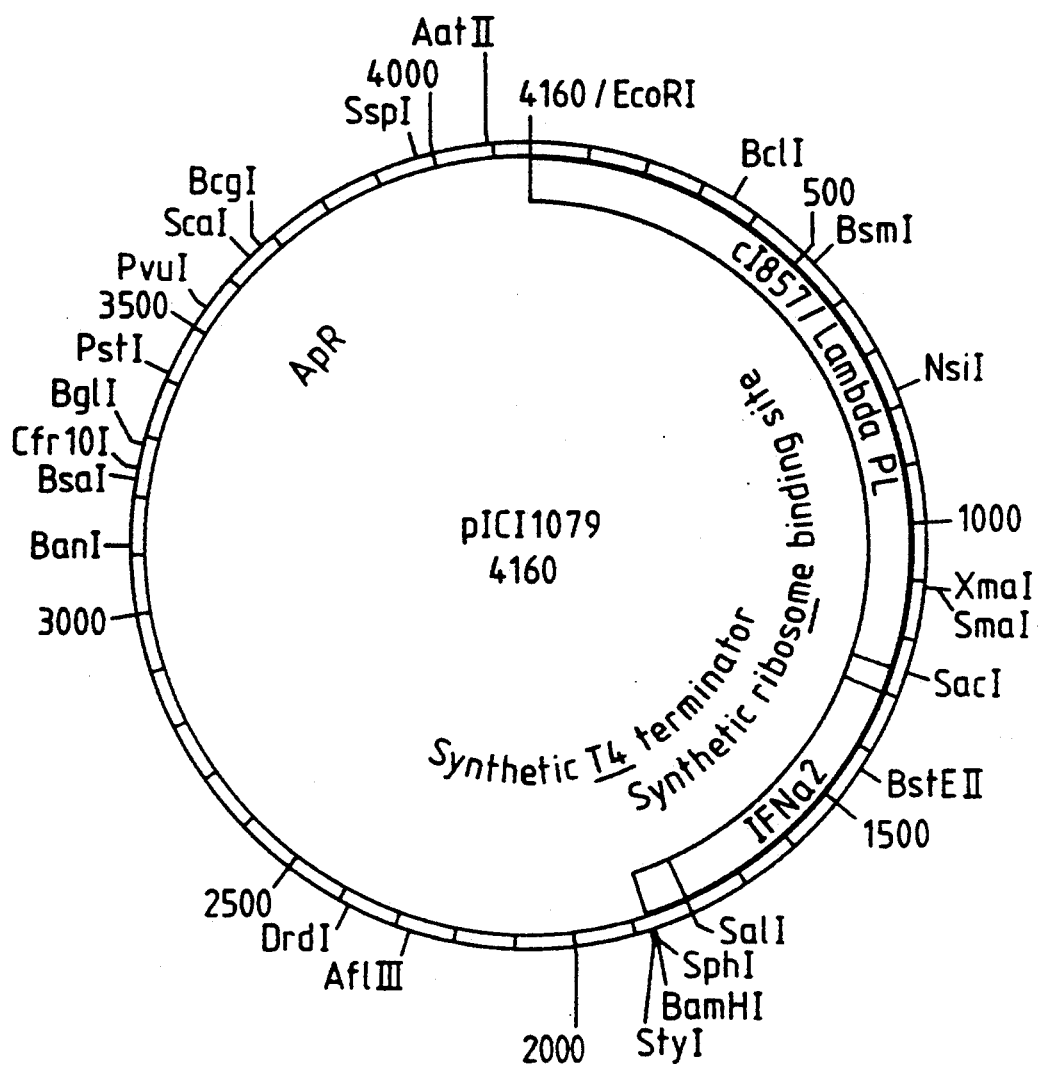
FIG. 8 shows a restriction map of pICI 1079.

Construction of plasmid pICI 1295 (also referred to as pCG300 a) Production of pCG54 from pICI1079 pICI1079 is an ampicillin resistant, pAT153-derived plasmid containing the following elements between the EcoRI and StyII restrictiion sites:
(i) a CI857 from phage λ;
(ii) a λP$_L$ promoter;
(iii) a synthetic ribosome binding site;
(iv) a synthetic interferon $α_2$ gene sequence;
(v) a synthetic transcription terminator sequence, derived from phage T4, between the SalI and StyI restriction sites. The DNA sequence of this transcription terminator is shown in FIG. 4 and SEQ ID No. 53 and SEQ ID NO.62.

pICI1079 is illustrated in FIG. 8.

pICI1079 has been deposited under the Budapest Treaty, at the National Collections of Industrial and Marine Bacteria Limited (NCIMB), 23 St. Machar Drive, Aberdeen, AB2 1RY, Scotland, UK. (NCIMB No 40370, date of deposit 19 Feb. 1991).

pCG54 was constructed in order to make available an expression vector containing the same promoter, ribosome binding site and transcription terminator sequences as above, i.e.: αp$_L$, RBS7 and T4, but lacking gene sequence encoding for production of a specific protein. Such a construct would provide the facility of a basic expression vector containing essential elements allowing transcription and translation for production of any protein of interest which could be introduced into this vector by subsequent cloning events.

Construction of the vector was initiated by restriction endonuclease cleavage of pICI1079 at its respective EcoRI and SalI sites. This cleavage step released a vector fragment containing the pICI1079 backbone complete with genes for plasmid replication and antibiotic resistance functions, plus the T4 transcription terminator sequence. The fragment was isolated by agarose gel purification steps using Geneclean for final purification of the DNA fragment.

To this vector fragment a second smaller DNA fragment of approximately 1.2Kb in size was introduced. This second fragment may be obtained, for example by DNA synthesis or by site directed or PCR mutagenesis of the small EcoRI-SalI restriction fragment obtained from pICI1079 as described above. This second fragment contained exactly equivalent promoter and ribosome binding site sequences as originally present in pICI1079 and additionally had EcoRI and SalI sites available at its 5' and 3' termini respectively, so providing compatible termini for ligation to the pICI1079 fragment. A ligation reaction in the presence of Gibco-BRL enzyme T4 DNA ligase and its respective buffer, resulted in the formation of the construct pCG54.

Clones containing this construct were originally isolated following transformation of an aliquot of the ligation reaction mixture into E.coli competent cells of strain HB101.

Figure 9:
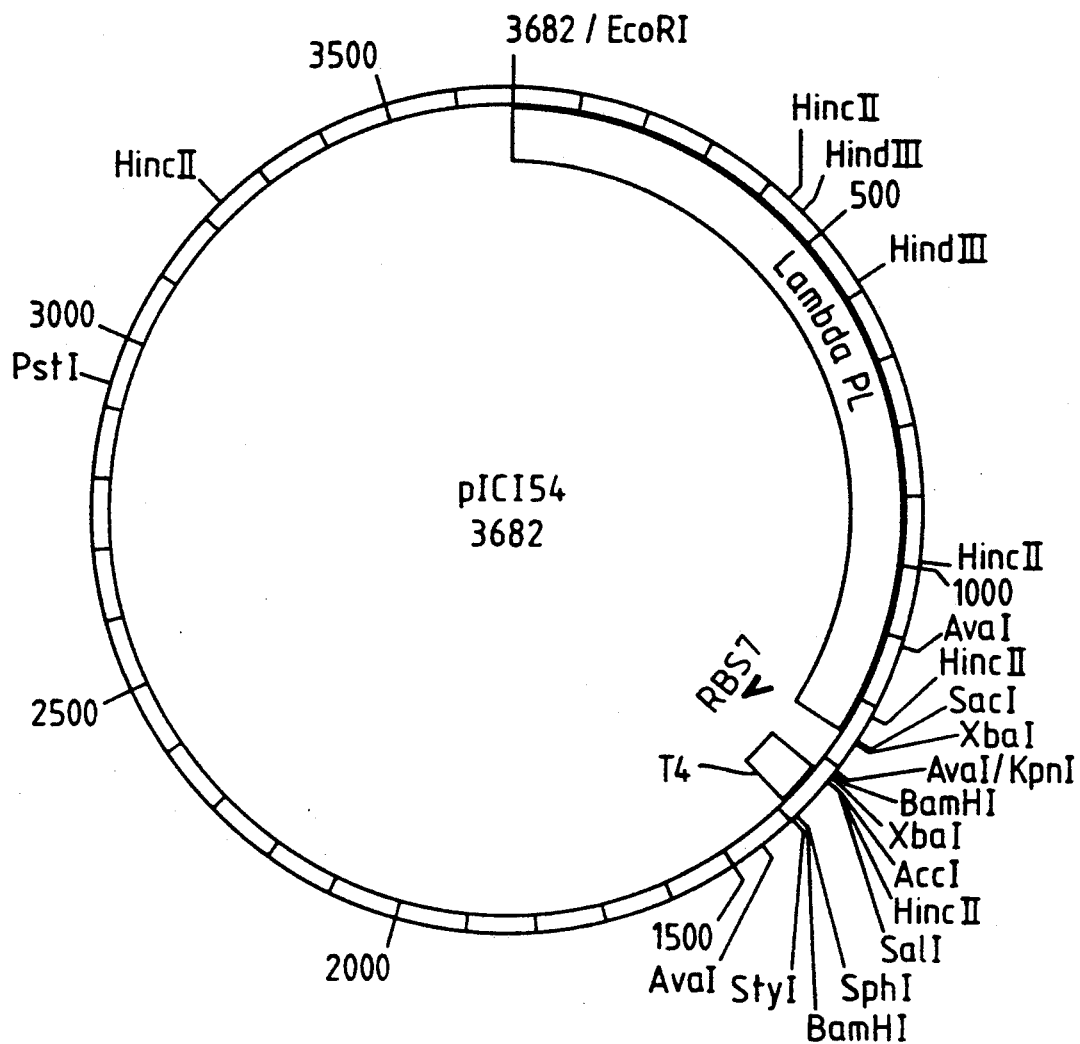
FIG. 9 shows a restriction map of pICI 54 (also referred to herein as pCG54)

The construct pCG54 recovered was 3.682Kb in size and contained essential features as outlined on the map featured in FIG. 9.

b) Production of pCG61 from pCG54 (also referred to as pICI54)

Synthetic oligonucleotide sequences were designed so as to include both the natural sequence for the T7A3 promoter and also a sequence which would provide an effective translation initiation region to enable correct processing of any polypeptide gene sequence cloned adjacent to it. A suitable candidate sequence for this latter region was identified as RBS1, the trp ribosome binding sequence. Therefore two complimentary oligonucleotides identified as SEQ ID No.54 and SEQ ID No.55 were synthesized to generate a double stranded DNA linker incorporating the T7A3 promoter and RBS1 sequences.

Oligonucleotides were prepared as 84mers by the standard protocol using an ABI gene synthesizer. They were designed so that in the double stranded form the synthetic fragments would have restriction endonuclease sites EcoRI and KpnI at the 5' and 3' ends respectively. Due to their length the oligomers could not be purified by means of HPLC and purification was undertaken by means of acrylamide gel electrophoresis using a 10% acrylamide: 7 M Urea gel.

Prior to purification, the oligomers were first checked on a sizing gel to ensure that not only are they of the correct size but that also the samples prepared contain as their greatest proportion the oligomers required and not a high contaminating proportion of smaller secondary oligonucleotides which result as by-products of synthesis.

The acrylamide gels were prepared by standard methods with ammonium persulphate and N,N,N',N'-tetramethylethylenediamine used as catalysts for gel polymerisation.

Sizing of the oligonucleotides required that they could be visualized after electropohoresis. It was therefore necessary to radioactively label the samples using $^{32}$p. This made it possible to assess sample quality following electrophoresis by way of autoradiography.

Oligonucleotide samples were supplied in a crude form unphosphorylated. This factor was made use of for radiolabelling purposes in that the samples could be 'hot' labelled at the 5' termini by phosphorylation using the enzyme T4 polynucleotide kinase.

Oligomers were provided from synthesis in an unphosphorylated form and so after purification each oligomer was individually subjected to a phosphorylation reaction in which ATP was used to phosphorylate the 5' end of each molecule in the presence of T4 polynucleotide kinase. (See Molecular Cloning: A Laboratory manual 2nd Edition, Sambrook, Fristch and Maniatis, p 5.68–5.71). Once phosphorylated the two complimentary oligonucleotides were annealed together to form the double strand DNA duplex containing the T7A3 promoter and the RBS1 sequence.

The vector molecule pCG54 was cleaved with restriction enzymes EcoRI and KpnI. On restriction digestion 2.3kb vector fragment and a 1.1kb fragment containing the λp$_L$ promoter and RBS1 sequence are generated. This cloning step is planned to replace the λpL-RBS1 sequence by EcoRI to KpnI synthetic fragment comprising the T7A3-RBS1 sequence. The 2.3kb vector fragment resulting from digestion of pCG54 was purified by the usual protocol using agarose gel electrophoresis and Geneclean methodology for removal of DNA from agarose fragments.

The 84bp EcoRI-KpnI synthetic fragment was ligated into the vector molecule prepared above and the ligated DNA used to transform E.coli HB101 cells. Selection of positive recombinant clones was by ampicillin resistance. Following transformation a number of colonies containing recombinant plasmid were selected for screening purposes.

The synthetic fragment incorporated into the vector during cloning was of a size (84 mer) such as to make restriction analysis of recombinant plasmid DNA samples inappropriate as a simple screening method. Inserts of such a small size are not readily apparent on agarose gel electrophoresis. The fragment itself contains no internal restriction endonuclease cleavage site which could be diagnostic of its presence. Initial screening of recombinant clones was therefore by the method of colony hybridisation (see Grunstein and Hoghess Proc. Natl Acad. Sci 72, 3961 (1975)). Nitrocellulose filters containing immobilized plasmid DNA from the recombinant clones were hybridised against a probe prepared by random radiolabelling of the synthetic annealed oligonucleotide SEQ ID No. 54 and SEQ ID No.55. The DNA was labelled using $\alpha^{32}$P-dCTP and incubation with Klenow polymerase at 37° C. for 2 hours. Recombinant colonies which generated a positive hybridisation reaction were selected for plasmid DNA preparation. Plasmid DNA was prepared in each case by a relatively large scale method incorporating CsCl gradient density centrifugation to ensure purity see "Molecular Cloning - A laboratory manual" second edition, Sambrook Fritsch and Maniatis (Cold Spring Harbor Laboratory, 1989) p1.42–1.52. Preparation of DNA by such a method ensures high quality material suitable for use in subsequent cloning manipulations and sequence analysis.

All plasmid DNA isolated from recombinant clones was included in a secondary screen by sequence analysis, to ensure that the oligonucleotide sequence at the cloning junctions and of the T7A3-RBS1 fragment itself was absolutely correct. The sequencing protocol used was that of Sequenase and the sequencing primer selected for use was for example pBR322 UP (pBR322 universal primer). Sequencing was effected using the Sanger dideoxy chain termination sequencing technique.

Figure 10:
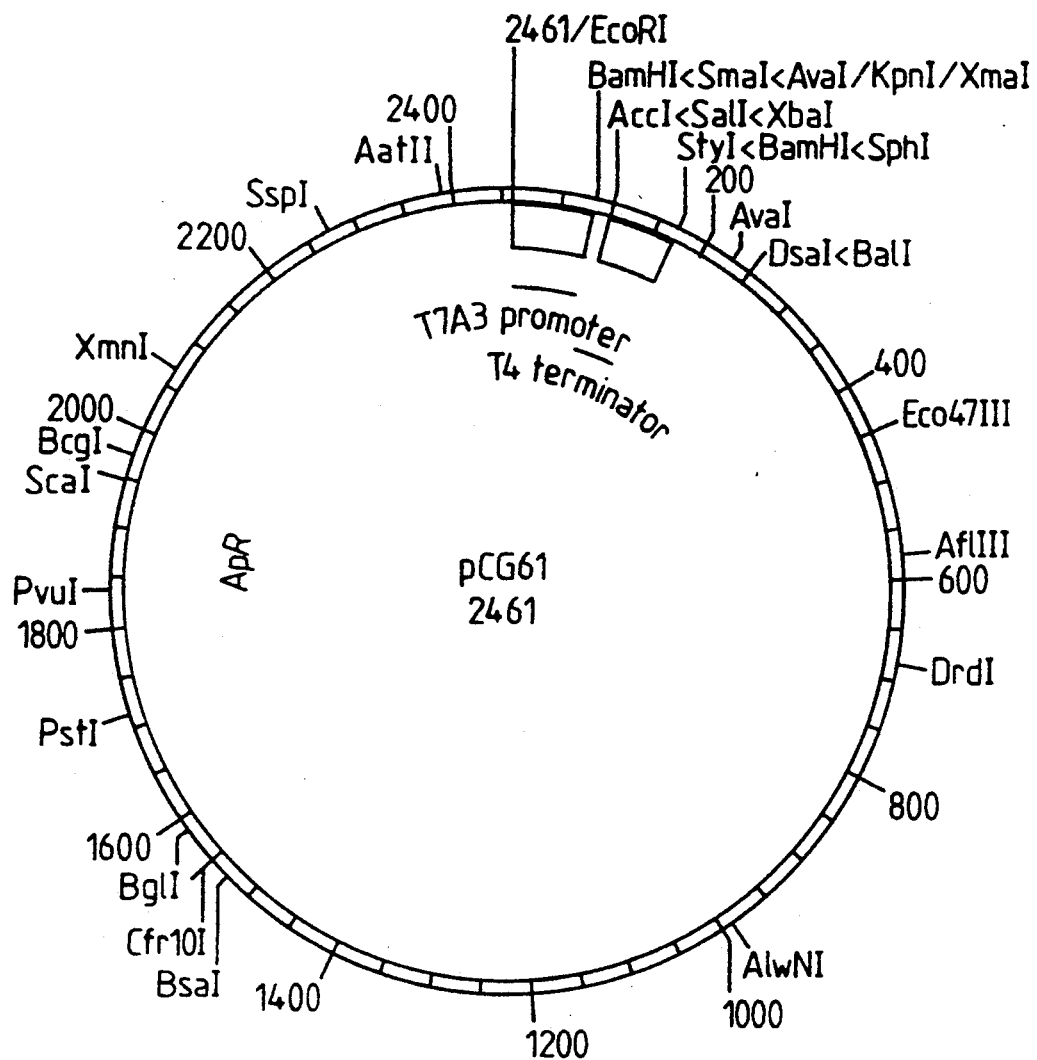
FIG. 10 shows a restriction map of pCG61.
Figure 11:
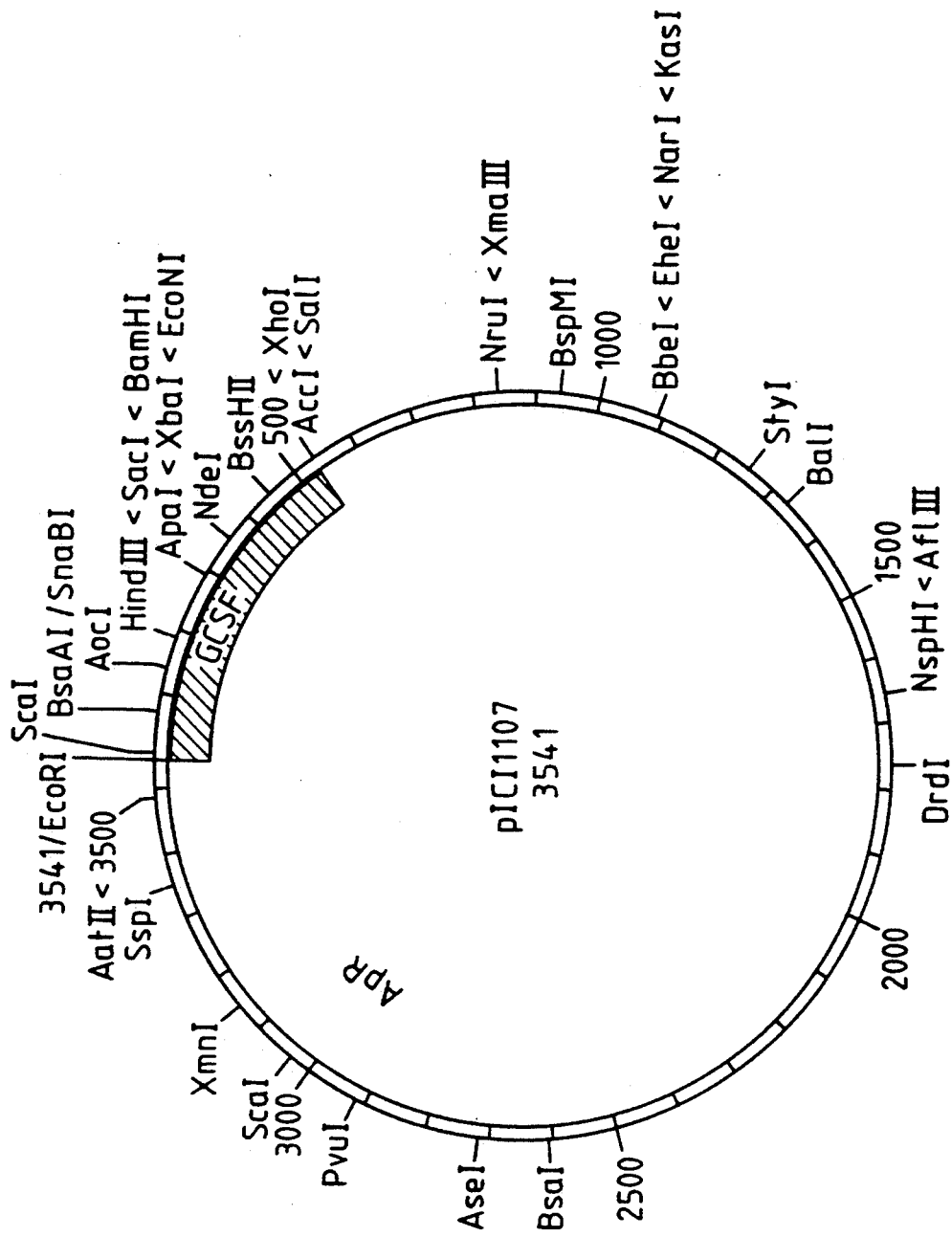
FIG. 11 shows a restriction map of pICI1107 in which the shaded area represents the gene sequence coding for [Ser$^{17,27}$]hu G-CSF.

Clones having the correct sequence were designated as the new expression construct pCG61, and contained the T7A3 promoter, RBS1 sequence and the T4 terminator sequence (see FIG. 10).

c) Production of pCG300 (also referred to as pICI 1295) from pCG61

The sequence and synthesis steps involved in construction of the G-CSF analogue [Ser$^{17,27}$]hu G-CSF (SEQ ID NO:46) are as described in Reference Example 3 (see FIG. 3). This G-CSF analogue sequence was isolated from a construct in which the gene had been incorporated into the plasmid pSTP1 to give pICI1107 (see Example 2). pICI1107 was digested with ScaI and the large fragment isolated following agarose gel electrophoresis and Geneclean purification. This fragment was then digested with the restriction endonuclease SalI to generate a [Met$^{-1}$, Ser$^{17,27}$]hu G-CSF gene on a ScaI to SalI restriction fragment suitable for cloning into pCG61 (see FIG. 10).

Following restriction with SalI the required fragment was isolated using agarose gel purification techniques once again.

The vector molecule pCG61 was digested with restriction enzyme KpnI. Cleavage with this enzyme creates a 3' overhang which was then blunt-ended using the enzyme T4 polymerase see "Molecular Cloning —a Laboratory manual" Second Edition Sambrook, Fritsch and Maniatis, p5.44–5.47. T4 polymerase activity was heat inactivated by incubation at 70° C. for 30 minutes and the DNA was recovered by ethanol precipitation. The pellet was dissolved in sterile distilled water and the solubilized DNA cleaved with SalI. The KpnI (now blunt-ended) to SalI vector fragment was recovered by means of ethanol precipitation followed by agarose gel electrophoresis and purification techniques.

The ScaI to SalI [Met$^{-1}$, Ser$^{17,27}$]hu G-CSF fragment was then ligated into the blunt-ended KpnI to SalI vector. Ligated DNA was transformed into E.coli strain HB101. Selection of recombinant clones was for ampicillin resistance.

Initial screening of potential recombinant clones was by means of hybridisation. A radiolabelled probe was prepared by random labelling of an EcoRI to SaiI fragment (containing the [Met$^{-1}$, Ser$^{17,27}$]hu G-CSF gene sequence) prepared from the plasmid pICI1107. This was used in hybridisation against colonies whose DNA had been immobilized onto the surface of nitrocellulose filters. Subsequently plasmid DNA was prepared from 24 clones which had been hybridised in this screen. All DNA preparations were by the rapid mini-prep method see Birnboim and Doly, Nucleic Acids Research, Z, 1513, 1979. These recombinant DNA preparations were subjected to a secondary screen by way of restriction analysis. Linearization of the DNA with BamHI, which is a unique site within the expression cassette, is indicative of the presence of the [Met$^{-1}$, Ser$^{17,27}$]hu G-CSF sequence.

Figure 12:
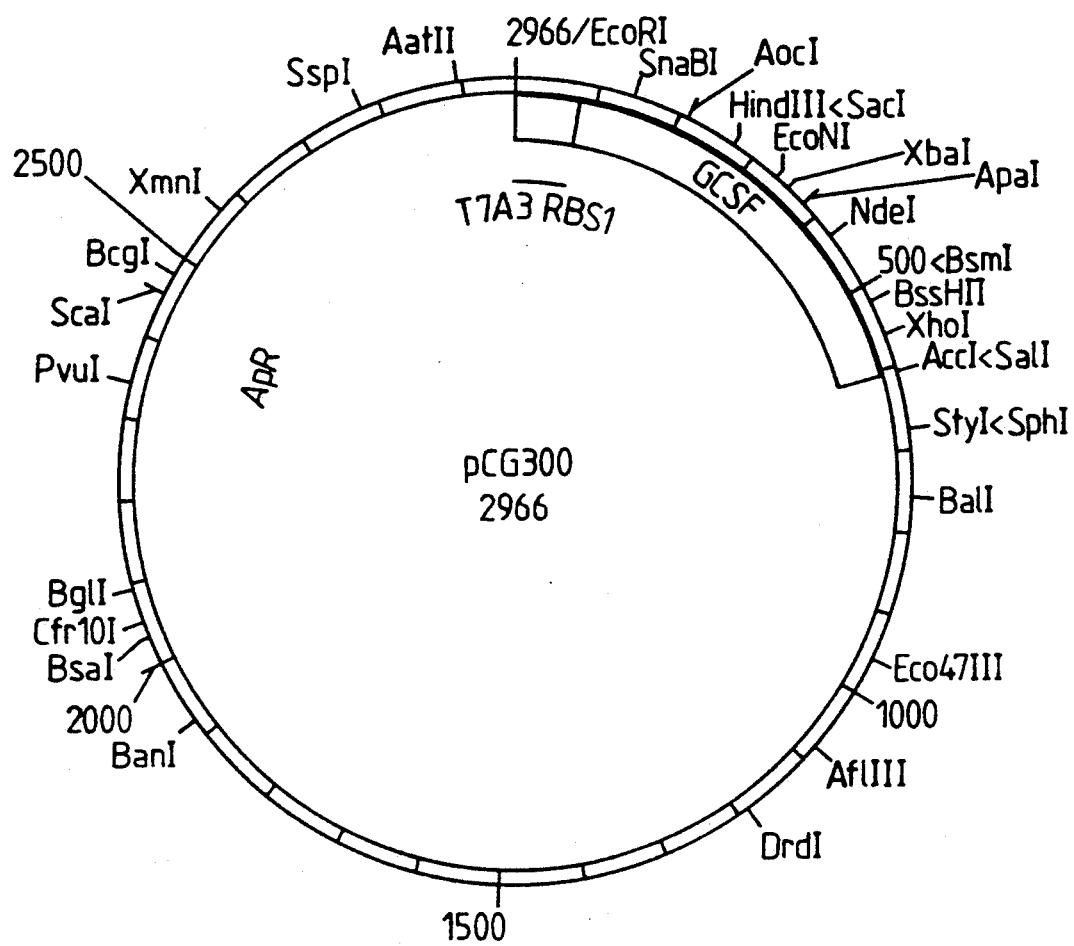
FIG. 12 shows a restriction map of pCG300 (also referred to herein as pICI 1295)

Sequence analysis was performed to confirm the presence of the [Met$^{-1}$, Ser$^{17\ 27}$]hu G-CSF gene and to verify that the base sequence at the cloning junctions and throughout the [Met$^{-1}$, Ser$^{17,27}$]hu G-CSF gene was correct. For this purpose large scale plasmid DNA samples were prepared from 16 recombinant clones using the CsCl gradient density centrifugation technique to ensure purity. Sequencing steps were performed in accordance with the sequence protocol and the sequencing primer selected was the pBR322 universal primer (EcoRI). Two of the recombinant clones contained the correct sequence at the ScaI end of the [Met$^{-1}$, Ser$^{17,27}$]hu G-CSF fragment and throughout the G-CSF peptide sequence itself. The clones were identified as expression construct pCG300 (see FIG. 12).

---

What is claimed is:

1. A pharmaceutical composition for continuous release of an acid stable physiologically active substance from material of the composition into an aqueous physiological-type environment, wherein said acid stable physiologically active substance is a polypeptide covalently conjugated to a water soluble polymer, which acid stable physiologically active substance is not significantly hydrolysed under the conditions encountered within the composition during the period of use, which composition,
    i) when placed in an aqueous physiological-type environment, releases the polypeptide into the aqueous physiological-type environment in a continuous manner, giving a release profile which is essentially monophasic over a period of at least one week;
    ii) exhibits two successive phases of release of the polypeptide, the first phase being released by diffusion from the surface and the second phase being released consequent upon degradation of material of the composition, wherein the diffusion phase and the degradation-induced phase overlap in time, and release of polypeptide occurs over a period of at least one week; or
    iii) absorbs water in a continuous manner, giving a water absorption profile which is essentially monophasic, until the material of the composition has been degraded and essentially all of the polypeptide has been released into the aqueous physiological-type environment, over a period of at least one week;
wherein the polypeptide is selected from the group consisting of 1) human G-CSF; 2) [$Ser^{17}$]human G-CSF, and 3) a derivative of naturally occurring G-CSF having at least one of the biological properties of naturally occurring G-CSF and a solution stability of at least 35% at 5 mg/ml, the said derivative having at least one Cys$^{17}$ of the native sequence replaced by a Ser$^{17}$ residue and Asp$^{27}$ of the native sequence replaced by a Ser$^{27}$ residue.

2. A pharmaceutical composition as claimed in claim 1 wherein one molecule of physiologically active substance comprises at least one molecule of water soluble polymer per 3000–8000 Da molecular weight of polypeptide.

3. A pharmaceutical composition as claimed in claim 1 wherein the polypeptide comprises at least one further modification selected from:
    a) Glu$^{11}$ of the native sequence replaced by an Arg$^{11}$ residue;
    b) Leu$^{15}$ of the native sequence replaced by a Glu$^{15}$ residue;
    c) Lys$^{23}$ of the native sequence replaced by an Arg$^{23}$residue;
    d) Gly$^{26}$ of the native sequence replaced by an residue;
    e) Gly$^{28}$ of the native sequence replaced by an Ala$^{28}$ residue;
    f) Ala$^{30}$ of the native sequence replaced by an Lys$^{30}$or Arg$^{30}$ residue;
    g) Lys$^{34}$ of the native sequence replaced by an Arg$^{34}$ residue;
    h) Lys$^{40}$y of the native sequence replaced by an Arg$^{40}$ residue;
    i) Pro$^{44}$ of the native sequence replaced by an Ala$^{44}$ residue;
    j) Leu$^{49}$ of the native sequence replaced by a Lys$^{49}$ residue;
    k) Gly$^{51}$ of the native sequence replaced by an Ala$^{51}$ residue;
    l) Gly$^{55}$ of the native sequence replaced by an Ala$^{55}$ residue;
    m) Trp$^{58}$ p of the native sequence replaced by a Lys$^{58}$ residue;
    n) Pro$^{60}$ of the native sequence replaced by a Ser$^{60}$ residue;
    o) Pro$^{65}$ of the native sequence replaced by a Set$^{65}$ residue;
    p) Pro$^{111}$ of the native sequence replaced by a Glu$^{111}$ residue;
    q) Thr$^{115}$ of the native sequence replaced by a Set$^{115}$ residue;
    r) Thr$^{116}$ of the native sequence replaced by a Ser$^{116}$ residue; and
    s) Tyr$^{165}$ of the native sequence replaced by an Arg$^{165}$ residue.

4. A pharmaceutical composition as claimed in claim 1, wherein the polypeptide is selected from:
    i) [Arg$^{11}$, Ser$^{17,27,60,65}$]human G-CSF,
    ii) [Glu$^{15}$, Ser$^{17,27}$, Ala$^{26,28}$, Lys$^{30}$]human G-CSF,
    iii) [Arg$^{11}$, Glu$^{15}$, Ser$^{17,27,60,65}$, Ala$^{26,28}$, Lys$^{30}$]human G-CSF,
    iv) [Arg$^{11,40}$, Ser$^{17,27,60,65}$]human G-CSF,
    v) [Arg$^{11,40}$,Ser$^{17,27,60,65}$]human G-CSF,
    vi) [Arg$^{11,165}$,Glu$^{15}$,Ser$^{17,27,60,65}$, Ala$^{26,28}$,Lys$^{30,58}$]human G-CSF
    vii) [Arg$^{11}$,Glu$^{15,111}$,Ser$^{17,27,60,65,115,116}$, Ala$^{26,28}$, Lys$^{30}$]human G-CSF,
    viii) [Glu$^{15}$, Ser$^{17,27}$,Ala$^{26,28}$,Arg$^{30}$]human G-CSF, and ix) [Ala$^1$, Thr$^3$, Tyr$^4$, Ar$^{5,11}$, Ser$^{17,27}$]human G-CSF
x) [Ser$^{17,27,60,65}$]human G-CSF
xi) [Arg$^{11}$, Ser$^{17,27,65}$]human G-CSF, and
xii) [Ser17,27,65]human G-CSF 5. A pharmaceutical composition as claimed in claim 1 wherein the water soluble polymer is selected from a polyethylene glycol or polypropylene glycol homopolymer, a polyoxyethylated polyol or a polyvinyl alcohol wherein the homopolymer is unsubstituted or substituted at one end with an alkyl group.

6. A pharmaceutical composition as claimed in claim 1 wherein the water soluble polymer is selected from unsubstituted polyethylene glycol, monomethylpolyethylene glycol and polyoxyethylated glycerol.

7. A pharmaceutical composition as claimed in claim 1 wherein the water soluble polymer has a molecular weight of 1000 to 15,000.

8. A pharmaceutical composition as claimed in claim 1, wherein the physiologically active substance is [Arg$^{11}$, Ser$^{17,27,65}$]human G-CSF, with or without a presequence methionine, conjugated to monomethyl polyethylene glycol, in which the monomethyl polyethylene glycol has a molecular weight of 2000–5000.

9. A method for providing haematopoietic therapy to a mammal which comprises administering a pharmaceutical composition as claimed in claim 1 to said mammal whereby to deliver an effective amount of a polypeptide conjugated to water soluble polymer.

10. A method for arresting the proliferation of leukaemic cells in a mammal which comprises administering a pharmaceutical composition as claimed in claim 1 to said mammal whereby to deliver an effective amount of a polypeptide conjugated to water soluble polymer.

* * * * *

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AATTCAGTAC TCCACTGGGT CCAGCAAGCT CTCTGCCGCA GTCTTTCCTG CTGAAGTGTC      60
TC                                                                    62
```

( 2 ) INFORMATION FOR SEQ ID NO:2:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CTGTTCGAGA CACTTCAGCA GGAAAGACTG CGGCAGAGAG CTTGCTGGAC CCAGTGGAGT      60
ACTG                                                                  64
```

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAACAGGTAC GTAAAATTCA AGGCGATGGT GCGGCTCTGC AGGAAAAGCT GTGCGCAACC      60
```

( 2 ) INFORMATION FOR SEQ ID NO:4:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TTTGTAGGTT GCGCACAGCT TTTCCTGCAG AGCCGCACCA TCGCCTTGAA TTTTACGTAC      60
```

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TACAAACTGT GCCACCCTGA GGAACTGGTG CTGCTCGGTC ACTCTCTG                  48
```

( 2 ) INFORMATION FOR SEQ ID NO:6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CGGGATCCCC AGAGAGTGAC CGAGCAGCAC CAGTTCCTCA GGGTGGCACA G                    51
```

( 2 ) INFORMATION FOR SEQ ID NO:7:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

```
GGGATCCCGT GGGCTCCACT GAGCTCTTGC CCGTCCCAAG CTTTACAACT GGCAGGCTGC           60
TTG                                                                         63
```

( 2 ) INFORMATION FOR SEQ ID NO:8:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

```
CTGGCTCAAG CAGCCTGCCA GTTGTAAAGC TTGGGACGGG CAAGAGCTCA GTGGAGCCCA           60
```

( 2 ) INFORMATION FOR SEQ ID NO:9:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:9:

```
AGCCAGCTGC ACTCCGGTCT GTTCCTGTAC CAGGGTCTGC TGCAGGCTCT AGAAGGCATC           60
TCT                                                                         63
```

( 2 ) INFORMATION FOR SEQ ID NO:10:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

```
TTCAGGAGAG ATGCCTTCTA GAGCCTGCAG CAGACCCTGG TACAGGAACA GACCGGAGTG           60
CAG                                                                         63
```

( 2 ) INFORMATION FOR SEQ ID NO:11:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

```
CCTGAATTGG GGCCCACCCT GGACACACTG CAGCTGGACG TTGCCGACTT CGCTACTACC           60
```

( 2 ) INFORMATION FOR SEQ ID NO:12:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

TTGCCATATG GTAGTAGCGA AGTCGGCAAC GTCCAGCTGC AGTGTGTCCA GGGTGGGCCC    60

CAA    63

( 2 ) INFORMATION FOR SEQ ID NO:13:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATATGGCAAC AGATGGAGGA ACTGGGTATG GCTCCGGCAC TGCAGCCGAC TCAGGGTGCG    60

ATG    63

( 2 ) INFORMATION FOR SEQ ID NO:14:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

TGCTGGCATC GCACCCTGAG TCGGCTGCAG TGCCGGAGCC ATACCCAGTT CCTCCATCTG    60

( 2 ) INFORMATION FOR SEQ ID NO:15:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CCAGCATTCG CCTCTGCTTT CCAGCGGCGC GCAGGCGGTG TTCTGGTTGC CTCCCATCTT    60

( 2 ) INFORMATION FOR SEQ ID NO:16:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GCTCTGAAGA TGGGAGGCAA CCAGAACACC GCCTGCGCGC CGCTGGAAAG CAGAGGCGAA    60

( 2 ) INFORMATION FOR SEQ ID NO:17:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CAGAGCTTCC TCGAGGTGTC TTACCGCGTT CTGCGTCACC TGGCCCAGCC GTTAG    55

( 2 ) INFORMATION FOR SEQ ID NO:18:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGACTTACG GCTGGGCCAG GTGACGCAGA ACGCGGTAAG ACACCTCGAG GAA    53

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TACAACTGGC AGGCTGCTTG A    21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GACGTTGCCG ACTTCGCTAC T    21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

TGCCGGAGCC ATACCCAGTT C    21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCCTGCCAGT TGTAAAGCTT G    21

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GCACCATCGC CTTGAATTTT ACGTAG    26

( 2 ) INFORMATION FOR SEQ ID NO:24:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCAGTAC TCCACTGGGT CCAGCAAGCT CTCTGCCGCA GTCTTTCCTG CTGAAGTCTC    60

TC                                                                                                    62

(2) INFORMATION FOR SEQ ID NO:25:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:25:

CTGTTCGAGA GACTTCAGCA GGAAAGACTG CGGCAGAGAG CTTGCTGGAC CCAGTGGAGT        60

ACTG                                                                                                  64

(2) INFORMATION FOR SEQ ID NO:26:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:26:

GAACAGGTAC GTAAAATTCA AGGCAGCGGT GCGGCTCTGC AGGAAAAGCT GTGCGCAACC        60

(2) INFORMATION FOR SEQ ID NO:27:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:27:

TTTGTAGGTT GCGCACAGCT TTTCCTGCAG AGCCGCACCG CTGCCTTGAA TTTTACGTAC        60

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:28:

CTTCAGCAGG AAAGAACGCG GCAGAGAGC                                                                       29

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:29:

GCTTGGGAAG AGCAAGAGCT CAGAGAAGCC CAC                                                                  33

(2) INFORMATION FOR SEQ ID NO:30:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:30:

CTGTTGCCAT ATGCTAGAAG CGAAGTCTTC AACGTCCAGC                                                           40

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GCTCAGTGGA GCTTTCGGGA TCCCCAG                              27

( 2 ) INFORMATION FOR SEQ ID NO:32:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ACGCAGAACG CGGCGAGACA CCTCGAG                              27

( 2 ) INFORMATION FOR SEQ ID NO:33:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

GTTCGAGAGA CTTTTCCAGG AAAGACTGC                           29

( 2 ) INFORMATION FOR SEQ ID NO:34:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

CCTGCAGTTT CGCAGCGCTA GCTTGAATTT TAC                      33

( 2 ) INFORMATION FOR SEQ ID NO:35:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CAGAGAGTGA GCGAGCTTCA CCAGTTCCTC AGCGTGG               37

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

GCTCAGTGGA GCTTTCGGGA TAGCCAGAG                           29

( 2 ) INFORMATION FOR SEQ ID NO:37:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:37:

CAGCTTTTCC TGCAGACGCG CAGCGCTAGC    30

( 2 ) INFORMATION FOR SEQ ID NO:38:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

CCGCTGCCTT GAATACGACG TACCTGTTC    29

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GGTTGCGCAC AGACGTTCCT GCAGAGCCGC    30

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGTGGCACAG ACGGTAGGTT GCGCACAGC    29

( 2 ) INFORMATION FOR SEQ ID NO:41:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

CGCGGCAGAG AGCTTGCACG GTAGGTTGGA GCCATTGTCG ATACC    45

( 2 ) INFORMATION FOR SEQ ID NO:42:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

GTACCTGTTC GAGAGAACGC AGCAGGAAAG A    31

( 2 ) INFORMATION FOR SEQ ID NO:43:

( i ) SEQUENCE CHARACTERISTICS:
        ( A ) LENGTH: 174 amino acids
        ( B ) TYPE: amino acid
        ( D ) TOPOLOGY: linear ( i x ) FEATURE:
    ( A ) NAME/KEY: Modified-site
    ( B ) LOCATION: 36
    ( D ) OTHER INFORMATION: /note="Xaa is either Cys or is
        Val Ser Glu Cys"

( x i ) SEQUENCE DESCRIPTION: SEQ ID NO:43:

```
Thr Pro Leu Gly Pro Ala Ser Ser Leu Pro Gln Ser Phe Leu Leu Lys
 1           5                   10                  15

Cys Leu Glu Gln Val Arg Lys Ile Gln Gly Asp Gly Ala Ala Leu Gln
            20                  25                  30

Glu Lys Leu Xaa Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                      70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

( 2 ) INFORMATION FOR SEQ ID NO:44:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

```
AATTCTGGCA AATATTCTGA AATGAGCTGT TGACAATTAA TCATCGAACT AGTTAACTAG      60
TACGCAAGTT CACGTAAAAA GGGTATCGAC AATGGTACCC GGGGATCCTC TAGAGTCGAC     120
CTGCAGGCAT GCAAGCTTAG CCCGCCTAAT GAGCGGGCTT TTTTTTAT                  168
```

( 2 ) INFORMATION FOR SEQ ID NO:45:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 9..530

( x i ) SEQUENCE DESCRIPTION: SEQ ID NO:45:

```
AATTCAGT ACT CCA CTG GGT CCA GCA AGC TCT CTG CCG CAG TCT TTC CTG      50
         Thr Pro Leu Gly Pro Ala Ser Ser Leu Pro Gln Ser Phe Leu
          1           5                   10

CTG AAG TGT CTC GAA CAG GTA CGT AAA ATT CAA GGC GAT GGT GCG GCT       98
Leu Lys Cys Leu Glu Gln Val Arg Lys Ile Gln Gly Asp Gly Ala Ala
 15              20                  25                  30
```

```
CTG CAG GAA AAG CTG TGC GCA ACC TAC AAA CTG TGC CAC CCT GAG GAA      146
Leu Gln Glu Lys Leu Cys Ala Thr Tyr Lys Leu Cys His Pro Glu Glu
                 35                  40                  45

CTG GTG CTG CTC GGT CAC TCT CTG GGG ATC CCG TGG GCT CCA CTG AGC      194
Leu Val Leu Leu Gly His Ser Leu Gly Ile Pro Trp Ala Pro Leu Ser
             50                  55                  60

TCT TGC CCG TCC CAA GCT TTA CAA CTG GCA GGC TGC TTG AGC CAG CTG      242
Ser Cys Pro Ser Gln Ala Leu Gln Leu Ala Gly Cys Leu Ser Gln Leu
         65                  70                  75

CAC TCC GGT CTG TTC CTG TAC CAG GGT CTG CTG CAG GCT CTA GAA GGC      290
His Ser Gly Leu Phe Leu Tyr Gln Gly Leu Leu Gln Ala Leu Glu Gly
     80                  85                  90

ATC TCT CCT GAA TTG GGG CCC ACC CTG GAC ACA CTG CAG CTG GAC GTT      338
Ile Ser Pro Glu Leu Gly Pro Thr Leu Asp Thr Leu Gln Leu Asp Val
 95                 100                 105                 110

GCC GAC TTC GCT ACT ACC ATA TGG CAA CAG ATG GAG GAA CTG GGT ATG      386
Ala Asp Phe Ala Thr Thr Ile Trp Gln Gln Met Glu Glu Leu Gly Met
                115                 120                 125

GCT CCG GCA CTG CAG CCG ACT CAG GGT GCG ATG CCA GCA TTC GCC TCT      434
Ala Pro Ala Leu Gln Pro Thr Gln Gly Ala Met Pro Ala Phe Ala Ser
            130                 135                 140

GCT TTC CAG CGG CGC GCA GGC GGT GTT CTG GTT GCC TCC CAT CTT CAG      482
Ala Phe Gln Arg Arg Ala Gly Gly Val Leu Val Ala Ser His Leu Gln
        145                 150                 155

AGC TTC CTC GAG GTG TCT TAC CGC GTT CTG CGT CAC CTG GCC CAG CCG      530
Ser Phe Leu Glu Val Ser Tyr Arg Val Leu Arg His Leu Ala Gln Pro
    160                 165                 170

TAAG                                                                  534
```

( 2 ) INFORMATION FOR SEQ ID NO:46:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 9..530

( x i ) SEQUENCE DESCRIPTION: SEQ ID NO:46:

```
AATTCAGT ACT CCA CTG GGT CCA GCA AGC TCT CTG CCG CAG TCT TTC CTG     50
         Thr Pro Leu Gly Pro Ala Ser Ser Leu Pro Gln Ser Phe Leu
          1               5                  10

CTG AAG TCT CTC GAA CAG GTA CGT AAA ATT CAA GGC AGC GGT GCG GCT      98
Leu Lys Ser Leu Glu Gln Val Arg Lys Ile Gln Gly Ser Gly Ala Ala
 15                  20                  25                  30

CTG CAG GAA AAG CTG TGC GCA ACC TAC AAA CTG TGC CAC CCT GAG GAA     146
Leu Gln Glu Lys Leu Cys Ala Thr Tyr Lys Leu Cys His Pro Glu Glu
                 35                  40                  45

CTG GTG CTG CTC GGT CAC TCT CTG GGG ATC CCG TGG GCT CCA CTG AGC     194
Leu Val Leu Leu Gly His Ser Leu Gly Ile Pro Trp Ala Pro Leu Ser
             50                  55                  60

TCT TGC CCG TCC CAA GCT TTA CAA CTG GCA GGC TGC TTG AGC CAG CTG     242
Ser Cys Pro Ser Gln Ala Leu Gln Leu Ala Gly Cys Leu Ser Gln Leu
         65                  70                  75

CAC TCC GGT CTG TTC CTG TAC CAG GGT CTG CTG CAG GCT CTA GAA GGC     290
His Ser Gly Leu Phe Leu Tyr Gln Gly Leu Leu Gln Ala Leu Glu Gly
     80                  85                  90

ATC TCT CCT GAA TTG GGG CCC ACC CTG GAC ACA CTG CAG CTG GAC GTT     338
Ile Ser Pro Glu Leu Gly Pro Thr Leu Asp Thr Leu Gln Leu Asp Val
 95                 100                 105                 110
```

| | | | | | | | | | | | | | | | | |
|---|---|---|---|---|---|---|---|---|---|---|---|---|---|---|---|---|
| GCC | GAC | TTC | GCT | ACT | ACC | ATA | TGG | CAA | CAG | ATG | GAG | GAA | CTG | GGT | ATG | 386 |
| Ala | Asp | Phe | Ala | Thr | Thr | Ile | Trp | Gln | Gln | Met | Glu | Glu | Leu | Gly | Met | |
| | | | | 115 | | | | | 120 | | | | | 125 | | |
| GCT | CCG | GCA | CTG | CAG | CCG | ACT | CAG | GGT | GCG | ATG | CCA | GCA | TTC | GCC | TCT | 434 |
| Ala | Pro | Ala | Leu | Gln | Pro | Thr | Gln | Gly | Ala | Met | Pro | Ala | Phe | Ala | Ser | |
| | | | 130 | | | | | 135 | | | | | 140 | | | |
| GCT | TTC | CAG | CGG | CGC | GCA | GGC | GGT | GTT | CTG | GTT | GCC | TCC | CAT | CTT | CAG | 482 |
| Ala | Phe | Gln | Arg | Arg | Ala | Gly | Gly | Val | Leu | Val | Ala | Ser | His | Leu | Gln | |
| | | 145 | | | | | 150 | | | | | 155 | | | | |
| AGC | TTC | CTC | GAG | GTG | TCT | TAC | CGC | GTT | CTG | CGT | CAC | CTG | GCC | CAG | CCG | 530 |
| Ser | Phe | Leu | Glu | Val | Ser | Tyr | Arg | Val | Leu | Arg | His | Leu | Ala | Gln | Pro | |
| | 160 | | | | | 165 | | | | | 170 | | | | | |
| TAAG | | | | | | | | | | | | | | | | 534 |

( 2 ) INFORMATION FOR SEQ ID NO:47:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

GAATTCAACA AAACGGTTGA CAACATGAAG TAAACACGGT ACGATGTACC ACAAGTTCAC    60

GTAAAAGGG TATCGACAAT G    81

( 2 ) INFORMATION FOR SEQ ID NO:48:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

TCGACATTAT ATTACTAATT AATTGGGGAC CCTAGAGGTC CCCTTTTTTA TTTTAAAAAG    60

CATGCGA    67

( 2 ) INFORMATION FOR SEQ ID NO:49:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TCGACATTAT ATTACTAATT AATTGGGGAC CCTAGAGGTC CCCTTTTTTA TTTTAAAAGC    60

ATGCGGATCC C    71

( 2 ) INFORMATION FOR SEQ ID NO:50:

( i ) SEQUENCE CHARACTERISTICS:
        ( A ) LENGTH: 118 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

AATTCTGGCA AATATTCTGA AATGAGCTGT TGACAATTAA TCATCGAACT AGTTAACTAG    60

TACGCAGAGC TCAATCTAGA GGGTATTAAT AATGTTCCCA TTGGAGGATG ATTAAATG    118

( 2 ) INFORMATION FOR SEQ ID NO:51:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:51:

AGCTCCATAT GGTACCAGAT CTCTCGAGAG TACTT                                    35

( 2 ) INFORMATION FOR SEQ ID NO:52:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:52:

AGCTCAGCTG CAGCATATGG TAC                                                  23

( 2 ) INFORMATION FOR SEQ ID NO:53:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:53:

TCGACATTAT ATTACTAATT AATTGGGGAC CCTAGAGGTC CCCTTTTTA TTTTAAAAAG            60

CATGCGGATC CC                                                              72

( 2 ) INFORMATION FOR SEQ ID NO:54:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:54:

AATTCAACAA AACGGTTGAC AACATGAAGT AAACACGGTA CGATGTACCA CAAGTTCACG           60

TAAAAAGGGT ATCGACAATG GTAC                                                 84

( 2 ) INFORMATION FOR SEQ ID NO:55:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:55:

CATTGTCGAT ACCCTTTTTA CGTGAACTTG TGGTACATCG TACCGTGTTT ACTTCATGTT           60

GTCAACCGTT TTGTTG                                                          76

( 2 ) INFORMATION FOR SEQ ID NO:56:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:56:

AATTCGCATG CGGATCCATC GATC                                                 24

( 2 ) INFORMATION FOR SEQ ID NO:57:

( i ) SEQUENCE CHARACTERISTICS:
      ( A ) LENGTH: 166 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:57:

| CGATAAAAAA | AAGCCCGCTC | ATTAGGCGGG | CTAAGCTTGC | ATGCCTGCAG | GTCGACTCTA | 60 |
| GAGGATCCCC | GGGTACCATT | GTCGATACCC | TTTTTACGTG | AACTTGCGTA | CTAGTTAACT | 120 |
| AGTTCGATGA | TTAATTGTCA | ACAGCTCATT | TCAGAATATT | TGCCAG | | 166 |

( 2 ) INFORMATION FOR SEQ ID NO:58:

( i ) SEQUENCE CHARACTERISTICS:
      ( A ) LENGTH: 67 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:58:

| AGCTTCGCAT | GCTTTTAAA | ATAAAAAGG | GGACCTCTAG | GGTCCCCAAT | TAATTAGTAA | 60 |
| TATAATG | | | | | | 67 |

( 2 ) INFORMATION FOR SEQ ID NO:59:

( i ) SEQUENCE CHARACTERISTICS:
      ( A ) LENGTH: 71 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:59:

| CAAGGGGATC | CGCATGCTTT | TAAAATAAAA | AAGGGGACCT | CTAGGGTCCC | CAATTAATTA | 60 |
| GTAATATAAT | G | | | | | 71 |

( 2 ) INFORMATION FOR SEQ ID NO:60:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:60:

CTAGAAGTAC TCTCGAGAGA TCTGGTACCA TATGG                    35

( 2 ) INFORMATION FOR SEQ ID NO:61:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:61:

CATATGCTGC AGCTG                                         15

( 2 ) INFORMATION FOR SEQ ID NO:62:

( i ) SEQUENCE CHARACTERISTICS:
      ( A ) LENGTH: 72 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:62:

```
CAAGGGGATC CGCATGCTTT TTAAAATAAA AAAGGGGACC TCTAGGGTCC CCAATTAATT      60

AGTAATATAA TG                                                          72
```

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

```
CCGAGATCGA TGGATCCGCA TGCG                                             24
```